(12) United States Patent
Zhang et al.

(10) Patent No.: US 9,345,766 B2
(45) Date of Patent: *May 24, 2016

(54) COMBINATION THERAPIES COMPRISING ANTI-ERBB3 AGENTS

(71) Applicant: Merrimack Pharmaceuticals, Inc., Cambridge, MA (US)

(72) Inventors: Bo Zhang, Lynnfield, MA (US); Charlotte McDonagh, Winchester, MA (US); Alexandra Huhalov, Cambridge, MA (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/015,776

(22) Filed: Aug. 30, 2013

(65) Prior Publication Data

US 2014/0079703 A1    Mar. 20, 2014

Related U.S. Application Data

(60) Provisional application No. 61/695,242, filed on Aug. 30, 2012.

(51) Int. Cl.

| | | |
|---|---|---|
| *A61K 39/395* | (2006.01) | |
| *C07K 16/46* | (2006.01) | |
| *A61K 45/06* | (2006.01) | |
| *A61K 31/565* | (2006.01) | |
| *A61K 31/138* | (2006.01) | |
| *A61K 31/4196* | (2006.01) | |
| *A61K 31/517* | (2006.01) | |
| *A61K 33/24* | (2006.01) | |
| *A61K 31/7068* | (2006.01) | |
| *C07K 16/32* | (2006.01) | |
| *A61K 31/337* | (2006.01) | |
| *A61K 31/436* | (2006.01) | |
| *A61K 31/519* | (2006.01) | |
| *A61K 31/567* | (2006.01) | |
| *C07K 16/28* | (2006.01) | |
| *C07K 16/40* | (2006.01) | |
| *A61K 39/00* | (2006.01) | |

(52) U.S. Cl.
CPC ........... *A61K 39/3955* (2013.01); *A61K 31/138* (2013.01); *A61K 31/337* (2013.01); *A61K 31/4196* (2013.01); *A61K 31/436* (2013.01); *A61K 31/517* (2013.01); *A61K 31/519* (2013.01); *A61K 31/565* (2013.01); *A61K 31/567* (2013.01); *A61K 31/7068* (2013.01); *A61K 33/24* (2013.01); *A61K 39/39558* (2013.01); *A61K 45/06* (2013.01); *C07K 16/2863* (2013.01); *C07K 16/32* (2013.01); *C07K 16/40* (2013.01); *C07K 16/468* (2013.01); *A61K 2039/505* (2013.01); *A61K 2039/507* (2013.01); *C07K 2317/31* (2013.01)

(58) Field of Classification Search
USPC ..................................... 424/136.1; 530/387.3
See application file for complete search history.

(56) References Cited

U.S. PATENT DOCUMENTS

| | | | |
|---|---|---|---|
| 4,450,103 | A | 5/1984 | Konrad et al. |
| 4,588,585 | A | 5/1986 | Mark et al. |
| 4,704,692 | A | 11/1987 | Ladner |
| 4,737,462 | A | 4/1988 | Mark et al. |
| 4,816,567 | A | 3/1989 | Cabilly et al. |
| 4,946,778 | A | 8/1990 | Ladner et al. |
| 4,959,314 | A | 9/1990 | Mark et al. |
| 5,091,513 | A | 2/1992 | Huston et al. |
| 5,132,405 | A | 7/1992 | Huston et al. |
| 5,168,062 | A | 12/1992 | Stinski |
| 5,258,498 | A | 11/1993 | Huston et al. |
| 5,260,203 | A | 11/1993 | Ladner et al. |
| 5,292,658 | A | 3/1994 | Cormier et al. |
| 5,385,839 | A | 1/1995 | Stinski |

(Continued)

FOREIGN PATENT DOCUMENTS

| | | | |
|---|---|---|---|
| AU | 612370 B | 12/1988 | |
| AU | 648591 B | 2/1992 | |

(Continued)

OTHER PUBLICATIONS

Oyama et al. (Cancer Res, Apr. 15, 2011, 71, Abstract No. 654).*

(Continued)

*Primary Examiner* — Yan Xiao

(74) *Attorney, Agent, or Firm* — Clark & Elbing LLP

(57) ABSTRACT

Disclosed are methods and compositions for inhibiting the growth of a tumor (e.g., a malignant tumor) in a subject. In particular, combination therapies for treating a tumor in a subject by co-administering an agent selected from i) an effective amount of an anti-estrogen agent; ii) an effective amount of a receptor tyrosine kinase inhibitor; iii) an effective amount of a MEK/PI3 kinase/AKT inhibitor; iv) an effective amount of MM-151; v) an effective amount of an mTOR inhibitor; and/or vi) an effective amount of trastuzumab or TMD1, and/or combinations thereof; and an effective amount of a bispecific anti-ErbB2/anti-ErbB3 antibody. Also disclosed is a bispecific anti-ErbB2/anti-ErbB3 antibody for use in the therapy of a tumor in combination with an agent selected from i) an effective amount of an anti-estrogen agent; ii) an effective amount of a receptor tyrosine kinase inhibitor; iii) an effective amount of a MEK/PI3 kinase/AKT inhibitor; iv) an effective amount of MM-151; v) an effective amount of an mTOR inhibitor; and/or vi) an effective amount of trastuzumab or TMD1, and/or combinations thereof.

5 Claims, 39 Drawing Sheets

(56) References Cited

U.S. PATENT DOCUMENTS

| | | |
|---|---|---|
| 5,455,030 A | 10/1995 | Ladner et al. |
| 5,476,786 A | 12/1995 | Huston |
| 5,482,858 A | 1/1996 | Huston et al. |
| 5,518,889 A | 5/1996 | Ladner et al. |
| 5,525,491 A | 6/1996 | Huston et al. |
| 5,530,101 A | 6/1996 | Queen et al. |
| 5,534,254 A | 7/1996 | Huston et al. |
| 5,534,621 A | 7/1996 | Ladner et al. |
| 5,612,196 A | 3/1997 | Becquart et al. |
| 5,622,701 A | 4/1997 | Berg |
| 5,631,158 A | 5/1997 | Dorai et al. |
| 5,656,730 A | 8/1997 | Lee |
| 5,658,763 A | 8/1997 | Dorai et al. |
| 5,670,356 A | 9/1997 | Sherf et al. |
| 5,730,978 A | 3/1998 | Wayner |
| 5,733,782 A | 3/1998 | Dorai et al. |
| 5,738,845 A | 4/1998 | Imakawa |
| 5,753,204 A | 5/1998 | Huston et al. |
| 5,753,627 A | 5/1998 | Albert et al. |
| 5,763,733 A | 6/1998 | Whitlow et al. |
| 5,766,883 A | 6/1998 | Ballance et al. |
| 5,767,260 A | 6/1998 | Whitlow et al. |
| 5,780,594 A | 7/1998 | Carter |
| 5,800,815 A | 9/1998 | Chestnut et al. |
| 5,821,231 A | 10/1998 | Arrhenius et al. |
| 5,837,846 A | 11/1998 | Huston et al. |
| 5,840,299 A | 11/1998 | Bendig et al. |
| 5,856,456 A | 1/1999 | Whitlow et al. |
| 5,869,448 A | 2/1999 | Arrhenius et al. |
| 5,869,620 A | 2/1999 | Whitlow et al. |
| 5,874,540 A | 2/1999 | Hansen et al. |
| 5,876,969 A | 3/1999 | Fleer et al. |
| 5,914,110 A | 6/1999 | Holmes et al. |
| 5,917,021 A | 6/1999 | Lee |
| 5,928,904 A | 7/1999 | Holmes et al. |
| 5,936,065 A | 8/1999 | Arrhenius et al. |
| 5,977,322 A | 11/1999 | Marks et al. |
| 5,990,275 A | 11/1999 | Whitlow et al. |
| 6,025,165 A | 2/2000 | Whitlow et al. |
| 6,027,725 A | 2/2000 | Whitlow et al. |
| 6,033,665 A | 3/2000 | Yednock |
| 6,103,889 A | 8/2000 | Whitlow et al. |
| 6,121,424 A | 9/2000 | Whitlow et al. |
| 6,171,809 B1 | 1/2001 | Roelant |
| 6,191,269 B1 | 2/2001 | Pollock et al. |
| 6,197,794 B1 | 3/2001 | Head et al. |
| 6,207,804 B1 | 3/2001 | Huston et al. |
| 6,210,670 B1 | 4/2001 | Berg |
| 6,229,011 B1 | 5/2001 | Chen et al. |
| 6,265,572 B1 | 7/2001 | Chen et al. |
| 6,288,267 B1 | 9/2001 | Hull et al. |
| 6,323,322 B1 | 11/2001 | Filpula et al. |
| 6,329,372 B1 | 12/2001 | Head et al. |
| 6,331,415 B1 | 12/2001 | Cabilly et al. |
| 6,333,396 B1 | 12/2001 | Filpula et al. |
| 6,348,463 B1 | 2/2002 | Head et al. |
| 6,362,204 B1 | 3/2002 | Head et al. |
| 6,365,619 B1 | 4/2002 | Shi |
| 6,380,387 B1 | 4/2002 | Sidduri et al. |
| 6,388,084 B1 | 5/2002 | Kaplan et al. |
| 6,423,512 B1 | 7/2002 | Digan et al. |
| 6,423,728 B1 | 7/2002 | Hull et al. |
| 6,426,348 B1 | 7/2002 | Hull et al. |
| 6,445,550 B1 | 9/2002 | Ishi |
| 6,458,844 B2 | 10/2002 | Hull et al. |
| 6,479,666 B2 | 11/2002 | Hull et al. |
| 6,482,849 B1 | 11/2002 | Lobl et al. |
| 6,495,525 B1 | 12/2002 | Lee et al. |
| 6,515,110 B1 | 2/2003 | Filpula et al. |
| 6,596,752 B1 | 7/2003 | Lobl et al. |
| 6,602,503 B1 | 8/2003 | Lobb et al. |
| 6,667,331 B2 | 12/2003 | Duplantier et al. |
| 6,668,527 B2 | 12/2003 | Duplantier et al. |
| 6,677,436 B1 | 1/2004 | Sato et al. |
| 6,685,617 B1 | 2/2004 | Blinn et al. |
| 6,686,179 B2 | 2/2004 | Fleer et al. |
| 6,692,942 B2 | 2/2004 | Filpula et al. |
| 6,743,896 B2 | 6/2004 | Filpula et al. |
| 6,743,908 B2 | 6/2004 | Filpula et al. |
| 6,764,853 B2 | 7/2004 | Filpula et al. |
| 6,806,365 B2 | 10/2004 | Chen et al. |
| 6,818,216 B2 | 11/2004 | Young et al. |
| 6,835,738 B1 | 12/2004 | Brown et al. |
| 6,855,706 B2 | 2/2005 | Satake et al. |
| 6,872,719 B1 | 3/2005 | Brown et al. |
| 6,878,718 B2 | 4/2005 | Brand et al. |
| 6,903,128 B2 | 6/2005 | Duplantier et al. |
| 6,905,688 B2 | 6/2005 | Rosen et al. |
| 6,911,451 B1 | 6/2005 | Porter et al. |
| 6,916,933 B2 | 7/2005 | Kaplan et al. |
| 6,926,898 B2 | 8/2005 | Rosen et al. |
| 6,946,134 B1 | 9/2005 | Rosen et al. |
| 6,962,978 B2 | 11/2005 | Pepinsky et al. |
| 6,972,322 B2 | 12/2005 | Fleer et al. |
| 6,987,006 B2 | 1/2006 | Fleer et al. |
| 6,989,365 B2 | 1/2006 | Fleer et al. |
| 6,994,857 B2 | 2/2006 | Rosen et al. |
| 7,015,216 B2 | 3/2006 | Konradi et al. |
| 7,045,318 B2 | 5/2006 | Ballance |
| 7,067,313 B1 | 6/2006 | Jacquemin et al. |
| 7,105,520 B2 | 9/2006 | Suzuki et al. |
| 7,141,547 B2 | 11/2006 | Rosen et al. |
| 7,153,963 B2 | 12/2006 | Makino et al. |
| 7,160,874 B2 | 1/2007 | Tanaka et al. |
| 7,183,092 B2 | 2/2007 | Choi et al. |
| 7,189,690 B2 | 3/2007 | Rosen et al. |
| 7,193,108 B2 | 3/2007 | Chiba et al. |
| 7,238,344 B2 | 7/2007 | Pedersen et al. |
| 7,238,660 B2 | 7/2007 | Rosen et al. |
| 7,238,667 B2 | 7/2007 | Rosen et al. |
| 7,250,516 B2 | 7/2007 | Okuzumi et al. |
| 7,291,645 B2 | 11/2007 | Konradi et al. |
| 7,332,580 B2 | 2/2008 | Adams et al. |
| 7,332,585 B2 | 2/2008 | Adams et al. |
| 7,482,013 B2 | 1/2009 | Ballance et al. |
| 8,691,771 B2 | 4/2014 | Nielsen et al. |
| 8,927,694 B2 | 1/2015 | McDonagh et al. |
| 2002/0031508 A1 | 3/2002 | Wagner et al. |
| 2002/0107284 A1 | 8/2002 | Uckun et al. |
| 2002/0151011 A1 | 10/2002 | Fleer et al. |
| 2003/0004196 A1 | 1/2003 | Duplantier et al. |
| 2003/0018016 A1 | 1/2003 | Adams et al. |
| 2003/0022308 A1 | 1/2003 | Fleer et al. |
| 2003/0036170 A1 | 2/2003 | Fleer et al. |
| 2003/0036172 A1 | 2/2003 | Fleer et al. |
| 2003/0054554 A1 | 3/2003 | Becquart et al. |
| 2003/0054994 A1 | 3/2003 | Noteborn et al. |
| 2003/0078249 A1 | 4/2003 | Baldwin et al. |
| 2003/0082747 A1 | 5/2003 | Fleer et al. |
| 2003/0083267 A1 | 5/2003 | Adams et al. |
| 2003/0086919 A1 | 5/2003 | Rosenblum et al. |
| 2003/0100585 A1 | 5/2003 | Duplantier et al. |
| 2003/0104578 A1 | 6/2003 | Ballance |
| 2003/0119042 A1 | 6/2003 | Franco De Sarabia Rosado et al. |
| 2003/0166559 A1 | 9/2003 | Desjarlais et al. |
| 2004/0039040 A1 | 2/2004 | Takahashi et al. |
| 2004/0053907 A1 | 3/2004 | Zheng et al. |
| 2004/0087574 A1 | 5/2004 | Takahashi et al. |
| 2004/0102496 A1 | 5/2004 | Duplantier et al. |
| 2004/0132809 A1 | 7/2004 | Scott et al. |
| 2004/0175824 A1 | 9/2004 | Sun et al. |
| 2004/0224389 A1 | 11/2004 | Bellgrau et al. |
| 2004/0229858 A1 | 11/2004 | Baldwin et al. |
| 2004/0229859 A1 | 11/2004 | Albers et al. |
| 2004/0247565 A1 | 12/2004 | Liu et al. |
| 2004/0265311 A1 | 12/2004 | Wagner et al. |
| 2005/0020815 A1 | 1/2005 | Carter |
| 2005/0100991 A1 | 5/2005 | Rosen et al. |
| 2005/0186664 A1 | 8/2005 | Rosen et al. |
| 2005/0187177 A1 | 8/2005 | Godbey et al. |
| 2005/0226876 A1 | 10/2005 | Graus et al. |
| 2005/0265962 A1 | 12/2005 | Desjarlais et al. |
| 2005/0266533 A1 | 12/2005 | Ballance et al. |
| 2006/0014966 A1 | 1/2006 | Lee et al. |

(56) References Cited

U.S. PATENT DOCUMENTS

| | | |
|---|---|---|
| 2006/0018859 A1 | 1/2006 | Carter |
| 2006/0030553 A1 | 2/2006 | Zheng et al. |
| 2006/0099205 A1 | 5/2006 | Adams et al. |
| 2006/0166866 A1 | 7/2006 | Adams et al. |
| 2006/0166961 A1 | 7/2006 | Scott et al. |
| 2006/0211630 A1 | 9/2006 | Cossio et al. |
| 2006/0241132 A1 | 10/2006 | Ishigaki et al. |
| 2007/0031423 A1 | 2/2007 | Fanger et al. |
| 2007/0041987 A1 | 2/2007 | Carter et al. |
| 2007/0054909 A1 | 3/2007 | Baldwin et al. |
| 2007/0066533 A1 | 3/2007 | Lee et al. |
| 2007/0086942 A1 | 4/2007 | Chang et al. |
| 2007/0232601 A1 | 10/2007 | Yoneda et al. |
| 2007/0243163 A1 | 10/2007 | Liu |
| 2007/0274950 A1 | 11/2007 | Patten et al. |
| 2008/0004206 A1 | 1/2008 | Rosen et al. |
| 2008/0113411 A1 | 5/2008 | Sheffer et al. |
| 2008/0113412 A1 | 5/2008 | Sheffer et al. |
| 2008/0124334 A1 | 5/2008 | Akita et al. |
| 2008/0125574 A1 | 5/2008 | Sheffer et al. |
| 2008/0166358 A1 | 7/2008 | Tung |
| 2008/0267962 A1 | 10/2008 | Ballance et al. |
| 2009/0226429 A1 | 9/2009 | Salcedo et al. |
| 2010/0189649 A1* | 7/2010 | Greene et al. .................. 424/9.1 |
| 2010/0280227 A1 | 11/2010 | Ambrose et al. |
| 2011/0059076 A1 | 3/2011 | McDonagh et al. |
| 2012/0003221 A1 | 1/2012 | McDonagh et al. |
| 2014/0017264 A1 | 1/2014 | McDonagh et al. |

FOREIGN PATENT DOCUMENTS

| | | |
|---|---|---|
| AU | 664030 B2 | 10/1992 |
| CA | 2100671 A1 | 9/1992 |
| CA | 1341364 C | 6/2002 |
| CA | 1341415 C | 1/2003 |
| CN | 1074243 A | 7/1993 |
| CN | 1146664 C | 4/2004 |
| CN | 101072581 A | 11/2007 |
| CN | 101120021 A | 2/2008 |
| EP | 0281604 B1 | 9/1988 |
| EP | 0318554 B2 | 6/1989 |
| EP | 0399666 A1 | 11/1990 |
| EP | 0413622 A1 | 2/1991 |
| EP | 0573551 B1 | 12/1993 |
| EP | 0623679 A1 | 11/1994 |
| EP | 0624195 B1 | 11/1994 |
| EP | 1136556 A1 | 9/2001 |
| EP | 0870039 B1 | 3/2006 |
| WO | WO-98/04718 A1 | 2/1998 |
| WO | WO-01/79271 A1 | 10/2001 |
| WO | WO-02/0914 A2 | 1/2002 |
| WO | WO-03/060071 A2 | 7/2003 |
| WO | WO-2005/117973 A2 | 12/2005 |
| WO | WO-2005/118642 A2 | 12/2005 |
| WO | WO-2006/091209 A2 | 8/2006 |
| WO | WO-2008/014493 A3 | 1/2008 |
| WO | WO-2008/030558 A2 | 3/2008 |
| WO | WO-2008/033413 A2 | 3/2008 |
| WO | WO-2008/140493 A2 | 11/2008 |
| WO | WO-2009/126920 A2 | 10/2009 |
| WO | WO-2010/059315 A1 | 5/2010 |
| WO | WO-2011/133668 A2 | 10/2011 |

OTHER PUBLICATIONS

Rimawi et al. (Clin Cancer Res, Dec. 7, 2010, 17(6): 1351-61).*
Gilmartin et al. (Clin Cancer Res, Published Online First Jan. 18, 2011, 17(5): 989-1000).*
Anderson et al., "Perspective—FcRn transports albumin: relevance to immunology and medicine," Trends Immunol. 27(7):343-348 (2006).
Arya et al., "Rapid synthesis and introduction of a protected EDTA-like group during the solid-phase assembly of peptides," Bioconjug Chem. 2(5):323-26 (1991).
Bai et al., "Improving the oral efficacy of recombinant granulocyte colony-stimulating factor and transferrin fusion protein by spacer optimization," Pharm Res. 23(9):21 16-21 (2006).
Bera et al., "A bivalent disulfide-stabilized Fv with improved antigen binding to erbB2," J Mol Biol. 281(3): 475-83 (1998).
Bird et al., "Single-chain antigen-binding proteins," Science. 242:423-426 (1988).
Breast cancer cell line ZR7530, National Institutes of Health: Lawrence Berkeley National Laboratory, retrieved Jul. 31, 2012 from http://icbp.lbl.gov/ccc/viewline.php?id=69 (1 page).
Brennan et al., "Albumin Redhill (−1 Arg, 320 Ala—Thr): A glycoprotein variant of human serum albumin whose precursor has an aberrant signal peptidase cleavage site," Proc Natl Sci USA. 87:26-30 (1990).
Britsch et al., "The ErbB2 and ErbB3 receptors and their ligand, neuregulin-1, are essential for development of the sympathetic nerve system," Genes Dev. 12(12):1825-36 (1998).
Carlson et al., "Alloalbuminemia in sweden: structural study and penotypic distribution of nine albumin variants," Proc Natl Aced Sci USA. 89:8225-29 (1992).
Chapman et al., "Therapeutic antibody fragments with prolonged in vivo half-lives," Nat Biotechnol. 17(8):780-83 (1999).
Chapman, "PEGylated antibodies and antibody fragments for improved therapy: a review," Adv Drug Deliv Rev. 54(4):531-45 (2002).
Chaudhury et al., "Albumin binding to FcRn: distinct from the FcRn-IgG interaction," Biochemistry. 45(17):4983-90 (2006).
Chaudhury et al., "The major histocompatibility complex-related Fc receptor for IgG (FcRn) binds albumin and prolongs its lifespan," J Exp Med. 197(3):315-22 (2003).
Christodoulou et al., "1H NMR of albumin in human blood plasma: drug binding and redox reactions at Cys34," FEBS Lett. 376(1-2):1-5 (1995).
Chua et al., "Albumin Church Bay: 560 Lys—>Glu a new mutation detected by electrospray ionisation mass spectrometry," Biochem Biophys Acta. 1382(2):305-310 (1998).
Clackson et al., "Making antibody fragments using phage display libraries," Nature. 352:624-28 (1991).
Dennis et al., "Albumin binding as a general strategy for improving the pharmacokinetics of proteins," J Biol Chem. 277(38):35035-43 (2002).
Di Fiore et al., "erbB-2 is a potent oncogene when overexpressed in NIH/3T3 cells," Science. 237(4811):178-82 (1987).
Dockal et al., "The three recombinant domains of human serum albumin. Structural characterization and ligand binding properties," J Biol Chem. 274(41):29303-10 (1999).
Doronina et al., "Development of potent monoclonal antibody auristatin conjugates for cancer therapy," Nat Biotechnol. 21(7):778-84 (2003).
Drummond et al., "Enhanced pharmacodynamic and antitumor properties of a histone deacetylase inhibitor encapsulated in liposomes or ErbB2-targeted immunoliposomes," Clin Cancer Res. 11(9):3392-3401 (2005).
Engel et al., "Establishment and characterization of three new continuous cell lines derived from human breast carcinomas," Cancer Res. 38(10):3352-64 (1978).
Engelman et al., "MET amplification leads to gefitinib resistance in lung cancer by activating ERBB3 signaling," Science. 316(5827):1039-43 (2007).
Erickson et al., "ErbB3 is required for normal cerebellar and cardiac development: a comparison with ErbB2-and heregulin-deficient mice," Development. 124(24):4999-5011 (1997).
Fang et al., "Characterization of an anti-human ovarian carcinomaxanti-human CD3 bispecific single-chain antibody with an albumin-original interlinker," Gynecol Oncol. 92(1):135-46 (2004).
Fogh et al., "Absence of HeLa Cell Contamination in 169 Cell Lines Derived From Human Tumors," *J Natl Cancer Inst* 58(2):209-214, 1977.
Folgiero et al., "Induction of ErbB-3 expression by alpha6beta4 Integrin contributes to tamoxifen resistance in ERbeta1-negative breast carcinomas," PLoS ONE. 3(2):e1592(1-12) (2008).
Galliano et al., "Mutations in genetic variants of human serum albumin found in Italy," Proc Natl Acad Sci USA. 87(22):8721-5 (1990).

(56) References Cited

OTHER PUBLICATIONS

Guy et al., "Insect cell-expressed p180erbB3 possesses an impaired tyrosine kinase activity," Proc Natl Acad Sci USA. 91(17):8132-36 (1994).

Horak et al., "Isolation of scFvs to in vitro produced extracellular domains of EGFR family members," Cancer Biother Radiopharm. 20(6):603-13 (2005).

Hudziak et al., "Increased expression of the putative growth factor receptor p185HER2 causes transformation and tumorigenesis of Nih 3T3 cells," Proc Natl Acad Sci USA. 84(20):7159-63 (1987).

Huston et al., "Protein engineering of antibody binding sites: Recovery of specific activity in an anti-digoxin single-chain FV analogue produced in *Escherichia coli*," Proc Natl Acad Sci USA. 85:5879-83 (1988).

Hutcheson et al., "Heregulin bete1 drives gefitinib-resistant growth and invasion in tamoxifen-resistant MCF-7 breast cancer cells," Breast Cancer Res. 9(4):R50 1-14 (2007).

Hutchinson et al., "The N-terminal sequence of albumin Redhill, a variant of human serum albumin," FEBS Lett. 193(2):211-12 (1985).

Jenkins, "Modifications of therapeutic proteins: challenges and prospects," Cytotechnology. 53(1-3):121-25 (2007).

Karacay et al., "Pretargeting for cancer radioimmunotherapy with bispecific antibodies: role of the bispecific antibody's valency for the tumor target antigen," Bioconjug Chem. 13(5):1054-70 (2002).

Kem et al., "Purification and characterization of the cytotoxic cerebratulus A toxins," J Biol Chem. 253(16):5752-57 (1978).

Kirpotin et al., "Antibody targeting of long-circulation lipidic nanoparticles does not increase tumor localization but does increase internalization in animal models," Cancer Res. 66:6732-40 (2006).

Klepper et al., "The ErbB-2/HER2 oncoprotein of human carcinomas may function solely as a shared coreceptor for multiple stroma-derived growth factors," Proc Natl Acad Sci USA. 96(9):4995-5000 (1999).

Koumakpayi et al., "Expression and nuclear localization of ErbB3 in prostate cancer," Clin Cancer Res. 12(9):2730-37 (2006).

Köhler et al., "Continuous cultures of fused cells secreting antibody of predefined specificity," Nature. 256:495-497 (1975).

Langer, "New methods of drug delivery," Science. 249(4976):1527-33 (1990).

Lemmens et al., "Role of neuregulin-1/ErbB signaling in cardiovascular physiology and disease: implications for therapy of heart failure," Circulation. 116(8):954-60 (2007).

Lemoine et al., "Expression of the ERBB3 gene product in breast cancer," Br J Cancer. 66(6):1116-21 (1992).

Leuschner et al., "Targeting breast and prostate cancers through their hormone receptors," Biol Reprod. 73:860-65 (2005).

Liu et al., "Downregulation of erbB3 abrogates erbB2-mediated tamoxifen resistance in breast cancer cells," Int J Cancer. 120(9):1874-82 (2007).

Lonberg et al., "Antigen-specific human antibodies from mice comprising four distinct genetic modifications," Nature. 368(6474):856-59 (1994).

Madison et al., "Genetic variants of human serum albumin in Italy: point mutants and a carboxyl-terminal variant," Proc Natl Aced Sci USA. 91(41):6476-80 (1994).

Marks et al., "By-passing immunization. Human antibodies from V-gene libraries displayed on phage," J Mol Biol. 222:581-97 (1991).

Masuda et al., "cDNA cloning and characterization of vascular apoptosis-inducing protein 1," Biochem Biophys Res Commun. 278:197-204 (2000).

McCurdy et al., "A covalently linked recombinant albumin dimer is more rapidly cleared in vivo than are wild-type and mutant C34A albumin," J Lab Clin Med. 143(2):115-24 (2004).

Minchiotti et al., "Structural characterization of four genetic variants of human serum albumin associated with alloabuminemia in Italy," Eur J Biochem. 247:476-82 (1997).

Müller et al., "Improved pharmacokinetics of recombinant bispecific antibody molecules by fusion to human serum albumin," J Biol Chem. 282(17):12650-60 (2007).

Naidu et al., "Expression of c-erbB3 protein in primary breast carcinomas," Br J Cancer. 78(10):1385-90 (1998).

Nakaoka et al., "Gab family proteins are essential for postnatal maintenance of cardiac function via neuregulin-1/ErbB signaling," J Clin Invest. 117(7):1771-81 (2007).

Neve et al., "Biological effects of anti-ErbB2 single chain antibodies selected for internalizing function," Biochem Biophys Res Commun. 280(1):274-79 (2001).

Nielsen et al., "Using computational modeling to drive the development of targeted therapeutics," IDrugs. 8(10):822-26 (2005).

Park et al., "Anti-HER2 immunoliposomes: Enhanced efficacy attributable to targeted delivery," Clin Cancer Res. 8:1172-81 (2002).

Peach et al., "Structural characterization of a glycoprotein variant of human serum albumin: albumin casebrook (494 Asp—Asn)," Biochim Biophys Acta. 1097:49-54 (1991).

Press et al., "Expression of the HER-2/neu proto-oncogene in normal human adult and fetal tissues," Oncogene. 5(7):953-62 (1990).

Prigent et al., "Expression of the c-erbB-3 protein in normal human adult and fetal tissues," Oncogene. 7(7):1273-78 (1992).

Robinson et al., "Molecular clocks," Proc Natl Acad Sci USA. 98(3):944-49 (2001).

Robinson et al., "Targeting ErbB2 and ErbB3 with a bispecific single-chain Fv enhances targeting selectivity and induces a therapeutic effect in vitro," Br J Cancer. 99(9):1415-25 (2008).

Schier et al., "In vitro and in vivo characterization of a human anti-c-erbB-2 single-chain Fv isolated from a filamentous phage antibody library," Immunotechnology. 1(1):73-81 (1995).

Schier et al., "Isolation of picomolar affinity anti-c-erbB-2 single-chain Fv by molecular evolution of the complementarity determining regions in the center of the antibody binding site," J Mol Biol 263(4):551-67 (1996).

Sergina et al., "Escape from HER-family tyrosnie kinase inhibitor therapy by the kinase-inactive HER3," Nature. 445(7126):437-41 (2007) (11 pages).

Sheets et al., "Efficient construction of a large nonimmune phage antibody library: the production of high-affinity human single-chain antibodies to protein antigens," Proc Natl Acad Sci USA. 95(11):6157-62 (1998).

Simon et al., "Accelerated titration designs for phase I clinical trials in oncology," J Natl Cancer Inst. 89(15):1138-47 (1997).

Singh et al., "Labeling of antibodies by in situ modification of thiol groups generated from selenol-catalyzed reduction of native disulfide bonds," Anal Biochem. 304:147-56 (2002).

Smith et al., "Prolonged in vivo residence times of antibody fragments associated with albumin," Bioconjug Chem. 12(5):750-56 (2001).

Soltoff et al., "ErbB3 is involved in activation of phosphatidylinositol 3-kinase by epidermal growth factor," Mol Cell Biol. 14(6):3550-58 (1994).

Sugio et al., "Crystal structure of human serum albumin at 2.5 resolution," Protein Eng. 12:439-46 (1999).

Takada et al., "The primary structure of the alpha$^4$ subunit of VLA-4: homology to other integrins and a possible cell-cell adhesion function," EEMBO J. 8(5):1361-68 (1989).

Tanner et al., "ErbB-3 predicts survival in ovarian cancer," J Clin Oncol. 24(26):4317-23 (2006).

Tarkony, "Genetic and drug-induced variation in serum albumin," Adv Clin Chem. 21:101-46 (1980).

Thorpe et al., "The preparation and cytotoxic properties of antibody-toxin conjugates," Immunol Rev. 62:119-58 (1982).

Tokunaga et al., "Deregulation of the AKT pathway in human cancer," Curr Cancer Drug Targets. 8(1):27-36 (2008).

Tsukada et al., "The effect of bispecific monoclonal antibody recognizing both hepatomaspecific membrane glycoprotein and anthraycycline drugs on the metastatic growth of hepatoma AH66," Cancer Biochem Biophys. 10(3):247-56 (1989).

van der Horst et al., "Anti-HER-3 MAbs inhibit HER-3-mediated signaling in breast cancer cell lines resistant to Anti-HER-2 antibodies," Int J Cancer. 115(4):519-27 (2005).

Vivanco et al., "The phosphatidylinositol 3-kinase AKT pathway in human cancer," Nat Rev Cancer. 2(7):489-501 (2002).

(56) References Cited

OTHER PUBLICATIONS

Völkel et al., "Optimized linker sequences for the expression of monomeric and dimeric bispecific single-chain diabodies," Protein Eng. 14(10):815-23 (2001).

Wallasch et al., "Heregulin-dependent regulation of HER2/neu oncogenic signaling by heterodimerization with HER3," EMBO J. 14(17):4267-75 (1995).

Ward et al., "Binding activities of a repertoire of single immunoglobulin variable domains secreted from *Escherichia coli*," Nature. 341:544-46 (1989).

Yarden et al., "Untangling the ErbB signalling network," Nat Rev Mol Cell Biol 2(2):127-137 (2001).

Yukawa et al., "Bispecific rabbit fab'-bovine serum albumin conjugate use in hemagglutination immunoassay for beta-microseminoprotein," J Immunoassay. 18(3):215-33 (1997).

Zahn-Zabal et al., "Development of stable cell lines for production or regulated expression using matrix attachment regions," J Biotechnol. 87(1):29-42 (2001).

English Translation of Office Action in Eurasian Patent Application No. 201001625 (2 pages).

Examination Report for New Zealand Patent Application No. 589086, dated Mar. 23, 2011 (3 pages).

Extended European Search Report and Search Opinion for European Patent Application No. 09730096.6, dated Jan. 16, 2013 (9 pages).

Invitation to Respond to Written Opinion in Singapore Patent Application No. 2010074375, mailed on Sep. 21, 2012 (17 pages).

International Preliminary Report on Patentability and Written Opinion for International Patent Application No. PCT/US2012/026602, dated Oct. 22, 2013 (7 pages).

International Search Report for International Application No. PCT/US2009/040259 mailed on Jan. 26, 2010 (5 pages).

International Search Report for International Application No. PCT/US09/60721, mailed on Apr. 13, 2010 (5 pages).

International Preliminary Report on Patentability for International Application No. PCT/US2009/060721, issued May 24, 2011 (7 pages).

International Search Report for International Application No. PCT/US2012/026602, mailed Jun. 8, 2012 (4 pages).

International Preliminary Report on Patentability and Written Opinion of the International Searching Authority for International Application No. PCT/US2011/064496, issued Jun. 25, 2013 (5 pages).

Office Action for Chinese Patent Application No. CN200980154509.9, dated Feb. 20, 2013 and English Translation (26 pages).

Written Opinion of the International Searching Authority for International Application No. PCT/US09/60721, mailed on Apr. 13, 2010 (6 pages).

Written Opinion of the International Searching Authority for International Application No. PCT/US2009/040259, mailed on Jan. 26, 2010 (7 pages).

Written Opinion of the International Searching Authority for International Application No. PCT/US2012/026602, mailed Jun. 8, 2012 (6 pages).

Office Action in Chinese Patent Application No. 200980154509.9, mailed Nov. 18, 2013 (with English Translation) (9 pages).

International Search Report for International Application No. PCT/US2013/057714, mailed Dec. 20, 2013 (5 pages).

Written Opinion of the International Searching Authority for International Application No. PCT/US2013/057714, mailed Dec. 20, 2013 (8 pages).

Chakrabarty et al., "Feedback upregulation of HER3 (ErbB3) expression and activity attenuates antitumor effect of PI3K inhibitors," Proc Natl Acad Sci USA. 109(8):2718-23 (2012).

McDonagh et al., "Antitumor activity of a novel bispecific antibody that targets the ErbB2/ErbB3 oncogenic unit and inhibits heregulin-induced activation of ErbB3," Mol Cancer Ther. 11(3):582-93 (2012) (29 pages).

Zhang et al., "Combination of MM-111, an ErbB2/ErbB3 bispecific antibody, with endocrine therapies as a treatment strategy in models of Er+/HER2+ breast cancer," Presentation at 102nd Annual Meeting of AACR (2011) (1 page).

Office Action in Japanese Patent Application No. 2011-536365 mailed Dec. 16, 2013 (with English Translation) (6 pages).

Lonberg et al., "Antigen-specific human antibodies from mice comprising four distinct genetic modifications," Nature. 368(6474):856-859 (1994).

Johnson et al., "The clinical impact of screening and other experimental tumor studies," Cancer Treat Rev. 2(1):1-31 (1975).

Office Action in Eurasian Patent Application No. 201001625, dated Jun. 28, 2013 (12 pages).

Notice of Allowance for U.S. Appl. No. 12/757,801, mailed Sep. 2, 2014 (2 pages).

Extended European Search Report for European Patent Application No. 12749889.7, mailed Jan. 7, 2015 (7 pages).

Notification Concerning Transmittal of International Preliminary Report on Patentability and Written Opinion of the International Searching Authority for International Application No. PCT/US2013/040785, mailed Jan. 15, 2015 (9 pages).

International Search Report and Written Opinion of the International Searching Authority for International Application No. PCT/US2013/040785, mailed Oct. 25, 2013 (13 pages).

International Preliminary Report on Patentability for International Application No. PCT/US2013/057714, issued Mar. 3, 2015 (10 pages).

\* cited by examiner

COMBINATION THERAPIES COMPRISING ANTI-ERBB3 AGENTS

CROSS-REFERENCE TO RELATED APPLICATIONS

This application claims priority to U.S. Provisional Application No. 61/695,242, filed Aug. 30, 2012, the contents of which are incorporated herein by reference.

FIELD OF THE INVENTION

The various aspects of the invention disclosed herein relate to methods and compositions for the treatment of cancers.

BACKGROUND OF THE INVENTION

Approximately 75% of breast cancers are estrogen receptor (ER) positive. Other cancers are also ER positive (ER+). Estrogen receptors mediate intracellular signaling that can increase the frequency of cell division and drive tumor growth. Although anti-endocrine therapies such as tamoxifen, fulvestrant, and letrozole have demonstrated significant efficacy in treating ER+ breast cancer patients, intrinsic or acquired resistance to such therapies has limited their success.

The prevalence of amplification of the human epidermal growth factor receptor 2 (HER2, or ErbB2) in breast cancer and other cancers has resulted in the research and development of drugs that have ErbB2 as a therapeutic target. Although both the anti-ErbB2 monoclonal antibody trastuzumab or TMD1 and the ErbB1/ErbB2 dual receptor tyrosine kinase inhibitor lapatinib have met with success in the clinic, many patients fail to benefit from these drugs. Additionally, the majority of patients with tumors that initially respond will eventually recrudesce after extended treatment using these therapies.

The ErbB2/ErbB3 heterodimer is the most potent ErbB receptor pairing with respect to strength of interaction, impact on receptor tyrosine phosphorylation, and effects on downstream signaling through mitogen activated protein kinase and phosphoinositide-3 kinase pathways. Heregulin is the primary ligand for ErbB3, and activates signaling by ErbB2/ErbB3 heterodimers. Current ErbB2-targeted therapies do not effectively inhibit heregulin activated signaling. MM-111 is a bispecific anti-ErbB2/anti-ErbB3 antibody that abrogates heregulin binding to ErbB2/ErbB3 and inhibits heregulin activation of ErbB2/ErbB3 without significantly affecting ErbB2 biological activity. In preclinical models of HER-2+ gastric, breast, ovarian and lung cancers, MM-111 inhibits ErbB3 phosphorylation, cell cycle progression, and tumor growth.

Thus, a need exists for therapies and therapeutic strategies providing improved inhibition of ErbB3 activation (e.g., ligand-induced activation) as well as for therapies and therapeutic strategies providing improved inhibition of estrogen receptor signaling activity or of ErB1 and ErbB2 receptor signaling activity.

In the treatment of cancers, the co-administration of pluralities of anti-cancer drugs (combination therapy) often provides better treatment outcomes than monotherapy. Such outcomes can be subadditive, additive, or superadditive. That is to say that the combined effects of two anti-cancer drugs, each of which provides a quantifiable degree of benefit, can be less than, equal to, or greater than the sum of the benefits of each drug. For example, two drug, each of which when used alone to treat a lethal cancer provides an average one year extension of progression free survival, could together provide a <24 month extension (e.g., an 18 month extension), about a 24 month extension, or a >24 month extension (e.g., a 30 month extension) of progression free survival. Typically, combination therapies for cancer treatment provide significantly subadditive outcomes. Outcomes that are near additive, additive, or superadditive are most desirable, but only occur rarely. In addition, many drugs are known to alter the bioavailability, or otherwise affect the safety profile of other drugs when both drugs are co-administered. As new drugs are first used in combination therapies, unforeseen, hazardous drug-drug interactions may be observed that result in drug-drug interaction-mediated toxicity in the patient.

Thus approaches for safely administering combination therapies comprising administration of ErbB2/ErbB3 heterodimer-targeted agents for cancer treatment, and especially combinations that yield near-additive, additive, or superadditive outcomes are needed.

SUMMARY OF THE INVENTION

Provided herein are methods and compositions effective for the inhibition of ErbB3 activation and also effective for the inhibition of estrogen receptor activation. Also provided are methods and compositions effective for the inhibition of ErbB3 activation and also effective for the inhibition of ErB1 and/or ErbB2 activation. These methods and compositions are useful for the treatment of tumors, e.g., malignant tumors, as well as for the treatment of other cancers.

In a first embodiment, a method of treating a subject with a malignant tumor is provided, where the tumor is an ErbB2 expressing or ErbB2 over-expressing tumor (e.g., $HER^{++}$ or $HER^{+++}$ tumors) and the tumor may be a melanoma, clear cell sarcoma, head and neck, endometrial, prostate, breast, ovarian, gastric, colon, colorectal, lung, bladder, pancreatic, salivary gland, liver, skin, brain or renal tumor. The method comprises co-administering to the subject an effective amount an agent selected from i) an effective amount of an anti-estrogen agent; ii) an effective amount of a receptor tyrosine kinase inhibitor; iii) an effective amount of a MEK/PI3 kinase/AKT inhibitor (e.g., those inhibitors described in the appendix and including, e.g., AZD6244, BKM-120, GDC-0941, GSK1120212, MK-2206, PD0325901, and Triciribine, and combinations thereof); iv) MM-151; v) an effective amount of an mTOR inhibitor (e.g., one or more of the mTOR inhibitors described in the appendix); and/or vi) an effective amount of trastuzumab or TMD1, and combinations thereof, in combination with an effective amount of an anti-ErbB3 agent, e.g., a bispecific anti-ErbB2/anti-ErbB3 antibody (e.g., the antibody comprising the amino acid sequence set forth in SEQ ID NO:1) and optionally an effective amount of trastuzumab or TMD1.

In one aspect, the combination of the bispecific anti-ErbB2/anti-ErbB3 antibody and either the effective amount of an anti-estrogen agent or the effective amount of the receptor tyrosine kinase inhibitor, and optionally the effective amount of trastuzumab or TMD1, is characterized as follows: when a first tissue culture medium is prepared comprising the bispecific anti-ErbB2/anti-ErbB3 antibody (e.g., the antibody comprising the amino acid sequence set forth in SEQ ID NO:1) at a first concentration and either the anti-estrogen agent at a second concentration or the receptor tyrosine kinase inhibitor (e.g., lapatinib) at a third concentration (wherein each concentration is the same or different as each other concentration), and the medium is contacted with cancer cells of a cell line in a cell culture, cell growth or cell proliferation or production of pErbB3 or production of pAKT in the cells is inhibited, or the percentage of cells in the culture that are apoptotic is increased. In certain aspects, cell growth or cell proliferation or production of pErbB3 or production of pAKT in the cells is inhibited, or the percentage of cells in the culture that are apoptotic is increased to a greater degree than cell growth, or cell proliferation or production of pErbB3 or production of pAKT in the cells is inhibited, or percentage of cells in the culture that are apoptotic is increased, to a lesser degree when cancer cells of the cell line in a cell culture are contacted with each of a second medium that is essentially the same as the first medium except that it does not comprise a bispecific anti-ErbB2/anti-ErbB3 antibody, and a third medium that is essentially the same as the first medium except that it does not comprise any anti-estrogen agent and it does not comprise any receptor tyrosine kinase inhibitor.

In another aspect, all effective amounts are either mouse effective amounts or human effective amounts. In another aspect, all effective amounts are mouse effective amounts and the combination of the bispecific anti-ErbB2/anti-ErbB3 antibody (optionally the antibody comprising the amino acid sequence set forth in SEQ ID NO:1) and either the effective amount of an anti-estrogen agent or the effective amount of the receptor tyrosine kinase inhibitor, is characterized as follows: when co-administered to BT474-M3 xenograft tumor bearing mice with a tumor of a measured volume, the combination is more effective at inhibiting tumor volume increase after 32 days of co-administration than is the mouse effective amount of the bispecific anti-ErbB2/anti-ErbB3 antibody administration without the co-administration of either the effective amount of an anti-estrogen agent or the effective amount of the receptor tyrosine kinase inhibitor. In another aspect, a mouse effective amount of trastuzumab or TMD1 is co-administered with the bispecific anti-ErbB2/anti-ErbB3 antibody.

In a second embodiment, a bispecific anti-ErbB2/anti-ErbB3 antibody (optionally the antibody comprising SEQ ID NO:1) is provided for use in combination therapy of a cancer (optionally a melanoma, clear cell sarcoma, head and neck, endometrial, prostate, breast, ovarian, gastric, colon, colorectal, lung, bladder, pancreatic, salivary gland, liver, skin, brain or renal tumor), where the combination therapy comprises concomitant use of an effective amount an agent selected from i) an effective amount of an anti-estrogen agent; ii) an effective amount of a receptor tyrosine kinase inhibitor; iii) an effective amount of a MEK/PI3 kinase/AKT inhibitor (e.g., those inhibitors described in the appendix and including, e.g., AZD6244, BKM-120, GDC-0941, GSK1120212, MK-2206, PD0325901, and Triciribine, and combinations thereof); iv) an effective amount of MM-151; v) an effective amount of an mTOR inhibitor (e.g., one or more of the mTOR inhibitors described in the appendix); and/or vi) an effective amount of trastuzumab or TMD1, and combinations thereof.

In a third embodiment, an aqueous solution is provided comprising a bispecific anti-ErbB2/anti-ErbB3 antibody (optionally the antibody comprising the amino acid sequence set forth in SEQ ID NO:1) at a first concentration and an agent selected from i) an effective amount of an anti-estrogen agent; ii) an effective amount of a receptor tyrosine kinase inhibitor; iii) an effective amount of a MEK/PI3 kinase/AKT inhibitor (e.g., those inhibitors described in the appendix and including, e.g., AZD6244, BKM-120, GDC-0941, GSK1120212, MK-2206, PD0325901, and Triciribine, and combinations thereof); iv) an effective amount of MM-151; v) an effective amount of an mTOR inhibitor (e.g., one or more of the mTOR inhibitors described in the appendix); and/or vi) an effective amount of trastuzumab or TMD1, and combinations thereof, at a second concentration. In certain aspects, when a first tissue culture medium is prepared comprising the bispecific anti-ErbB2/anti-ErbB3 antibody at the first concentration and the agent at the second concentration, and the medium is contacted with cancer cells of a cell line in a cell culture, cell growth or cell proliferation or production of pErbB3 or production of pAKT in the cells is inhibited, or percentage of cells in the culture that are apoptotic is increased. In certain aspects, cell growth or cell proliferation or production of pErbB3 or production of pAKT in the cells is inhibited, or the percentage of cells in the culture that are apoptotic is increased, to a lesser degree when cells of the cell line in a cell culture are contacted with a second tissue culture medium that is essentially the same as the first medium of except that it does not comprise the agent(s). In another aspect, cell growth or cell proliferation or production of pErbB3 or production of pAKT in the cells is inhibited, or the percentage of cells in the culture that are apoptotic is increased, to a lesser degree when cells of the cell line in a cell culture are contacted with a third tissue culture medium that is essentially the same as the first medium of except that it does not comprise any bispecific anti-ErbB2/anti-ErbB3 antibody.

In another aspect, the aqueous solution is blood plasma in a subject, and the subject does not experience a toxicity that is sufficiently harmful to require a change in a therapy being administered to the subject, which toxicity is mediated by a drug-drug interaction in the subject between the bispecific anti-ErbB2/anti-ErbB3 antibody and the anti-estrogen agent or the receptor tyrosine kinase inhibitor.

In another aspect, the aqueous solution further comprises trastuzumab or TMD1 at a third concentration, and the medium also comprises trastuzumab or TMD1 at the third concentration.

In another aspect, the method, combination therapy, or aqueous solution does not comprise an aromatase inhibitor or an estrogen receptor antagonist. In one embodiment the method, combination therapy, or aqueous solution comprises nab-paclitaxel.

In each embodiment and aspect thereof above, the anti-estrogen agent may be an estrogen receptor antagonist (e.g., fulvestrant or tamoxifen) or an aromatase inhibitor (e.g., wherein the aromatase inhibitor is letrozole, exemestane, anastrozole, aminoglutethimide, testolactone, vorozole, formestane, or fadrozole. Preferably the aromatase inhibitor is letrozole. Also in each embodiment and aspect thereof above, the receptor tyrosine kinase inhibitor is erlotinib, afatinib, dasatinib, gefitinib, imatinib, pazopinib, lapatinib, sunitinib, nilotinib or sorafenib. Preferably the receptor tyrosine kinase inhibitor is lapatinib. Also in each embodiment and aspect thereof above, the bispecific anti ErbB2/anti-ErbB3 antibody is the A5-HSA-ML3.9, ML3.9-HSA-A5, A5-HSA-B1D2, B1D2-HSA-A5, B12-HSA-B1D2, B1D2-HSA-B12, A5-HSA-F5B6H2, F5B6H2-HSA-A5, H3-HSA-F5B6H2, F5B6H2-HSA-H3, F4-HSA-F5B6H2, F5B6H2-HSA-F4, B1D2-HSA-H3, H3-HSA-B1D2, or the antibody comprising the amino acid sequence set forth in SEQ ID NO:1. Each embodiment and aspect thereof above may also further comprise use of capecitabine and/or cisplatin.

In each embodiment and aspect thereof above, one or more of a)-i) that follow may optionally apply: a) the cell line is BT474-M3; b) the culture is a spheroid culture, c) paclitaxel or another taxane or another chemotherapeutic drug is co-administered, optionally in accordance with the manufacturer's directions, d) the agent i)-vi) is administered in accordance with the manufacturer's directions, e) the trastuzumab or TMD1 is administered in accordance with the manufacturer's directions, f) the co-administration of the bispecific anti-ErbB2/anti-ErbB3 antibody with the agent g)-vi) produces an about additive or a superadditive effect, h) the bispecific anti-ErbB2/anti-ErbB3 antibody is the antibody comprising SEQ ID NO:1 and is administered in accordance with any of the regimens (e.g., modes, dosages, dosing intervals, loading and maintenance doses and dosing schemes) described in Examples 12 and 13, below, i) the lapatinib is administered in accordance with any of the regimens (e.g., modes, dosages, dosing intervals, loading and maintenance doses and dosing schemes) described in Example 16, below.

BRIEF DESCRIPTION OF THE DRAWINGS

FIG. 2 is seven graphs showing that MM-111 combines positively with anti-estrogen drugs in inhibiting estrogen-stimulated spheroid growth in vitro.

FIG. 3 is seven graphs showing that MM-111 combines positively with anti-estrogen drugs in inhibiting heregulin (HRG)-stimulated spheroid growth in vitro.

FIG. 4 is seven graphs showing that MM-111 combines positively with anti-estrogen drugs in inhibiting dual ligand (estrogen and heregulin)-stimulated spheroid growth in vitro.

FIG. 12 is three graphs showing that MM-111 combines positively with anti-estrogen drugs and lapatinib in inhibiting dual ligand (estrogen (E2) and heregulin (HRG))-stimulated spheroid growth in vitro.

FIG. 13 is four graphs showing the MM-111 combines positively with the aromatase inhibitor letrozole and the tyrosine kinase inhibitor lapatinib in heregulin (HRG) and androstenedione (A4)-stimulated BT474-M3-Aro cells that stably express human aromatase, which converts androstenedione to estrogen.

DETAILED DESCRIPTION

Figure 1:
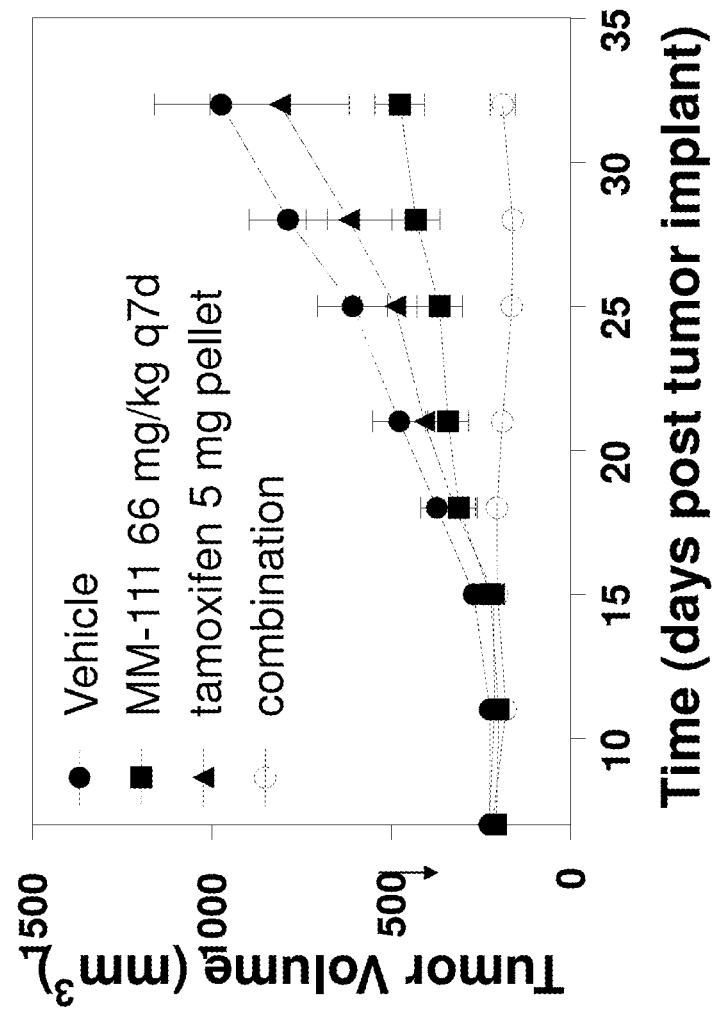
FIG. 1 is a graph showing that the combination of MM-111 and tamoxifen inhibits tumor growth in vivo better than either MM-111 or tamoxifen does alone. The x-axis shows time post tumor implant in days and the y-axis shows tumor volume in $mm^3$ Mice were treated with inhibitors beginning on day 7 post BT474-M3 cell implant.

As herein provided, bispecific anti-ErbB2/anti-ErbB3 antibodies (e.g., MM-111) are co-administered with one or more additional therapeutic agents (e.g. an aromatase inhibitor or tyrosine kinase inhibitor), to provide effective treatment to human patients having a cancer.

The term "anti-ErbB3 agent" refers to any therapeutic agent that binds to ErbB3 or binds to an ErbB3-specific ligand or blocks the expression of ErbB3, and thereby inhibits the activity of cellular signaling mediated by ErbB3. Non-limiting examples of types of anti-ErbB3 agents include antibodies, bispecific antibodies, ligand analogs, soluble forms of ErbB3 or the ErbB3 ectodomain, ErbB3 specific RNAi molecules, and similar biologic agents.

The term "antibody" describes a polypeptide comprising at least one antibody-derived antigen binding site (e.g., $V_H/V_L$ region or Fv, or complementarity determining region—CDR) that specifically binds to a specific antigen, e.g., ErbB3. "Antibodies" include whole antibodies and any antigen binding fragment, e.g., Fab or Fv, or a single chain fragment (e.g., scFv), as well as bispecific antibodies and similar engineered variants, human antibodies, humanized antibodies, chimeric antibodies Fabs, Fab'2s, ScFvs, SMIPs, Affibodies®, nanobodies, or a domain antibodies, and may be of any of the following isotypes: IgG1, IgG2, IgG3, IgG4, IgM, IgA1, IgA2, IgAsec, IgD, and IgE. The antibody may be a naturally occurring antibody or may be an antibody that has been altered (e.g., by mutation, deletion, substitution, conjugation to a non-antibody moiety). For example, an antibody may include one or more variant amino acids (compared to a naturally occurring antibody) which change a property (e.g., a functional property) of the antibody. For example, numerous such alterations are known in the art which affect, e.g., half-life, effector function, and/or immune responses to the antibody in a patient. The term "antibody" thus includes whole antibodies and any antigen binding fragment (i.e., "antigen-binding portion," e.g., Fabs) or single chains thereof (e.g., scFvs) as well as bispecific antibodies and similar engineered variants, provided that they retain the binding specificity of an antibody.

An "anti-ErbB3 antibody" is an antibody that immunospecifically binds to the ectodomain of ErbB3 and an "anti-ErbB2 antibody" is an antibody that immunospecifically binds to the ectodomain of ErbB2. The antibody may be an isolated antibody. Such binding to ErbB3 or ErB2 exhibits a Kd with a value of no greater than 50 nM as measured by a surface plasmon resonance assay or a cell binding assay. Exemplary anti-ErbB3 antibodies inhibit EGF-like ligand mediated phosphorylation of ErbB3, e.g., anti-ErbB2 antibodies that inhibit the binding of heregulin to ErbB2/ErbB3 heterodimers. EGF-like ligands include EGF, TGFα, betacellulin, heparin-binding epidermal growth factor, biregulin, epigen, epiregulin, and amphiregulin, which typically bind to ErbB1 and induce heterodimerization of ErbB1 with ErbB3.

The term "bispecific antibody" as used herein refers to a protein comprising two antigen-binding sites, a first binding site exhibiting immunospecific binding to a first antigen or epitope and a second binding site exhibiting immunospecific binding to a second antigen or epitope distinct from the first. An "anti-ErbB2/anti-ErbB3 bispecific antibody" is an antibody that comprises two binding sites, one that immunospecifically binds to the ectodomain of ErbB3 and another that immunospecifically binds to the ectodomain of ErbB2. Preferably, a bispecific ErbB3, ErbB2 antibody is the antibody comprising SEQ ID NO:1.

An "anti-estrogen agent" as used herein refers to an agent that prevents or reduces production of estrogen or prevents or reduces signaling mediated by estrogen receptors. Anti-estrogen agents include but are not limited to estrogen receptor antagonists and aromatase inhibitors. Estrogen receptor antagonists include but are not limited to raloxifene, fulvestrant, tamoxifen, afimoxifene (4-hydoroxytamoxifen), arzoxifene, toremifene, and lasofoxone. Preferably, the estrogen receptor antagonist is tamoxifen or fulvestrant. Aromatase inhibitors work by blocking the synthesis of estrogen in an animal (e.g., a mouse or a human). This lowers estrogen levels in the animal and thereby inhibits the growth of estrogen-driven cancers. Examples of aromatase inhibitors include but are not limited to exemestane, anastrozole, letrozole, aminoglutethimide, testolactone, vorozole, formestane, and fadrozole. Preferably, the aromatase inhibitor is exemestane or letrozole.

By "cancer" is meant any condition characterized by abnormal, unregulated, malignant cell growth.

By "malignant tumor" is meant any cancer that takes the form of a tumor.

The term "effective amount" refers to an amount of a drug effective to achieve a desired effect, e.g., to ameliorate disease in a subject. Where the disease is a cancer, the effective amount of the drug may inhibit (e.g., slow to some extent, inhibit or stop) one or more of the following characteristics: cancer cell growth, cancer cell proliferation, cancer cell motility, cancer cell infiltration into peripheral organs, tumor metastasis, and tumor growth. Where the disease is a cancer, the effective amount of the drug may alternately do one or more of the following when administered to a subject: slow or stop tumor growth, reduce tumor size (e.g., volume or mass); relieve to some extent one or more of the symptoms associated with the cancer, extend progression free survival, result in an objective response (including a partial response or a complete response), and increase overall survival time. To the extent the drug may prevent growth and/or kill existing cancer cells, it is cytostatic and/or cytotoxic.

A "mouse effective amount" refers to an amount of a drug effective to achieve a desired effect when the subject is a mouse.

A "human effective amount" refers to an amount of a drug effective to achieve a desired effect when the subject is a human patient.

The terms "combination therapy," "concomitant use," "co-administration," co-administering," "co-administered," and the like, refer to the administration of at least two therapeutic agents to a subject either simultaneously or within a time period during which the effects of the earlier-administered therapeutic agent are still operative in the subject when a later-administered therapeutic agent is administered.

A "receptor tyrosine kinase inhibitor" as used herein refers to a member of a class of drugs that specifically inhibit receptor tyrosine kinases and thus reduce or eliminate the activation of various signal transduction pathways. Receptor tyrosine kinase inhibitors useful for the treatment of cancer as disclosed herein include but are not limited to the small molecule inhibitors erlotinib, afatinib, dasatinib, gefitinib, imatinib, pazopinib, lapatinib, sunitinib, nilotinib and sorafenib. Receptor tyrosine kinase inhibitors also include antibody-based therapeutics such as cetuximab, panitumumab, zalutumumab, nimotuzumab, and matuzumab). Preferably, the receptor tyrosine kinase inhibitor is lapatinib.

"Dosage" or "dosing regimen" refers to parameters for administering a drug in defined quantities per unit time (e.g., per hour, per day, per week, per month, etc.) to a patient. Such parameters include, e.g., the size of each dose. Such parameters also include the configuration of each dose, which may be administered as one or more units, e.g., taken at a single administration, e.g., orally (e.g., as one, two, three or more pills, capsules, etc.) or injected (e.g., as a bolus). Dosage sizes may also relate to doses that are administered continuously (e.g., as an intravenous infusion over a period of minutes or hours). Such parameters further include frequency of administration of separate doses, which frequency may change over time. A "dosing cycle" or "dosing interval" is the period of time that comprises one cycle of treatment (e.g., 21 days or 28 days) for a dosing regimen.

"Dose" refers to an amount of a drug given in a single administration.

Preferred cancer cells of cell lines are cells of ErbB2 expressing cell lines such as ErbB2 overexpressing cell lines, e.g., BT474-M3 (ATCC® #CRL-HTB-20™, derived from breast ductal carcinoma cells), BT474-M3-Aro (BT474-M3 cells that stably express human aromatase), ZR75-30 (ATCC® # CRL1504™, derived from breast ductal carcinoma cells), SKOV-3 (ATCC® #HTB-77™, derived from metastatic ovarian adenocarcinoma cells), MCF7 (ATCC® #HTB-22™) clone 18, MDA-MB-453 (ATCC® #HTB-131™, derived from breast carcinoma cells), SK-BR-3 (ATCC® #HTB-30™, derived from breast adenocarcinoma cells), and NCI-N87 (ATCC® #CRL-5822™, derived from gastric carcinoma cells).

Cancers may include, for example, solid tumors such as: sarcomas (e.g., clear cell sarcoma), carcinomas (e.g., renal cell carcinoma), and lymphomas; tumors of the breast, colon, rectum, lung, oropharynx, hypopharynx, esophagus, stomach, pancreas, liver, bilecyst, bile duct, small intestine, urinary system (including the kidney, bladder, and epithelium of the urinary tract), female genital system (including the uterine neck, uterus, ovary, chorioma, and gestational trophoblast), male genital system (including the prostate, seminal vesicle, and testicles), endocrine glands (including the thyroid gland, adrenal gland, and pituitary body), skin (including angioma, melanoma, sarcoma originating from bone or soft tissue, and Kaposi's sarcoma), brain and meninges (including astrocytoma, neuroastrocytoma, spongioblastoma, retinoblastoma, neuroma, neuroblastoma, neurinoma and neuroblastoma), nerves, and eyes.

A cancer may be an estrogen receptor positive (ER+) cancer. Such cancers exemplify candidates for therapy regimens that include anti-estrogen agents. Such cancers may include but are not limited to certain breast, ovarian, uterine, endometrial, lung, bone, brain, bladder, liver and urogenital cancers.

A cancer may be an ErbB2 gene-amplified cancer and/or an ErbB2-expressing or overexpressing cancer. ErbB2, also known as HER2 or Neu, is a cell surface transmembrane receptor protein that generates intracellular signals (e.g., upon ligand activation) via its intracellular tyrosine kinase activity. In excess, such signals can promote oncogenesis e.g., by triggering cell division. The ErbB2 gene is amplified and/or overexpressed in many types of human malignancies, including but not limited to breast, ovarian, endometrial, pancreatic, colorectal, prostate, salivary gland, kidney, and lung. ErbB2 overexpressing cancers are designated a HER2$^{+++}$ or HER2$^{++}$ depending on the level of ErbB2 overexpression, with HER2$^{+++}$ indicating the highest levels of HER2 expression. HER2$^{+++}$ and HER2$^{++}$ status are typically determined by an immunoassay such as immunohistochemistry, e.g., Herceptest®. ErbB2 gene amplification is may be determined by, e.g., FISH (fluorescence in situ hybridization), with HER2-amplified cancer cells being those that have more than two HER2 gene copies being HER2-amplified, and cells and/or tumors comprising HER2-amplified cancer cells being referred to as "FISH positive."

A number of bispecific anti-ErbB2, antiErbB3 antibodies that are scFv HSA conjugates are described in co-pending US patent publication No. 2011-0059076, and PCT publication Nos. WO2009/126920 and WO 2010/059315, each of which is incorporated herein by reference in its entirety and each of which discloses MM-111 (also referred to as B2B3-1) and other bispecific anti-ErbB2/antiErbB3 antibodies that are scFv HSA conjugates and that are suitable for use in the methods and compositions provided herein, including the components of A5-HSA-ML3.9, ML3.9-HSA-A5, A5-HSA-B1D2, B1D2-HSA-A5, B12-HSA-B1D2, B1D2-HSA-B12, A5-HSA-F5B6H2, F5B6H2-HSA-A5, H3-HSA-F5B6H2, F5B6H2-HSA-H3, F4-HSA-F5B6H2, F5B6H2-HSA-F4, B1D2-HSA-H3, and H3-HSA-B1D2. Other suitable bispecific anti-ErbB2/antiErbB3 antibodies are disclosed and claimed in U.S. Pat. Nos. 7,332,580 and 7,332,585, which are incorporated herein by reference. MM-111 is currently undergoing clinical trials, including an open-label Phase 1/2 and pharmacologic study of MM-111 in patients with advanced, refractory HER2 positive cancers, an open-label Phase 1/2 trial of MM-111 in combination with trastuzumab (Herceptin®) in patients with advanced HER2 positive breast cancer, and an open label, Phase 1/2 and pharmacologic study of MM-111 with three different combination treatments: MM-111 in combination with cisplatin, capecitabine, and trastuzumab, MM-111 in combination with lapatinib and trastuzumab, and MM-111 in combination with paclitaxel and trastuzumab.

A bispecific anti-ErbB2/anti-ErbB3 antibody (e.g., MM-111) can be co-administered with other therapeutic agents, (e.g, an anti-estrogen receptor agent or a receptor tyrosine kinase inhibitor) prior to (e.g., neoadjuvant therapy), concurrent with, or following (e.g., adjuvant therapy) radiotherapy of, or surgical intervention to remove, a malignant tumor.

Additional therapeutic agents suitable for combination with anti-ErbB2/anti-ErbB3 antibodies may further include: 1) antibody EGFR inhibitors (e.g. MM-151, Sym004, cetuximab, panitumumab, zalutumumab, nimotuzumab, and matuzumab), additional small molecule tyrosine kinase inhibitors such as PKI-166, PD-158780, EKB-569, Tyrphostin AG 1478, and pan-HER kinase inhibitors (e.g. CI-1033 (PD 183805), AC480, HM781-36B, AZD8931 and PF299804); 2) microtubule stabilizing agents (e.g. laulimalide, epothilone A, epothilone B, discodermolide, eleutherobin, sarcodictyin A, sarcodictyin B, paclitaxel, nab-paclitaxel or docetaxel); antimetabolites such as 5-fluorouracil (5-FU) and capecitabine; and platinum-based therapeutics such as oxaliplatin, carboplatin and cisplatin. Additional examples of therapeutic agents suitable for combination with anti-ErbB2/anti-ErbB3 antibodies may be found in Table 5 and the Appendix below.

MM-111 is suitable for both large scale production and systemic therapy. MM-111 binds to ErbB2/ErbB3 heterodimers and forms a trimeric complex with ErbB2 and ErbB3, effectively inhibiting ErbB3 signaling. The antitumor activity of MM-111 requires the presence of both ErbB2 and ErbB3, but is particularly dependent on ErbB2 expression. The affinity of its ErbB2 antigen-binding site is about 30 times higher than the affinity of its ErbB3 antigen-binding site, but the ErbB2 antigen-binding site does not by itself inhibit ErbB2 activity when bound to ErbB2. The strong binding of MM-111 to ErbB2 places the ErbB3 antigen-binding site in close proximity to bound ErbB2/ErbB3 heterodimer, resulting in an avidity effect that potentiates the binding of the ErbB3 antigen-binding site to the heterodimer ErbB3, whereby a biological effect is produced. MM-111 is administered to human subjects (patients) at an interval measured in days, as a single loading dose of at least 20 mg/kg of MM-111 followed by at least seven day intervals (e.g., every 2 weeks) by at least one administration of a single maintenance dose of MM-111, where the maintenance dose is generally smaller than the loading dose, e.g., at least 5 mg/kg less than the loading dose.

EXAMPLES

The following examples are provided by way of illustration only and not by way of limitation. Those of skill in the art will readily recognize a variety of non-critical parameters that could be changed or modified to yield essentially the same or similar results.

MM-111 in Combination with Anti-estrogen Therapeutics

Methods:
Spheroid In Vitro Tumor Model Assay

BT474-M3 wild type cells (2000 cells/well) are plated in Ultra Low Cluster 96-well plate (Costar). After overnight incubation, indicated treatments are introduced to the plate. Cells are continued to culture for six days. Spheroids are then examined by Nikon microscope and analyzed by MetaMorph Image Analysis Software (Molecular Devices). The spheroid size from cells cultured in medium containing 10% FBS is set as control.

Xenograft Model

BT474-M3 cells ($2\times10^7$ cells per mice) are inoculated subcutaneously into Nu/Nu immunodeficient mice, which are implanted with an estrogen pellet (0.72 mg; 60-day release) one day before the experiment. Tumors are measured after seven days and mice are randomized into four groups: those treated with placebo, MM-111 (60 mg/kg, Q7D), 4-hydroxytamoxifen (5 mg; 60-day release pellet), and combination of MM-111 and 4-hydroxytamoxifen, respectively. Tumors are measured every three days and the experiment is ended at day 32.

Example 1

MM-111 and Tamoxifen Combination Therapy Inhibits Tumor Growth In Vivo

In order to compare the effect of MM-111 and tamoxifen combination therapy on tumor growth in vivo, estrogen stimulated mice were prepared in the xenograft model using the methods described above or minor variations thereof. Mice were inoculated with tumor forming BT474-M3 cells and on day 7 given a placebo (vehicle control), MM-111, tamoxifen, or a combination of MM-111 and tamoxifen and tumor growth was measured over time. As shown in FIG. 1, this in vivo BT474-M3 xenograft model showed resistance to tamoxifen treatment but when mice were given a combination of MM-111 and tamoxifen the combination treatment inhibited tumor growth to a significantly greater extent. Statistical significance ($p<0.05$) was observed for the combination group from day 28 onward when compared to vehicle control, from day 21 onward when compared to MM-111 and from day 25 onward when compared to tamoxifen.

Example 2

Figure 2A:
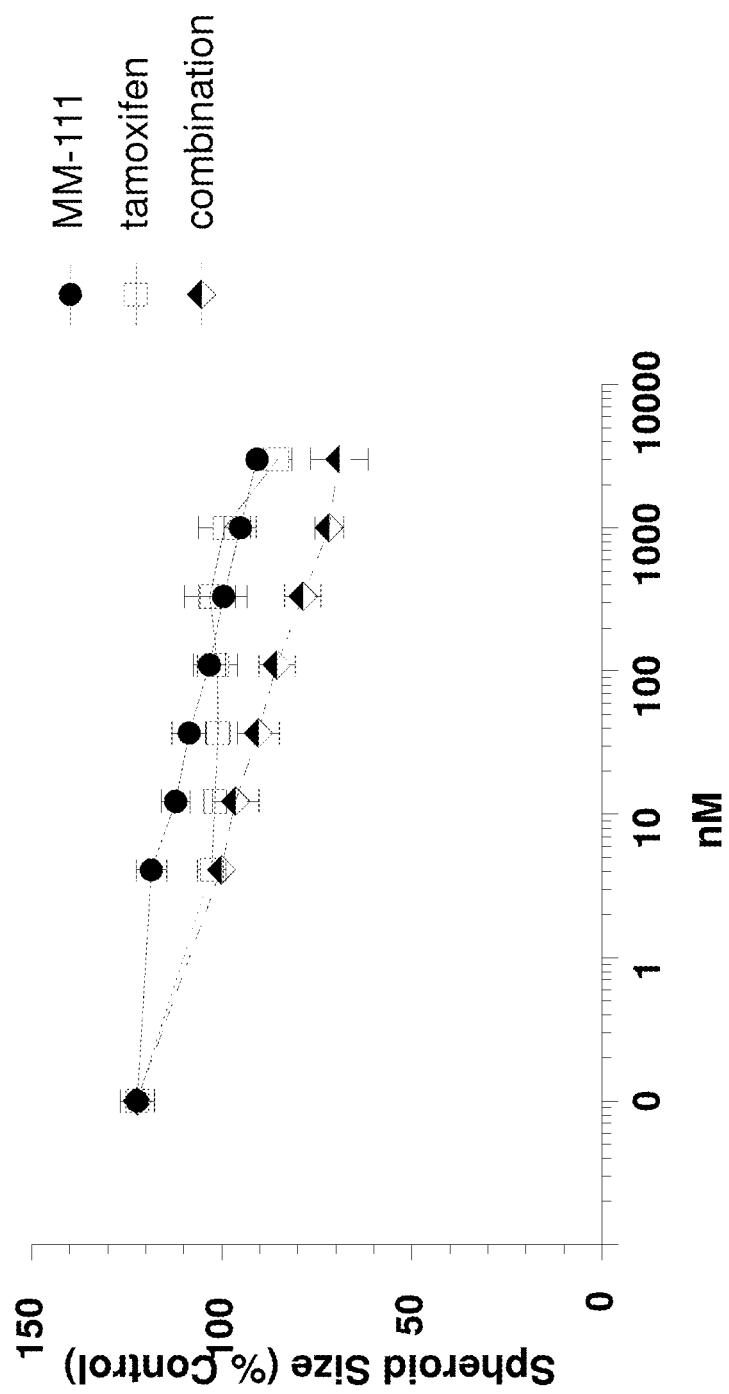
FIG. 2a shows the effect of MM-111, tamoxifen (4-hydroxytamoxifen or 4OHT), or MM-111 and tamoxifen on in vitro spheroid growth.
Figure 2B:
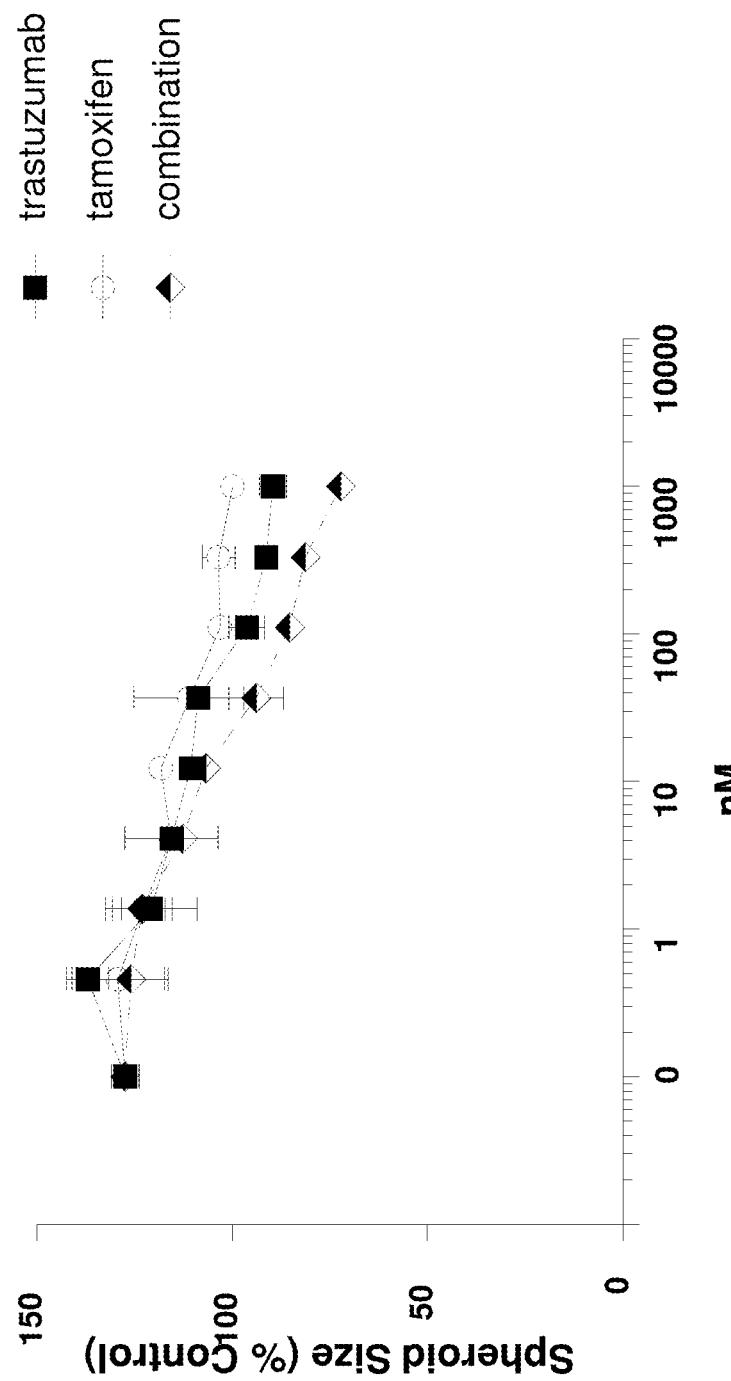
FIG. 2b shows the effect of trastuzumab, tamoxifen, or trastuzumab and tamoxifen.
Figure 2C:
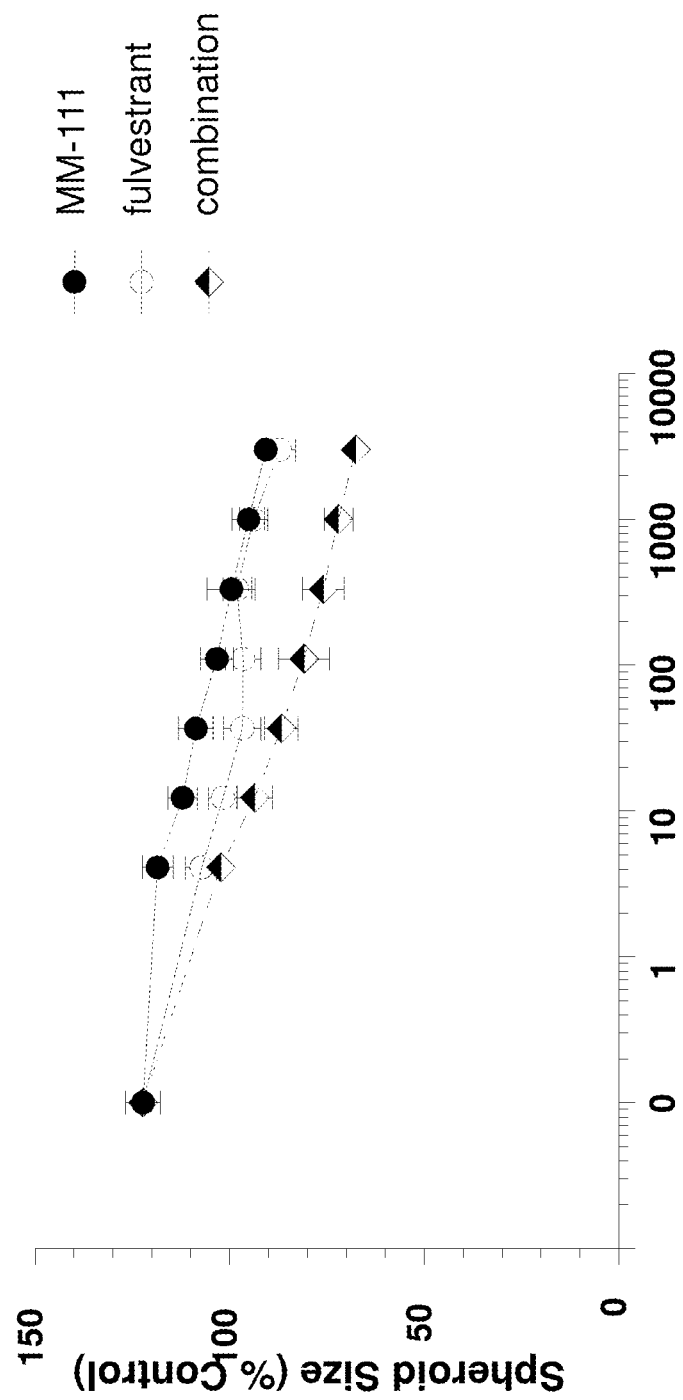
FIG. 2c shows the effect of MM-111, fulvestrant (FVT), or MM-111 and fulvestrant.
Figure 2D:
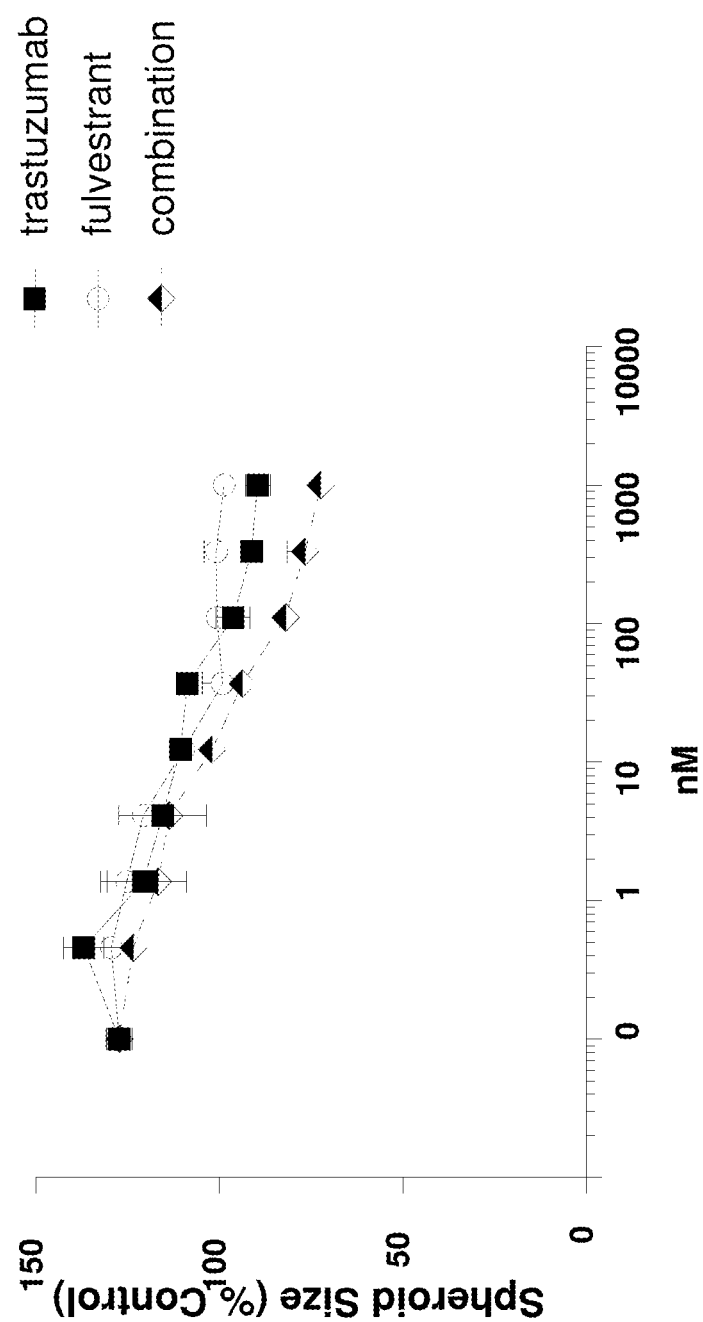
FIG. 2d shows the effect of trastuzumab, fulvestrant, or trastuzumab and fulvestrant.
Figure 2E:
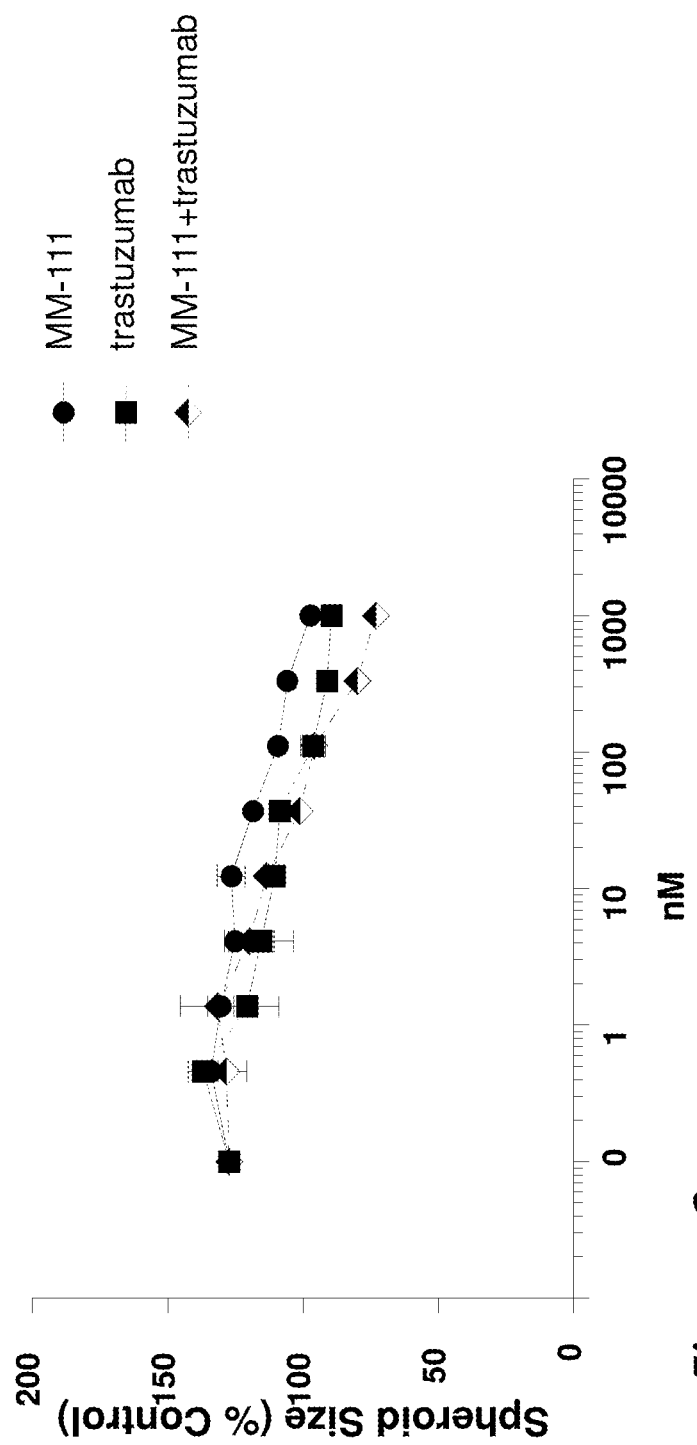
FIG. 2e shows the effect of MM-111, trastuzumab, or MM-111 and trastuzumab.
Figure 2F:
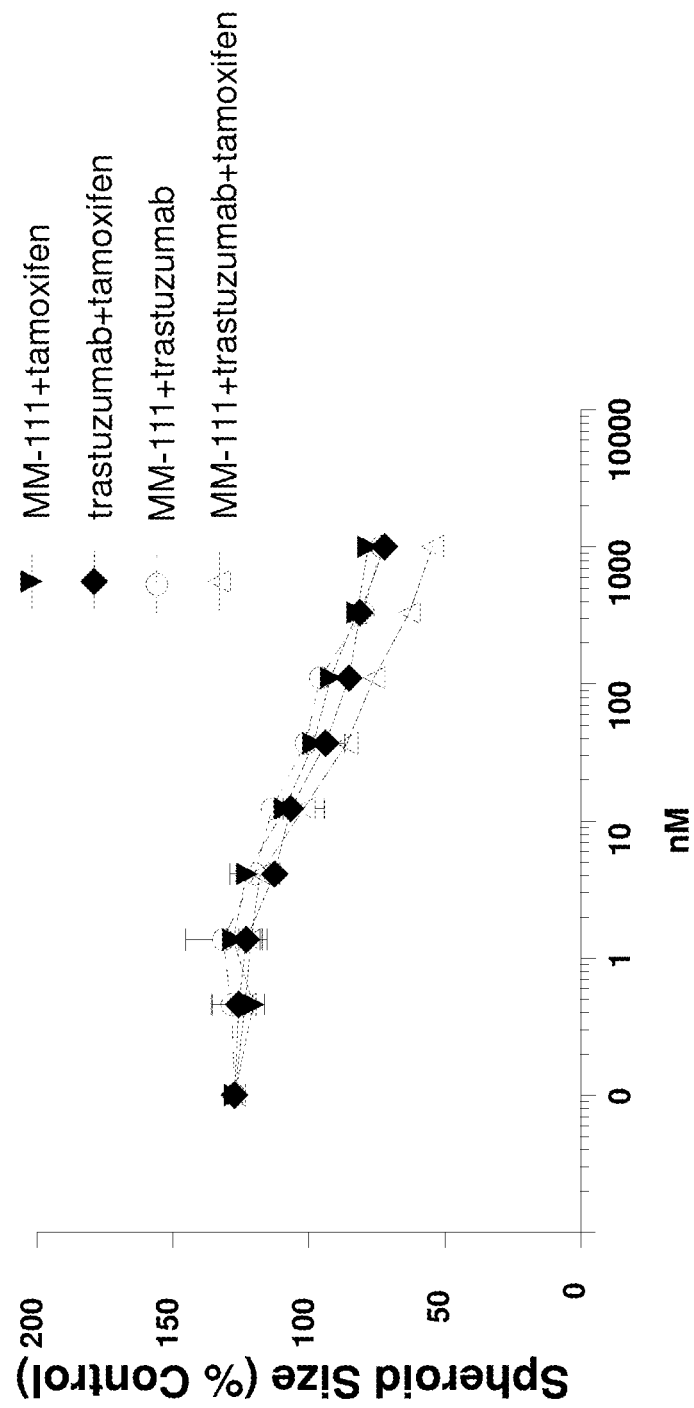
FIG. 2f shows the effect of MM-111, trastuzumab, and tamoxifen combined compared to that of any of the double combinations.
Figure 2G:
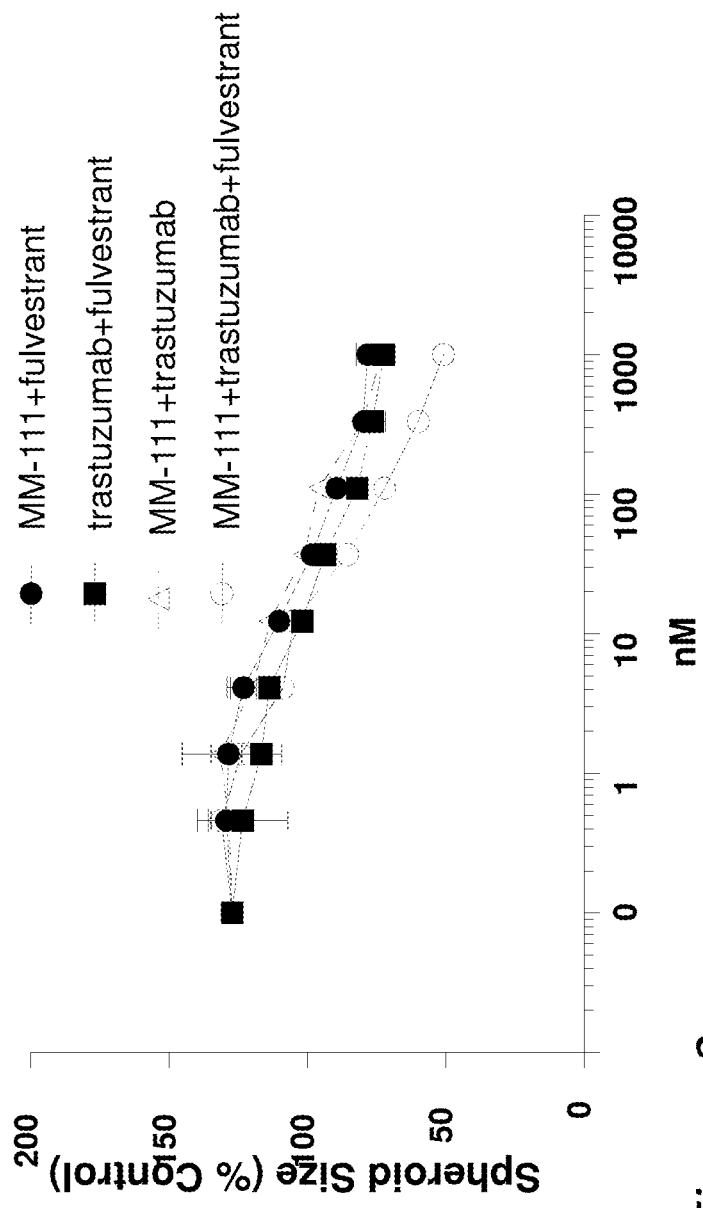
FIG. 2g shows the effect of MM-111, trastuzumab, and fulvestrant combined compared to that of any of the double combinations. The x-axes are a log scale of each drug concentration for each experimental condition in nM and the y axis is spheroid size as % of control spheroid size.

MM-111 Combines Positively with Anti-Estrogen Drugs in Inhibiting Estrogen-Stimulated Spheroid Growth Multicellular spheroids are used to simulate the growth and microenvironmental conditions of tumors in vitro. To further investigate the ability of MM-111 to inhibit cell growth when in combination with anti-estrogen drugs, spheroids of BT474-M3 cells were prepared using the methods described above or minor variations thereof and treated with an ErbB2-binding therapeutic and/or an anti-estrogen therapeutic. Spheroids of estrogen-stimulated cells were treated with a dose range of MM-111, tamoxifen, or the combination of MM-111 and tamoxifen (FIG. 2a); trastuzumab, tamoxifen or the combination of trastuzumab and tamoxifen (FIG. 2b); MM-111, fulvestrant, or the combination of MM-111 and fulvestrant (FIG. 2c); trastuzumab, fulvestrant, or the combination of trastuzumab and fulvestrant (FIG. 2d); or MM-111, trastuzumab, or the combination of MM-111 and trastuzumab (FIG. 2e). When used as single agent alone, MM-111, trastuzumab, fulvestrant and tamoxifen showed inhibitory effects on spheroid growth in the estrogen-stimulated BT474-M3 spheroid assay. The combination of tamoxifen or fulvestrant with MM-111 (FIGS. 2a and 2c, respectively) or trastuzumab (FIGS. 2b and 2d, respectively) increased the degree of growth inhibition, as did the combination of MM-111 and trastuzumab (FIG. 2e). The inhibitory effects were increased still further when estrogen-stimulated spheroids were treated with the triple combination of MM-111, trastuzumab, and tamoxifen (FIG. 20 or MM-111, trastuzumab, and fulvestrant (FIG. 2g) as compared to the double combinations of drugs.

Example 3

Figure 3A:
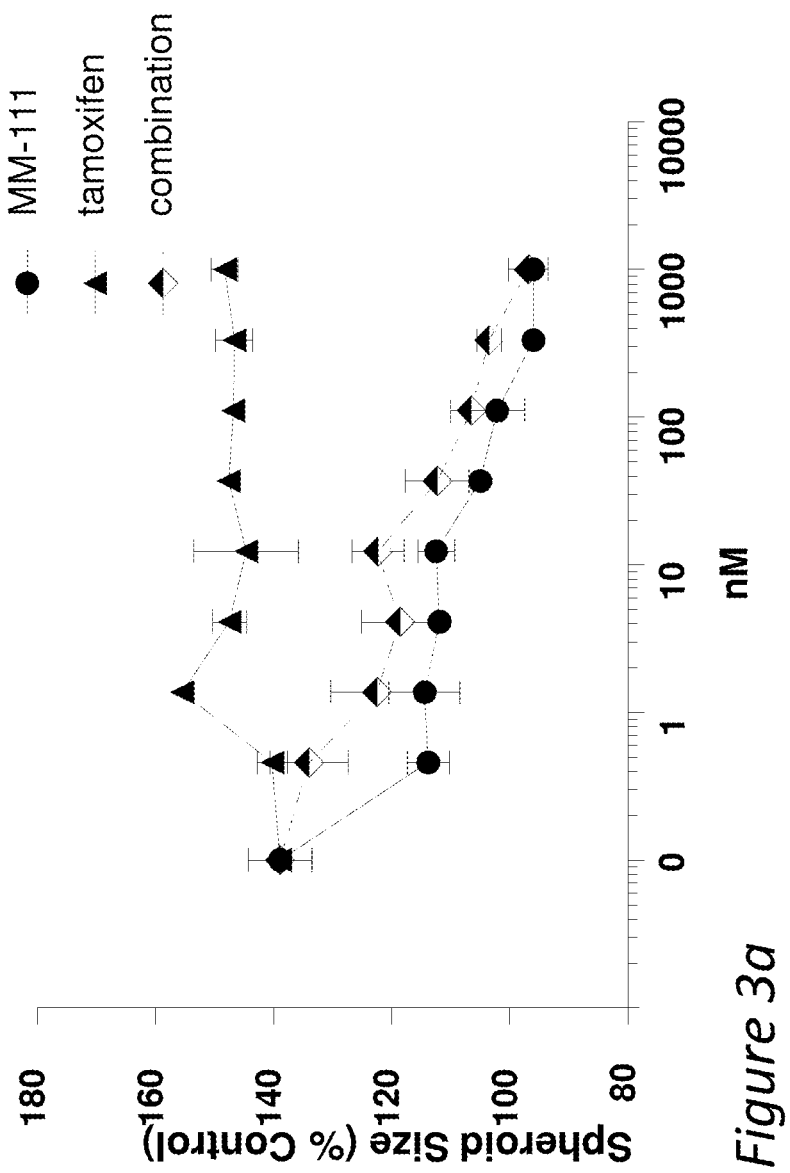
FIG. 3a shows the effect of MM-111, tamoxifen (4-hydroxytamoxifen or 4OHT), or MM-111 and tamoxifen.
Figure 3B:
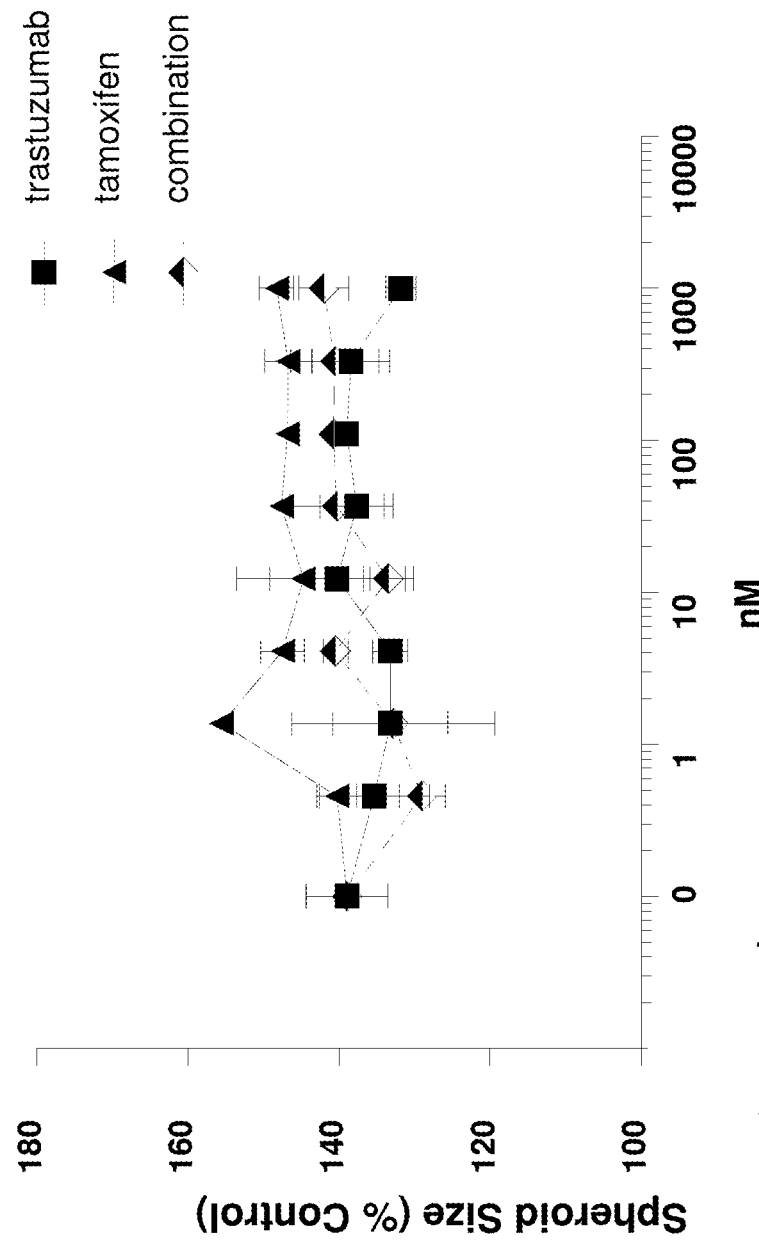
FIG. 3b shows the effect of trastuzumab, tamoxifen, or trastuzumab and tamoxifen.
Figure 3C:
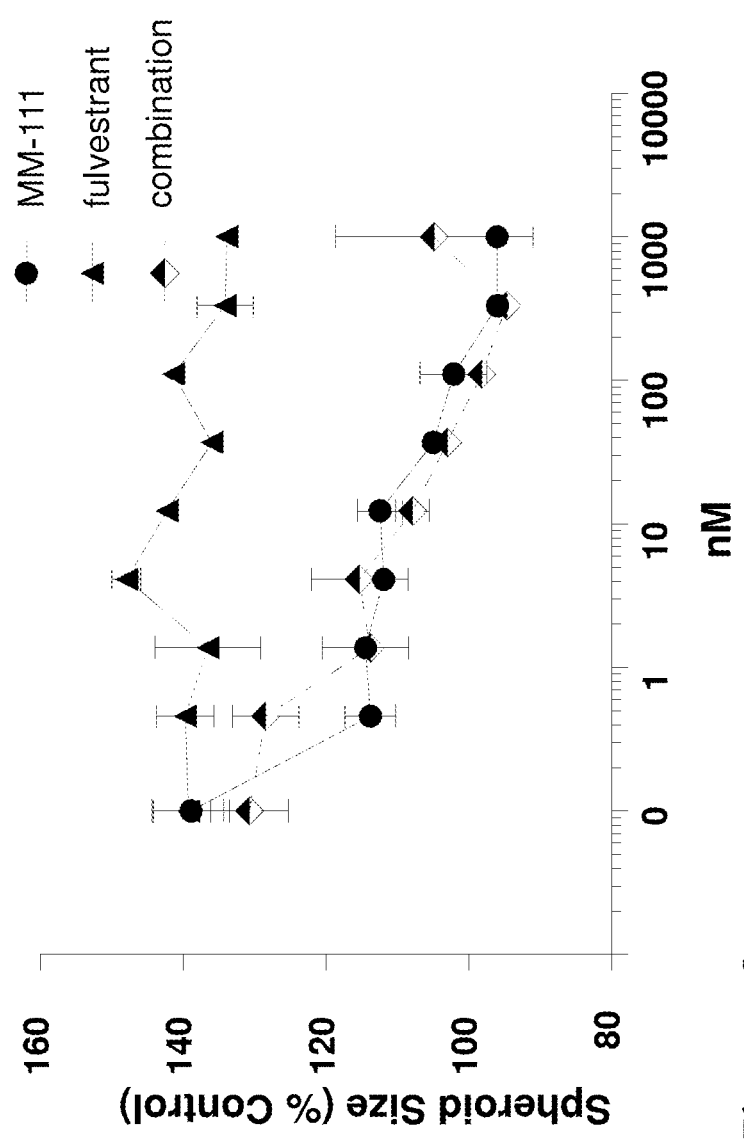
FIG. 3c shows the effect of MM-111, fulvestrant (FVT), or MM-111 and fulvestrant.
Figure 3D:
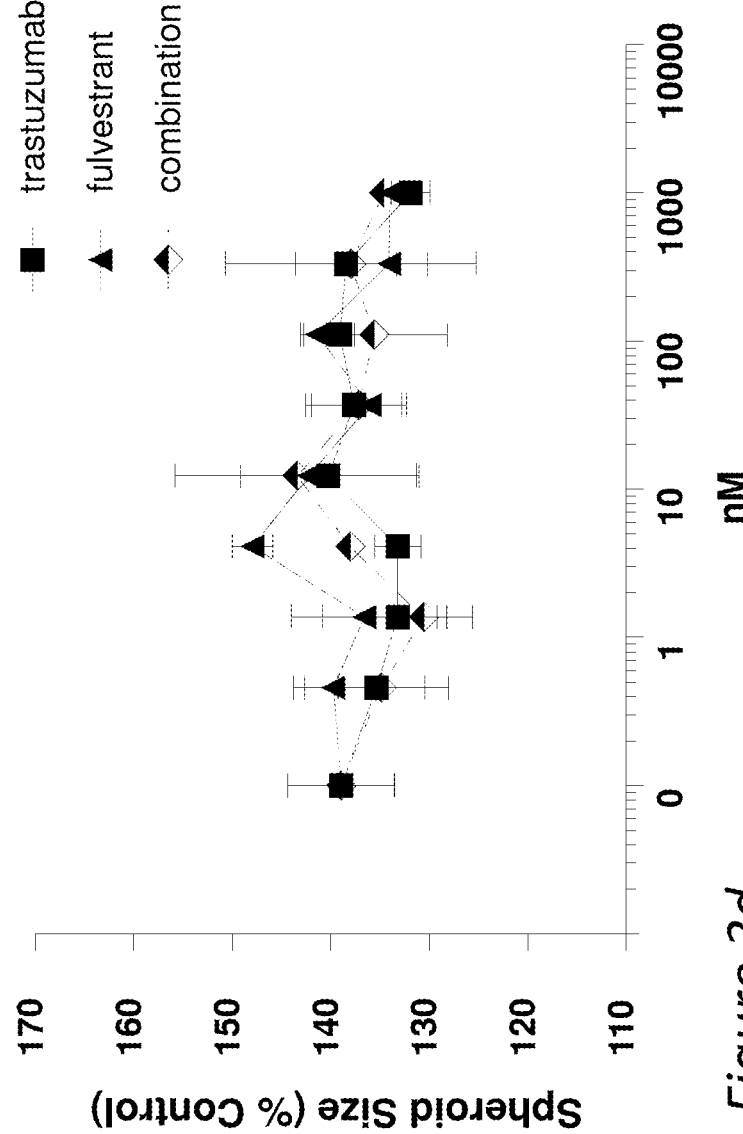
FIG. 3d shows the effect of trastuzumab, fulvestrant, or trastuzumab and fulvestrant.
Figure 3E:
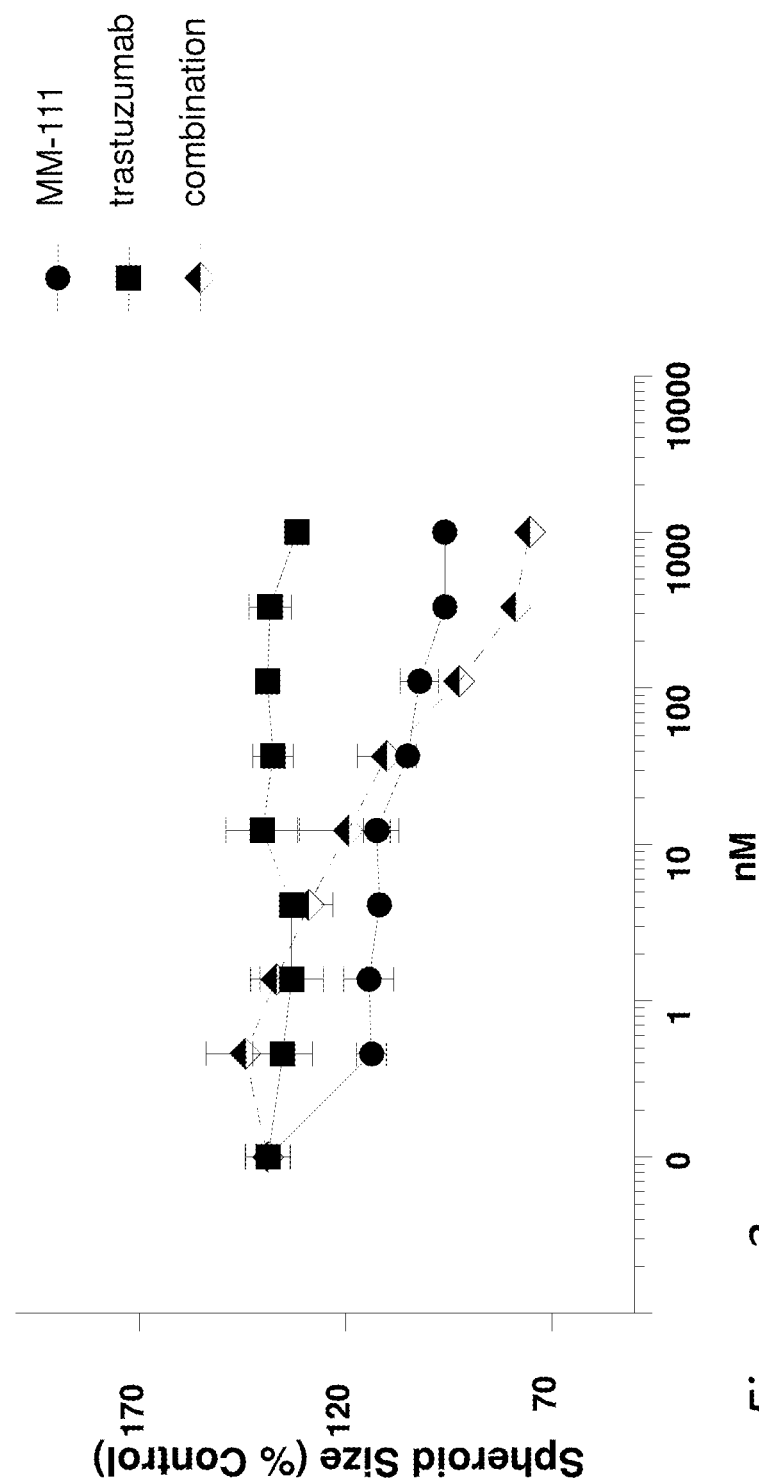
FIG. 3e shows the effect of MM-111, trastuzumab, or MM-111 and trastuzumab.
Figure 3F:
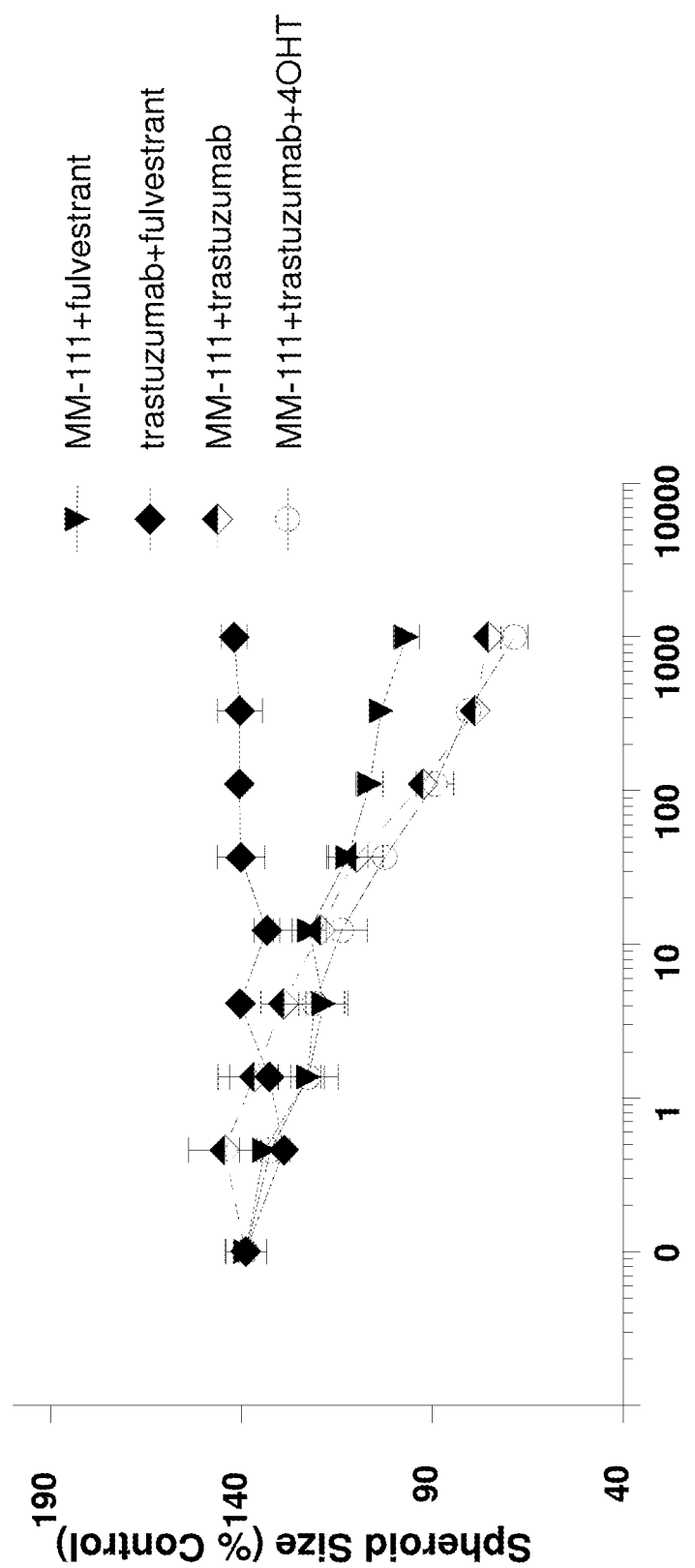
FIG. 3f shows the effect of MM-111, trastuzumab, and tamoxifen combined compared to that of any of the double combinations.
Figure 3G:
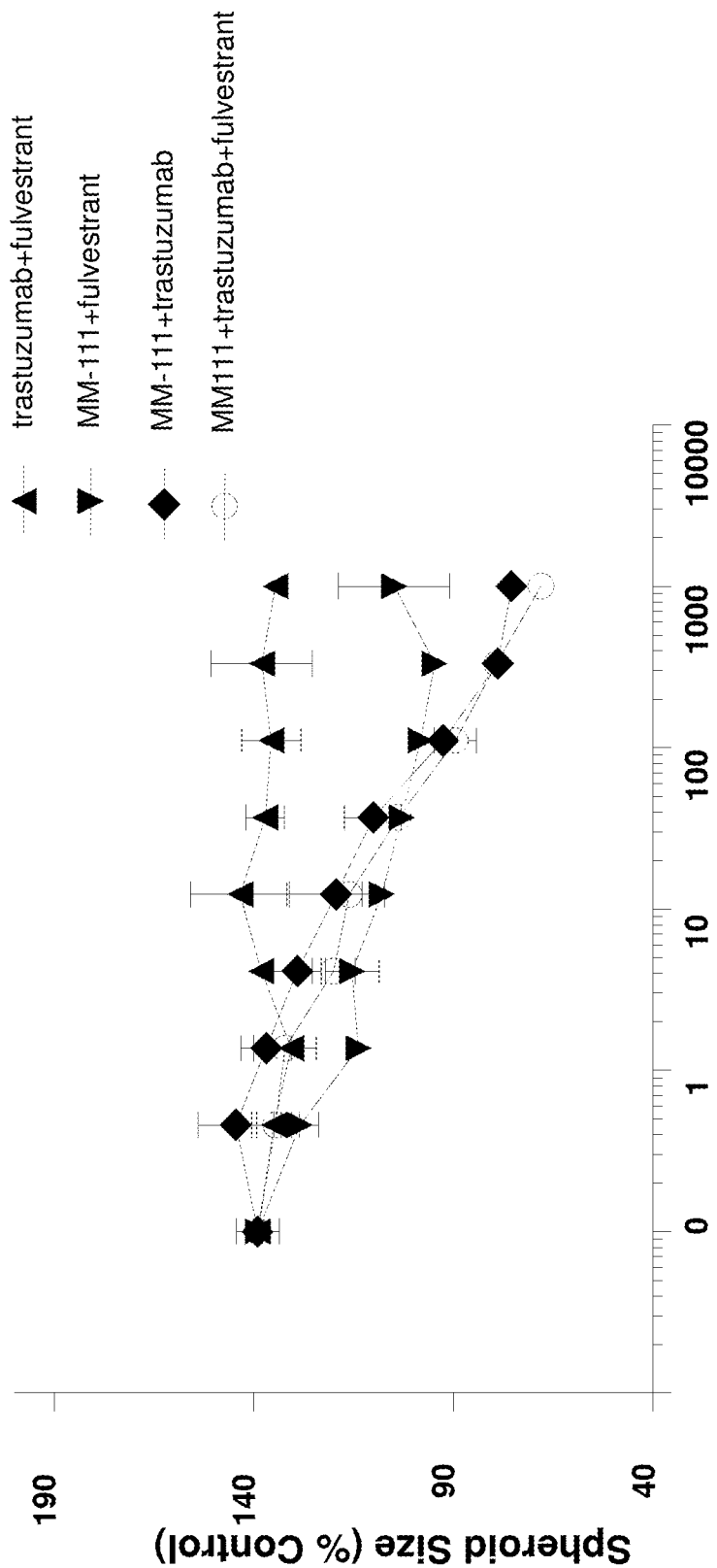
FIG. 3g shows the effect of MM-111, trastuzumab, and fulvestrant combined compared to that of any of the double combinations. The x-axes are a log scale of each drug concentration for each experimental condition in nM and the y axis is spheroid size as % of control spheroid size.

MM-111 Combines Positively with Anti-Estrogen Drugs in Inhibiting Heregulin-Stimulated Spheroid Growth To further investigate the ability of MM-111 to inhibit cell growth when in combination with anti-estrogen drugs, spheroids of heregulin (HRG)-stimulated BT474-M3 cells were prepared using the methods described above or minor variations thereof and treated with a dose range of MM-111, tamoxifen, or the combination of MM-111 and tamoxifen (FIG. 3a); trastuzumab, tamoxifen or the combination of trastuzumab and tamoxifen (FIG. 3b); MM-111, fulvestrant, or the combination of MM-111 and fulvestrant (FIG. 3c); trastuzumab, fulvestrant, or the combination of trastuzumab and fulvestrant (FIG. 3d); or MM-111, trastuzumab, or the combination of MM-111 and trastuzumab (FIG. 3e). MM-111 inhibited heregulin-induced spheroid growth but tamoxifen (FIG. 3a), trastuzumab (FIG. 3b), and fulvestrant (FIG. 3c) did not inhibit heregulin stimulated spheroid growth. No significant combinational effect was observed when MM-111 was used with tamoxifen (FIG. 3a) or fulvestrant (FIG. 3c). The combination of trastuzumab and either tamoxifen (FIG. 3b) or fulvestrant (FIG. 3d) failed to show inhibitory activity significantly greater than either drug alone. As shown in FIG. 3e, MM-111 but not trastuzumab showed inhibitory activity in heregulin-stimulated spheroid growth. Improved inhibitory effects were observed when both drugs were combined. In comparison to the double combination of either MM-111 or trastuzumab with tamoxifen or fulvestrant, the triple combination of MM-111, trastuzumab and either tamoxifen (FIG. 3f) or fulvestrant (FIG. 3g) showed similar inhibitory effects as those of MM-111 and trastuzumab in combination (FIG. 3e) on heregulin-stimulated spheroid growth.

Example 4

Figure 4A:
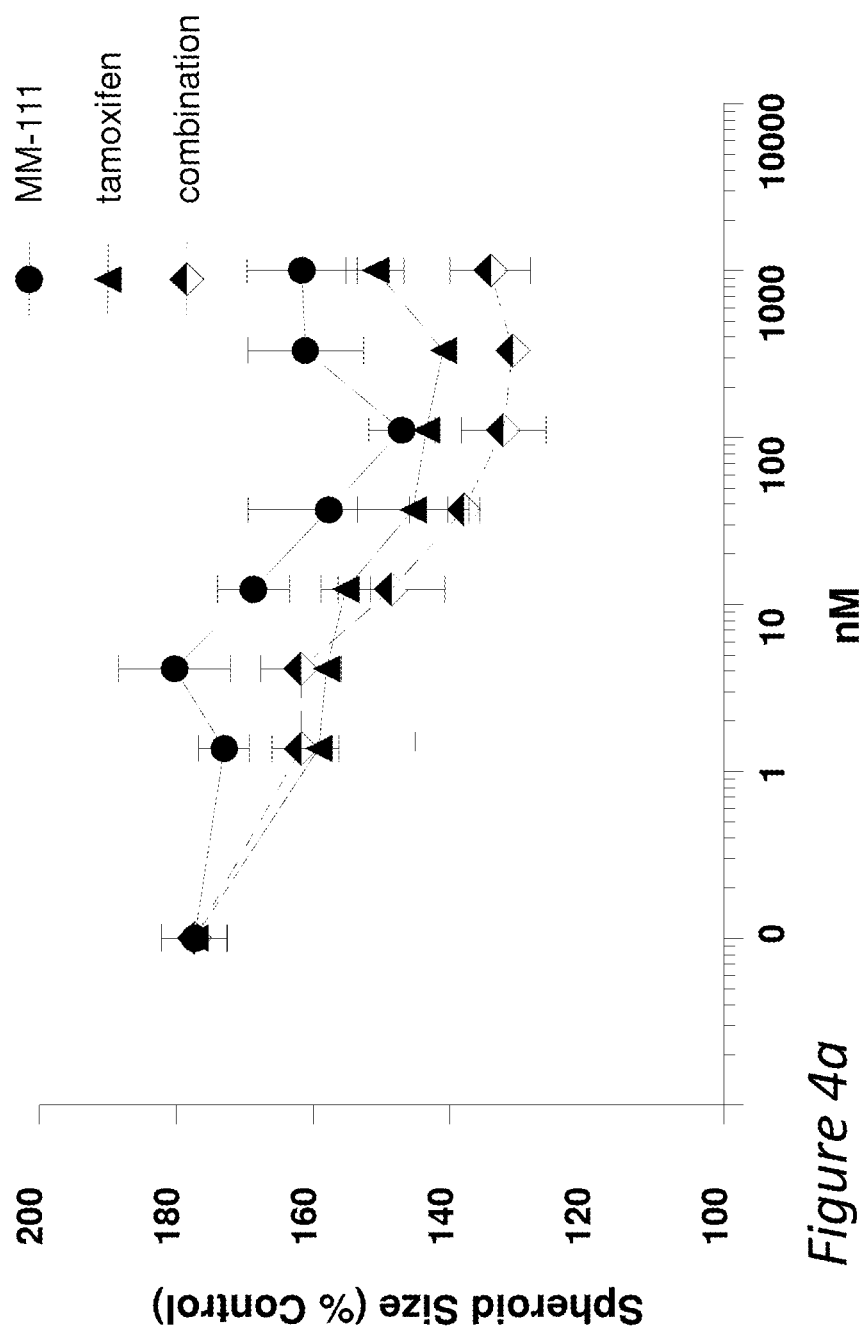
FIG. 4a shows the effect of MM-111, tamoxifen, or MM-111 and tamoxifen.
Figure 4B:
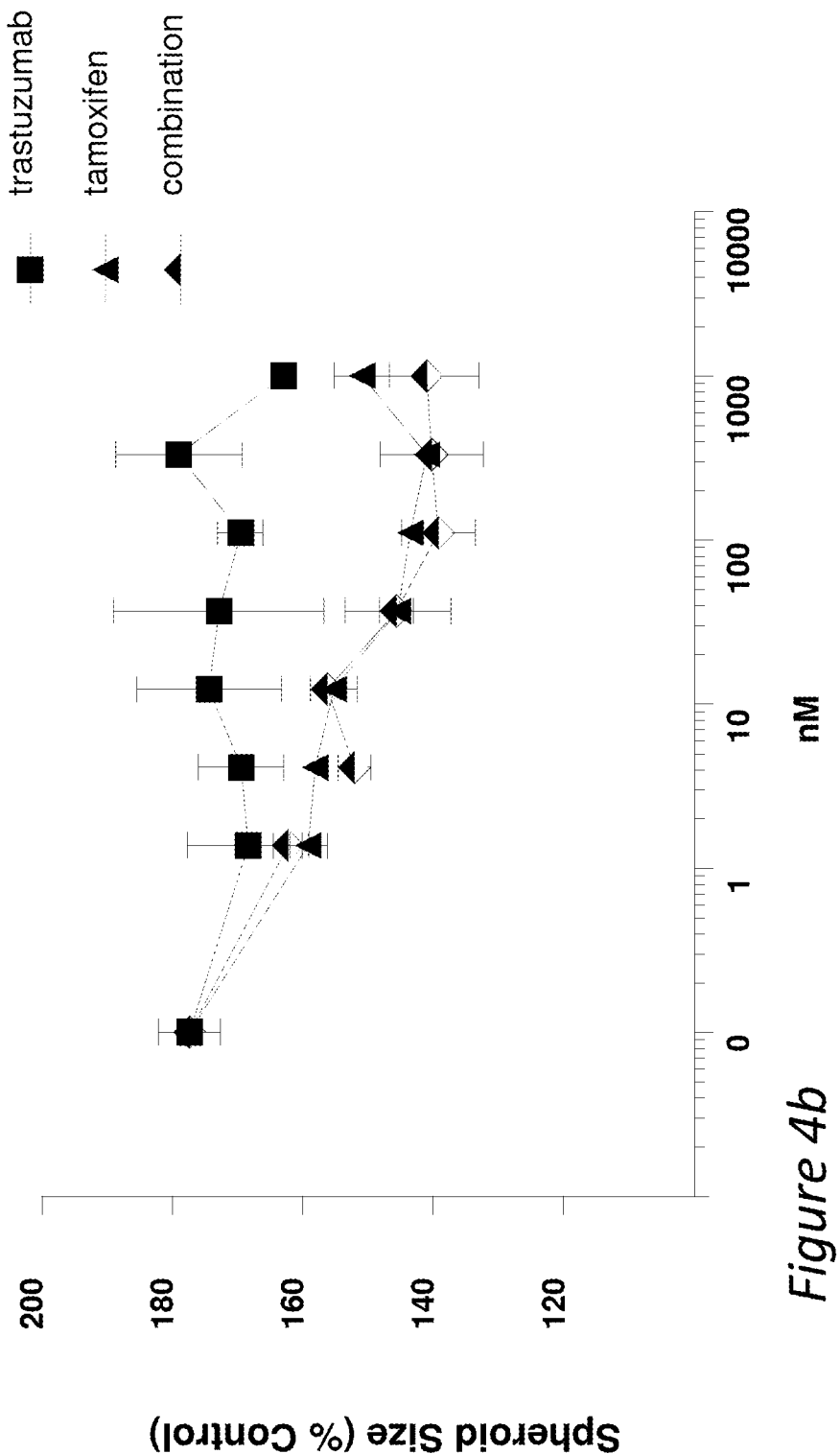
FIG. 4b shows the effect of trastuzumab, tamoxifen, or trastuzumab and tamoxifen.

MM-111 Combines Positively with Anti-Estrogen Drugs in Inhibiting Dual Ligand (Estrogen and Heregulin)-Stimulated Spheroid Growth Dual ligand (estrogen and heregulin) stimulated spheroids were treated with a dose range of tamoxifen, MM-111 or the combination of MM-111 and tamoxifen (FIG. 4a) or trastuzumab, tamoxifen or the combination of trastuzumab and tamoxifen (FIG. 4b). While MM-111 and trastuzumab each inhibited spheroid growth (FIG. 4a) the combination of MM-111 and tamoxifen showed greater inhibitory effects than either drug alone. In contrast, trastuzumab alone had no significant inhibitory effects and the combination of trastuzumab and tamoxifen showed similar effects to tamoxifen alone.

Figure 4C:
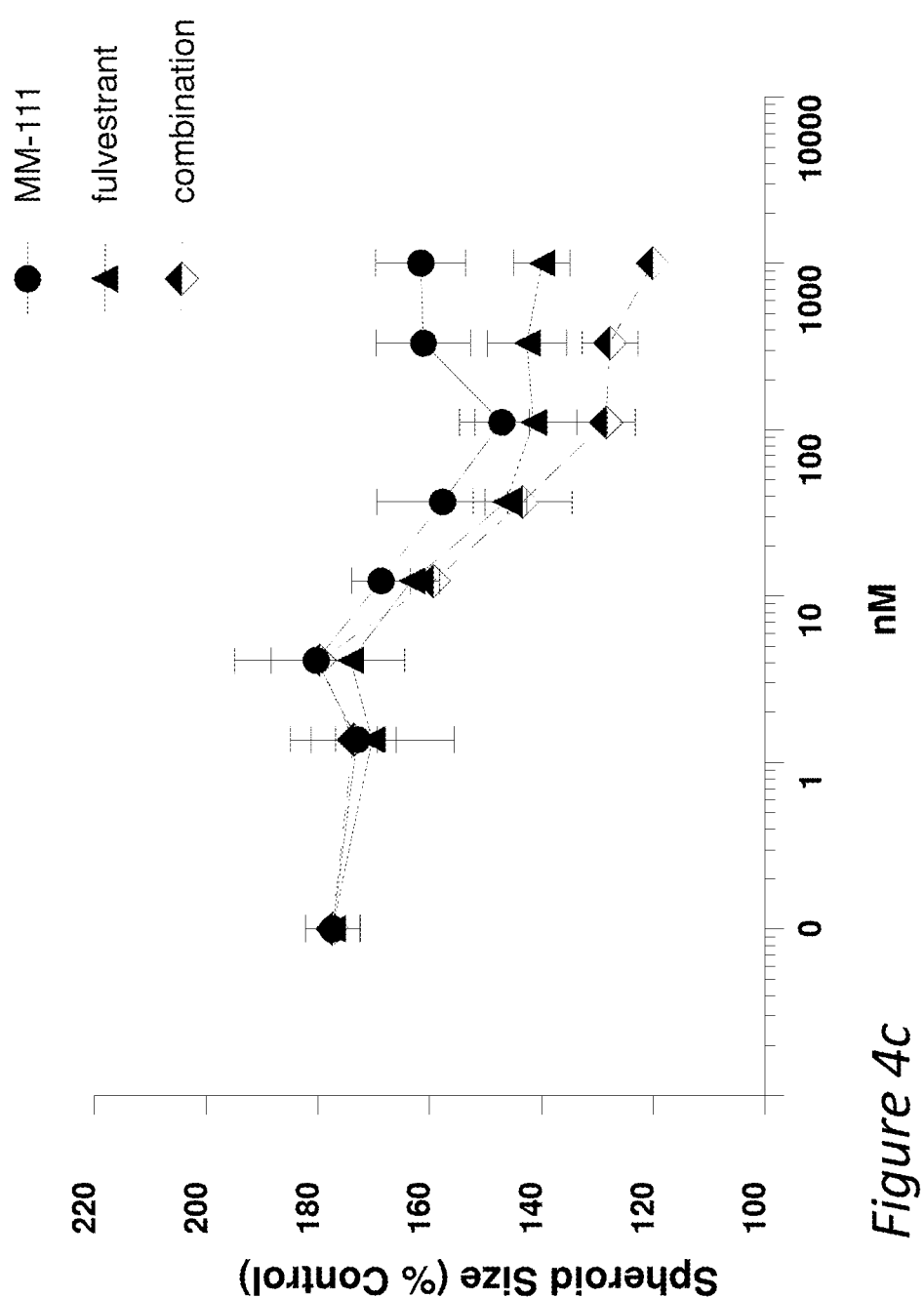
FIG. 4c shows the effect of MM-111, fulvestrant (FVT), or MM-111 and fulvestrant.
Figure 4D:
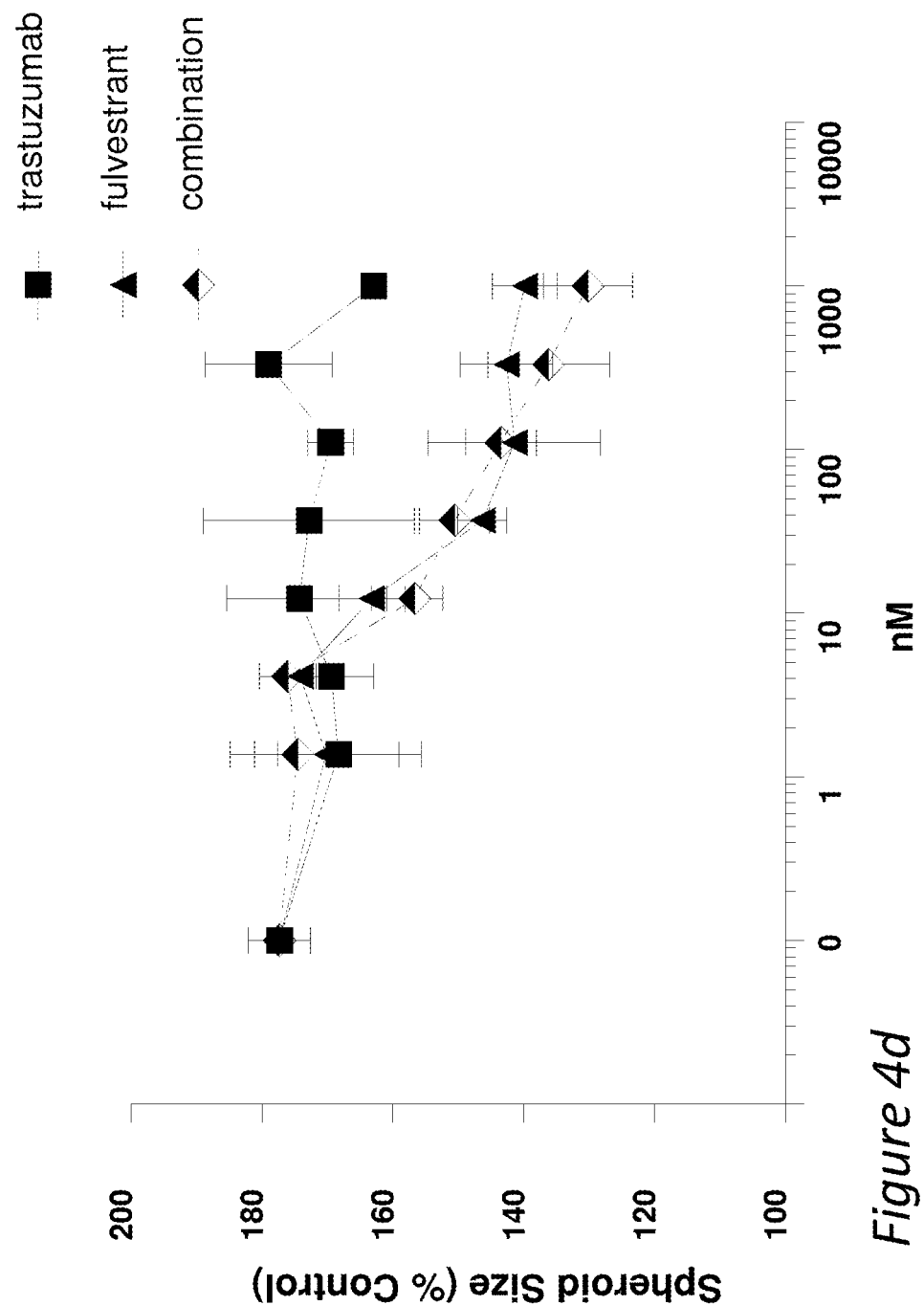
FIG. 4d shows the effect of trastuzumab, fulvestrant, or trastuzumab and fulvestrant.

Dual ligand stimulated spheroids were then treated with a dose range of fulvestrant, MM-111 or the combination of MM-111 and fulvestrant (FIG. 4c) or fulvestrant, trastuzumab, or a combination of fulvestrant or trastuzumab (FIG. 4d). Again, while MM-111 and fulvestrant each separately inhibited spheroid growth the combination of MM-111 and fulvestrant showed greater inhibitory effects than either drug alone (FIG. 4c). Trastuzumab alone had no significant inhibitory effects and the combination of trastuzumab and fulvestrant showed similar effects to tamoxifen alone (FIG. 4d).

Figure 4E:
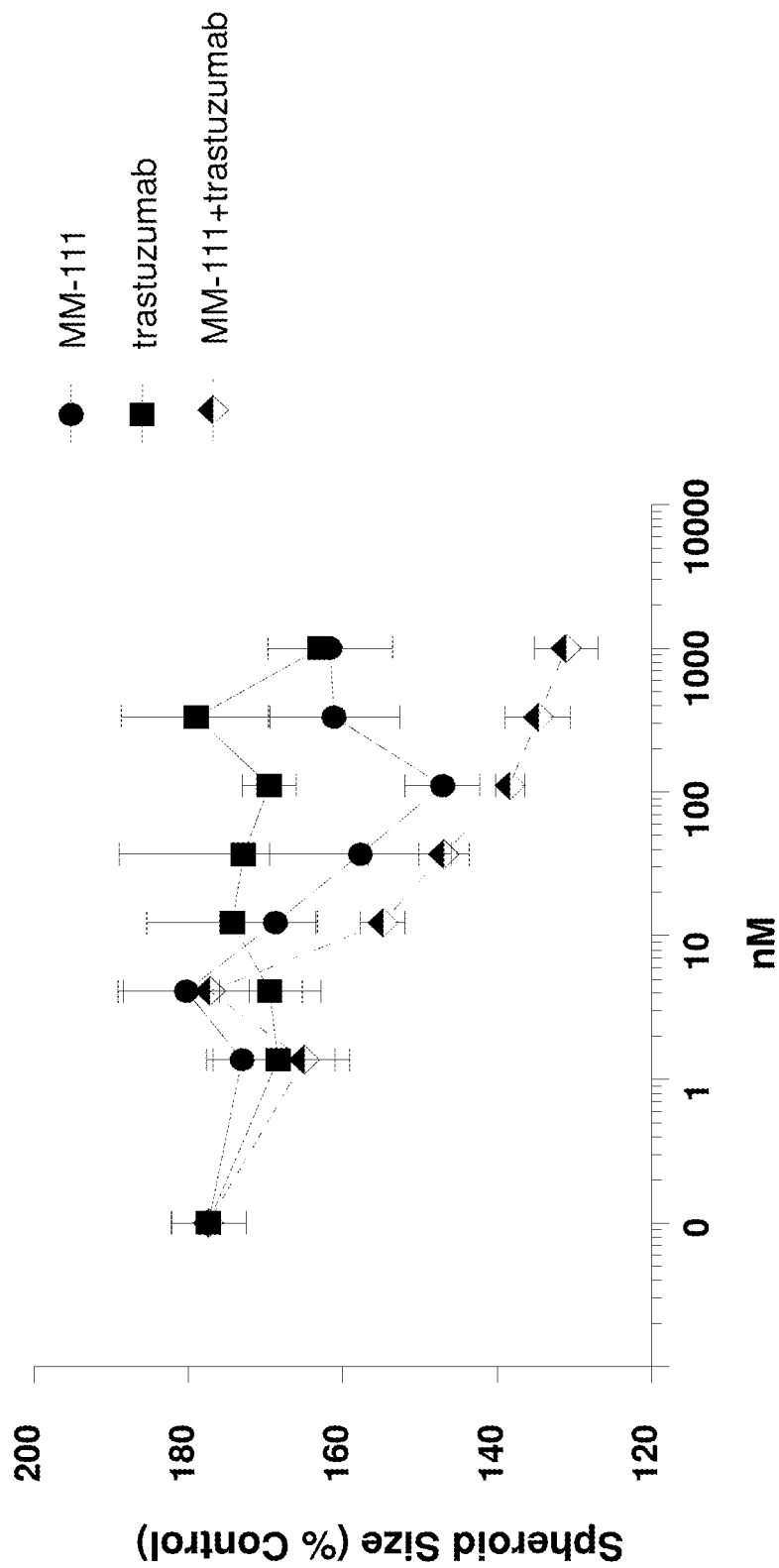
FIG. 4e shows the effect of MM-111, trastuzumab, or MM-111 and trastuzumab.
Figure 4F:
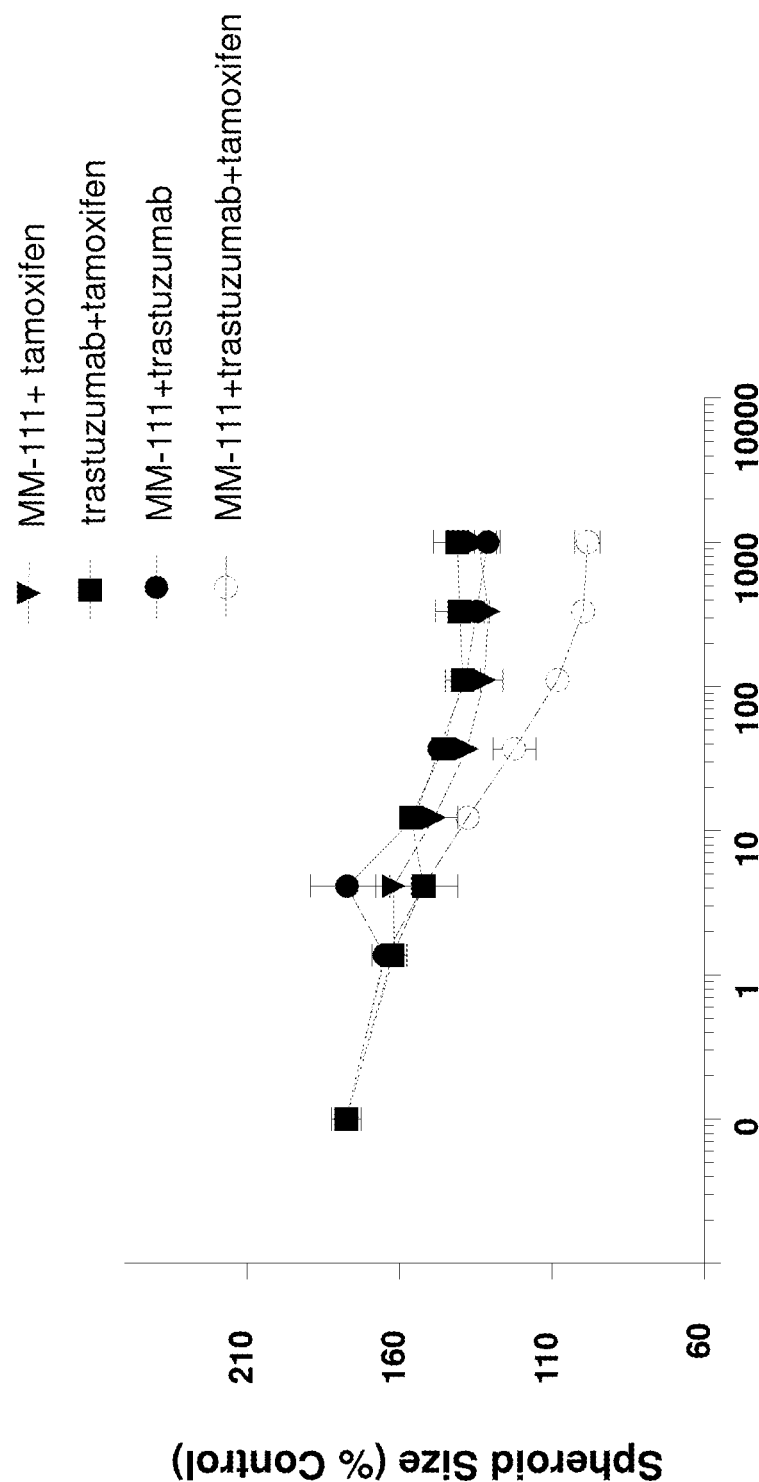
FIG. 4f shows the effect of MM-111, trastuzumab, and tamoxifen combined compared to that of any of the double combinations.

Dual ligand stimulated spheroids were then treated with MM-111, trastuzumab, or a combination of MM-111 and trastuzumab. MM-111 showed greater inhibitory effects than trastuzumab in dual ligand-stimulated spheroid growth. Enhanced inhibitory effects were observed when both drugs were combined (FIG. 4e).

Figure 4G:
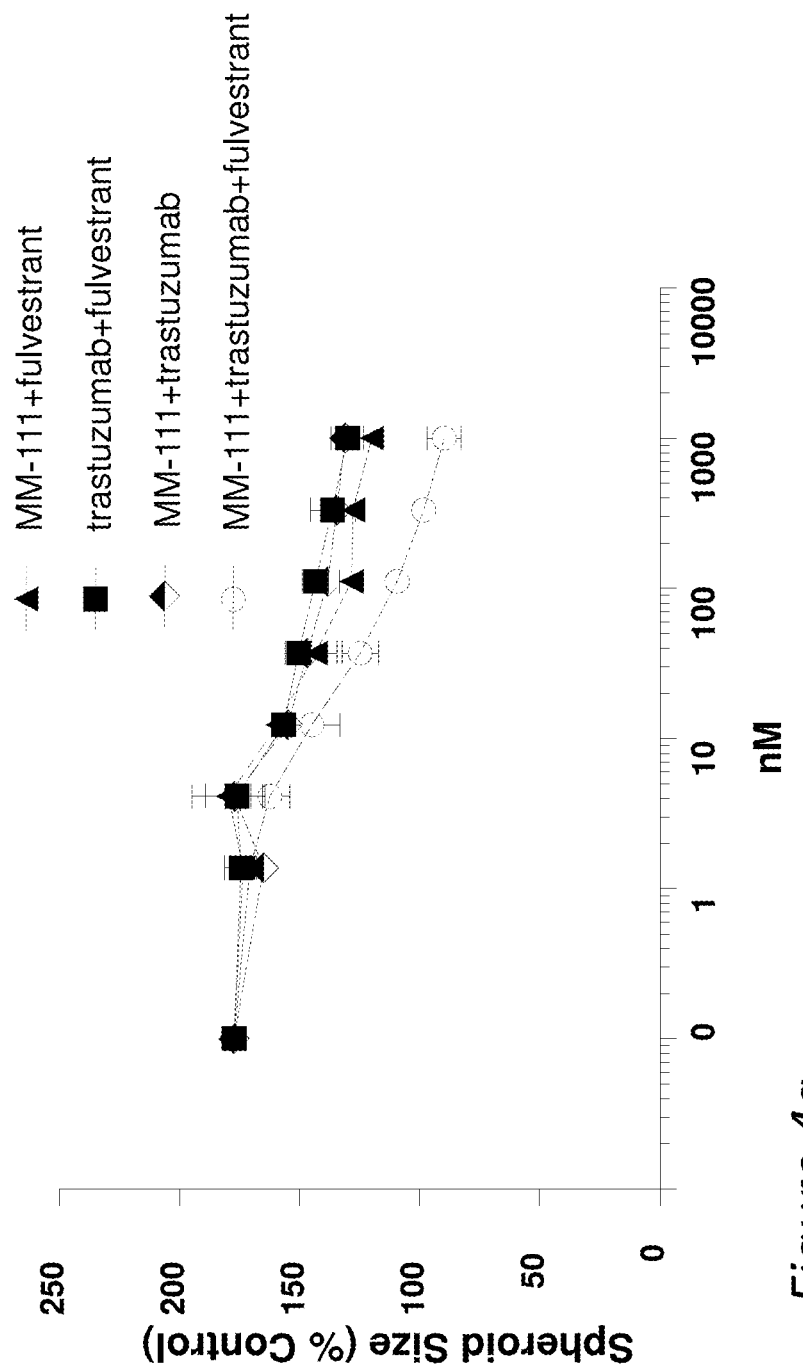
FIG. 4g shows the effect of MM-111, trastuzumab, and fulvestrant combined compared to that of any of the double combinations. The x-axes are a log scale of each drug concentration for each experimental condition in nM and the y axis is spheroid size as % of control spheroid size.

In comparison to the double combination of MM-111 or trastuzumab with tamoxifen or fulvestrant, the triple combination of MM-111, trastuzumab and either tamoxifen (FIG. 40 or fulvestrant (FIG. 4g) showed similar inhibitory effects to those of MM-111 and trastuzumab in combination (FIG. 4e) on estrogen- and heregulin-(dual ligand) stimulated spheroid growth.

Figure 5:
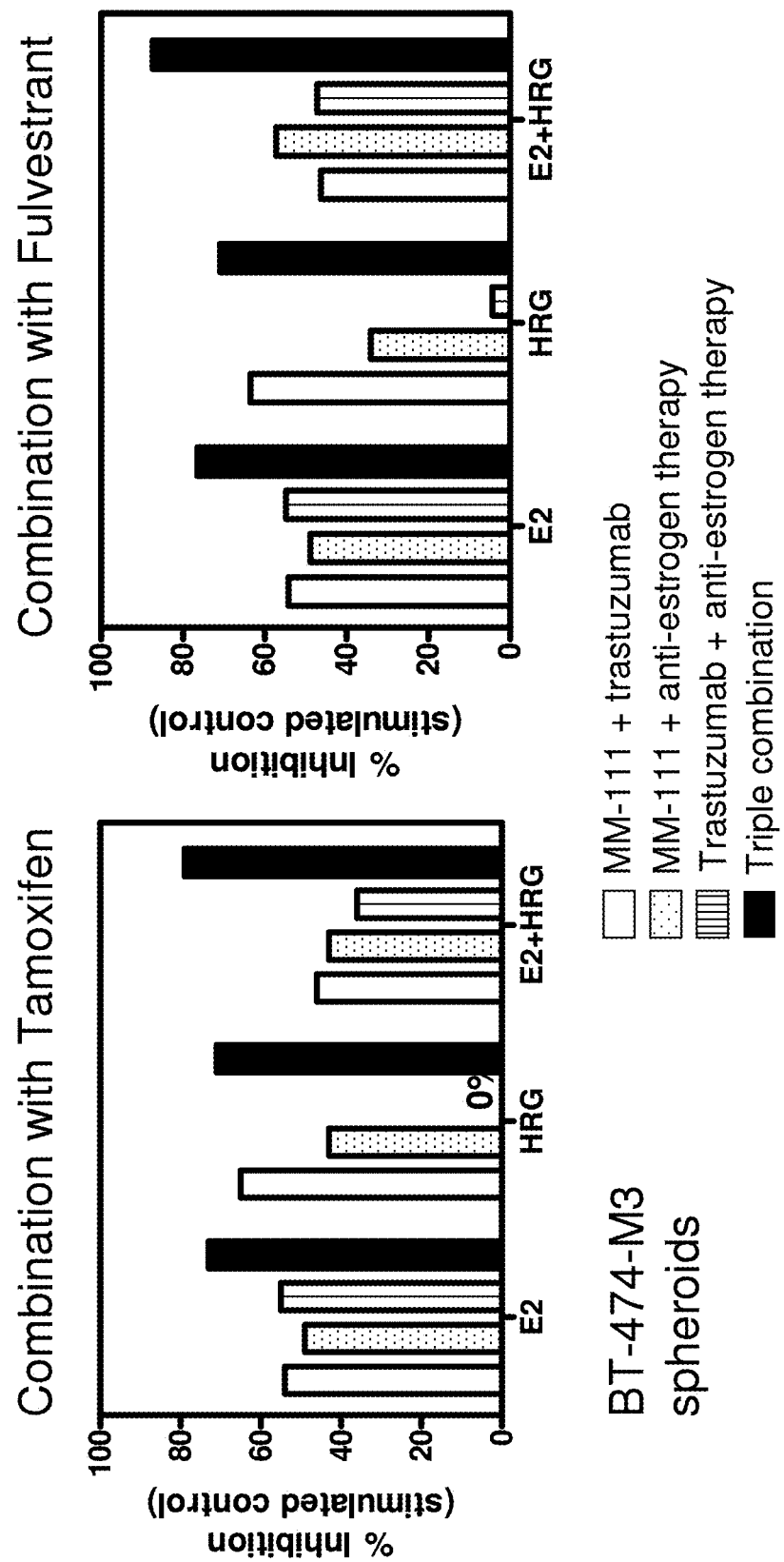
FIG. 5 is a graph summarizing the effect of MM-111, trastuzumab, and tamoxifen combined compared to that of any of the double combinations or MM-111, trastuzumab, and fulvestrant combined compared to that of any of the double combinations at inhibiting single ligand (estrogen or heregulin) or dual-ligand (estrogen and heregulin)-stimulated spheroid growth in vitro. The y-axis is % inhibition of spheroid size normalized to stimulated control.

The data in the preceding Examples demonstrate that combination therapies comprising MM-111 and an anti-estrogen therapeutic are more effective than each of these therapies alone. The percent of spheroid growth inhibition induced by each treatment under estrogen or heregulin stimulation is summarized in FIG. 5 and Table 1. MM-111 was required for inhibition of spheroids stimulated with heregulin. For each stimulated condition tested, the triple combination resulted in the greatest inhibition of spheroid growth, providing a percent inhibition ranging from about 70% to about 90%.

TABLE 1

Percent inhibitor induced maximal spheroid growth inhibition

| | MM-111 + Trastuzumab | MM-111 + anti-estrogen | Trastuzumab + anti-estrogen | Triple combination |
|---|---|---|---|---|
| Tamoxifen combination | | | | |
| E2 | 54% | 49% | 55% | 73% |
| HRG | 65% | 43% | 0% | 71% |
| E2 + HRG | 46% | 43% | 36% | 79% |

TABLE 1-continued

Percent inhibitor induced maximal spheroid growth inhibition

| | MM-111 + Trastuzumab | MM-111 + anti-estrogen | Trastuzumab + anti-estrogen | Triple combination |
|---|---|---|---|---|
| Fulvestrant combination | | | | |
| E2 | 54% | 49% | 55% | 77% |
| HRG | 64% | 34% | 4% | 71% |
| E2 + HRG | 46% | 57% | 47% | 88% |

The percent of spheroid growth inhibition (normalized to untreated, stimulated control) was determined for 1 μM doses of inhibitor treatment.

The combination of MM-111 and tamoxifen resulted in potent inhibition of tumor growth in vivo. Taken together, these data demonstrate that the combination of MM-111 and anti-estrogen therapies results in potent anti-tumor effects in vitro and in vivo.

MM-111 in Combination with Lapatinib

Methods
Computational Modeling
A computational model of HRG-induced phospho-ErbB3 signaling, as well as a model of lapatinib, was used as previously described (Schoeberl, et al 2009).
Cell Signaling Assay
Serum-starved cells are pre-incubated with serial dilutions of MM-111, lapatinib or combinations at doses and treatment times indicated, followed by stimulation with 5 nM heregulin 1-β (R&D Systems, Minneapolis, Minn.) for 10 minutes. Cell lysates are probed for phospho-ErbB3 (pErbB3), and phospho-AKT (pAKT) by ELISA as described previously (Schoeberl et al, 2009) Inhibitor $IC_{50}$ values are calculated by fitting dose-response data to a 4-parameter sigmoidal curve (GraphPad Prism®, GraphPad Software, Inc., La Jolla, Calif.).
Cell Proliferation Assay
Cells (8,000/well) are seeded into 96-well plates and incubated overnight Inhibitor is added at doses indicated and cells are treated for 24 hours. For experiments with ligand stimulation, cells are serum-starved overnight prior to addition of inhibitor and 2 nM heregulin 1-☐ (R&D Systems, Minneapolis, Minn.) is added 1 hour post-inhibitor treatment in media containing 5% FBS. Numbers of viable cells are measured as an indicator of cell proliferation using the CellTiter-Glo® Luminescent Cell Viability Assay (Promega, Madison, Wis.).
Apoptosis Assay
BT474-M3 cells (2000 cells/well) are plated in Ultra Low Cluster 96-well plate (Costar®, Corning, N.Y.). After overnight incubation, spheroids are treated with inhibitor at concentrations indicated for 72 hours. Spheroids are then trypsinized and combined with floating cells. Cells are washed twice with cold PBS and suspended in binding buffer (0.01 M HEPES, pH 7.4; 0.14 M NaCl; 2.5 mM $CaCl_2$). Cells are then stained with FITC-conjugated Annexin V and PI. Apoptotic cells are quantified on a FACSCalibur™ FACS machine.
Xenograft Efficacy Studies
Tumor xenografts are established by subcutaneous injection of BT474-M3 cells into the flank of 5-6 weeks old female athymic nude mice (nu/nu; Charles River Labs, Wilmington, Mass.). Mice receive a subcutaneous 60 day, slow-release estrogen implant in the opposite flank (0.72 mg pellet; Innovation Research of America, Sarasota, Fla.) 24 hours prior to the injection of cells. Once tumors reach a mean volume of 150-500 $mm^3$, mice are randomized into groups of 8 or 10 and dosed by intraperitoneal injection once every three days with vehicle, MM-111 or lapatinib. For lapatinib combination studies, MM-111 is given once every seven days and lapatinib daily by gavage at doses indicated.

Aromatase-Overexpressing BT474-M3 Cells and Proliferation Assay

BT474-M3 cells were transfected with PS100010 vector containing human aromatase (gene accession No: NM_000103.2). Cells with stable expression of aromatase (BT474-M3-Aro) were obtained after selection with 400 μg/ml geneticin. For cell proliferation assay, BT474-M3-Aro cells (5000 cells/well) were plated in phenol red-free RPMI-1640 medium containing 5% charcoal-stripped FBS into 96-well plate. After overnight incubation, indicated treatments were introduced in the presence of androstenedione (A-4; 200 nM) and heregulin (HRG; 2 nM). After three days of treatment, cell viability was determined by WST-1 (Roche; Cat. #11 644 807 001) according to manufacturer's instruction. Cell viability in the presence of 5% charcoal-stripped FBS was set as control (100%).

Example 5

The Combination of MM-111 and Lapatinib Inhibits Tumor Growth In Vivo

Figure 6:
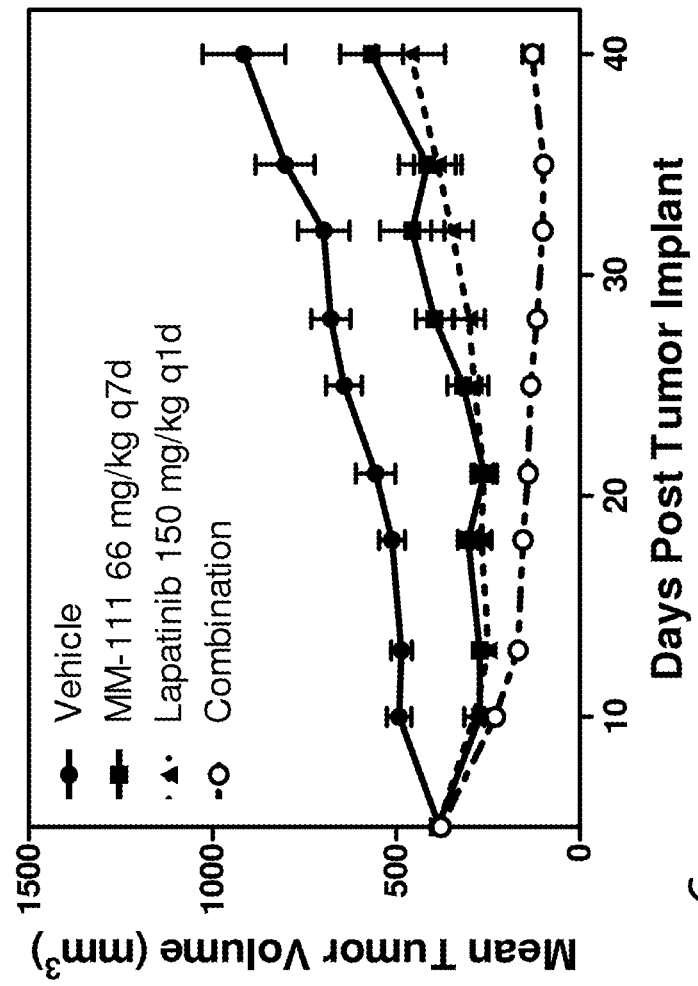
FIG. 6 is a graph showing that the combination of MM-111 and lapatinib inhibits tumor growth in vivo. The x-axis shows the time post tumor implant in days and the y-axis shows tumor volume in $mm^3$. Mice were treated with inhibitors on day 7 post tumor implant.

The combination of MM-111 with lapatinib was investigated in vivo in the BT474-M3 breast cancer xenograft model using the methods described above or minor variations thereof. MM-111 and lapatinib were each dosed at an optimal efficacious dose weekly and daily, respectively. The combination of MM-111 and lapatinib provided more potency compared to either drug alone, reaching statistical significance for MM-111 ($p=3.9\times10-4$) and lapatinib ($p=5.1\times10-3$) on day 13 (FIG. 6). The percent change in tumor volume from day 40 to day 7 (inoculation) was calculated for each group (FIG. 6b). The combination of MM-111 and lapatinib resulted in a percent change in tumor volume of −69% (about 70%), reflecting tumor regressions, compared to −11% (about 10%) for lapatinib and 14% (about 15%) for MM-111.

Example 6

Figure 7A:
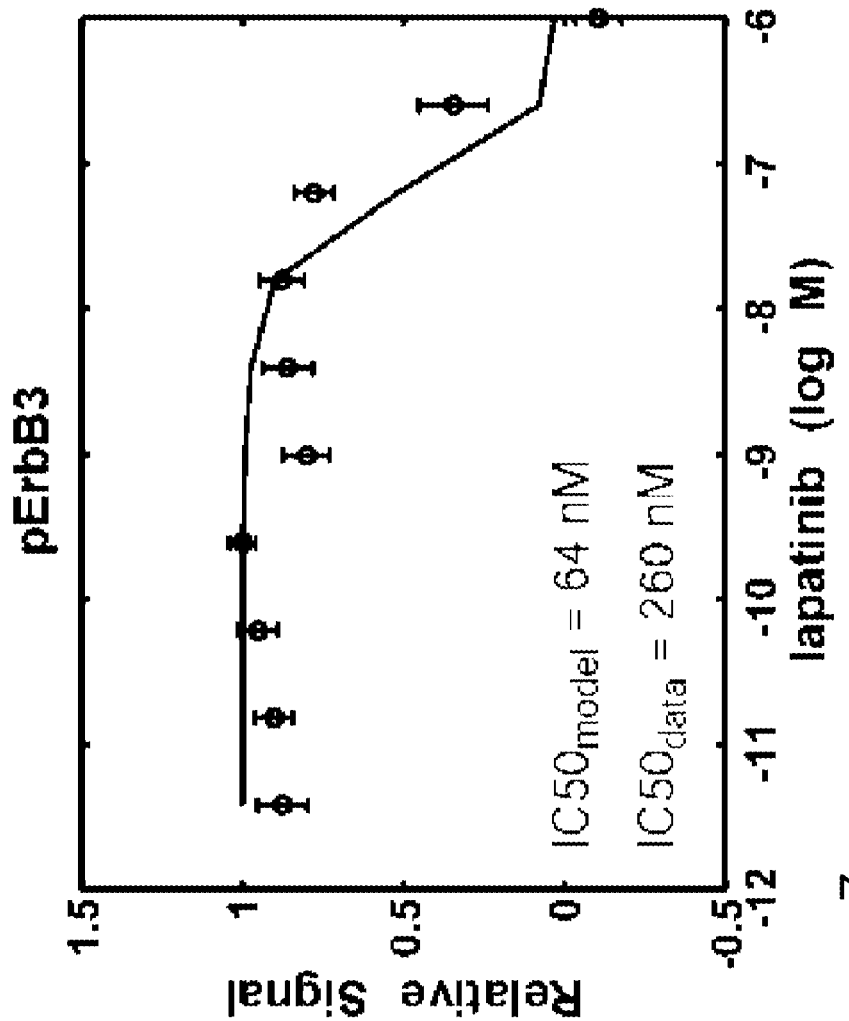
FIG. 7 evaluates the ability of lapatinib to inhibit ErbB3 and AKT activation in heregulin-stimulated cells. 7a is a graph comparing computer-generated dose-response curves to experimental results in heregulin-stimulated BT474-M3 cells. 7b is a graph showing lapatinib inhibition (IC50) of ErbB3 and AKT activation in heregulin-stimulated and unstimulated cells following a 1-hour incubation with inhibitor.
Figure 7B:
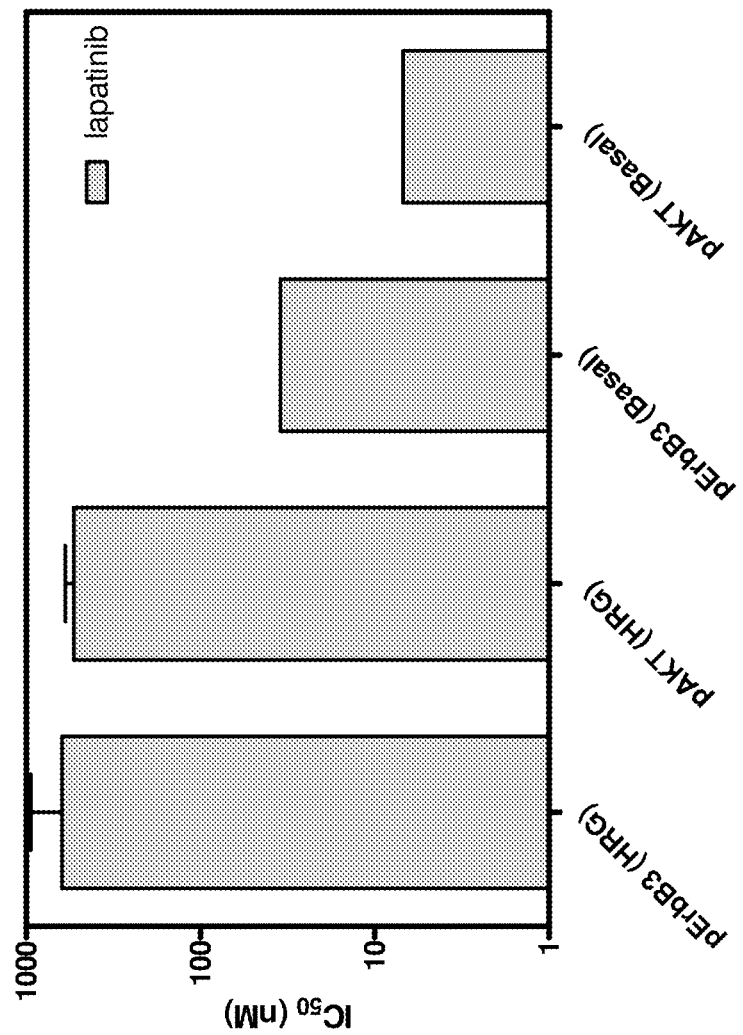

Simulations Predict Lapatinib has Suboptimal Activity in Inhibiting Heregulin-Driven pErbB3 and pAKT A dose range of lapatinib inhibition of pErbB3 activation was predicted using the computational modeling described above. A dose range of lapatinib was applied to BT474-M3 cells followed by stimulation with 5 nM heregulin for 10 min. The amount of pErbB3 was measured by ELISA using the methods described above or minor variations thereof. Model-generated dose-response curves overlay the experimental data (FIG. 7a). A comparison of the inhibitory activity of lapatinib in heregulin-stimulated or unstimulated (basal) cells was performed to demonstrate that heregulin signaling perturbs the activity of lapatinib. Untreated and heregulin-stimulated cells were probed for pErbB3 and pAKT and the IC50 was calculated (FIG. 7b). These data show that lapatinib alone is not an effective inhibitor of heregulin-activated signaling.

Example 7

Figure 8A:
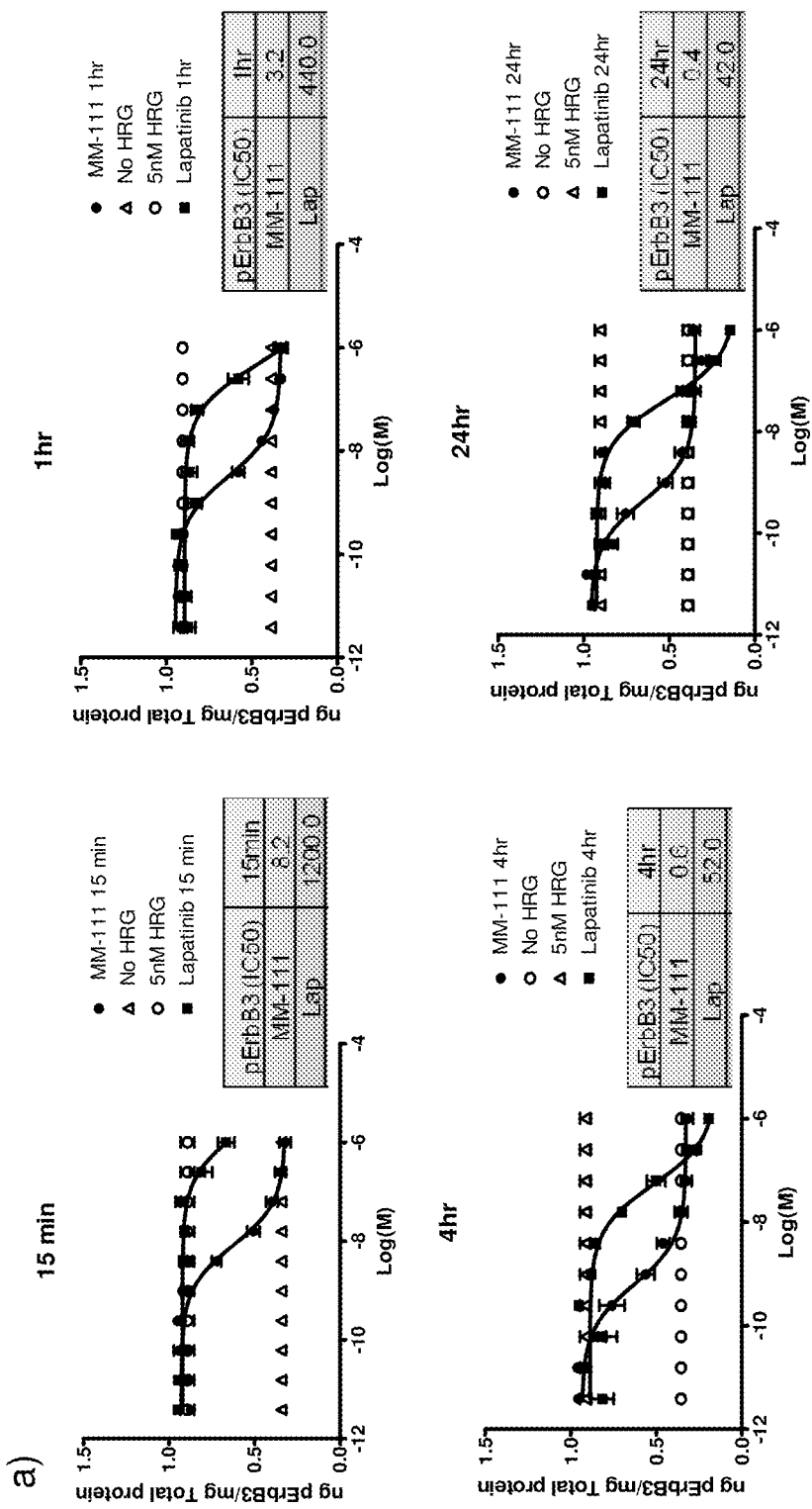
FIG. 8 is a series of graphs showing MM-111 or lapatinib inhibition of ErbB3 (8a) or AKT (8b) activation in heregulin-stimulated cells incubated with inhibitor for 15 minutes, 1 hour, 4 hours, and 24 hours.
FIG. 8c shows a comparison of IC50 for MM-111 and lapatinib at 1 hour and 24 hours for both BT474M3 cells and ZR75-30 cells.
Figure 8B:
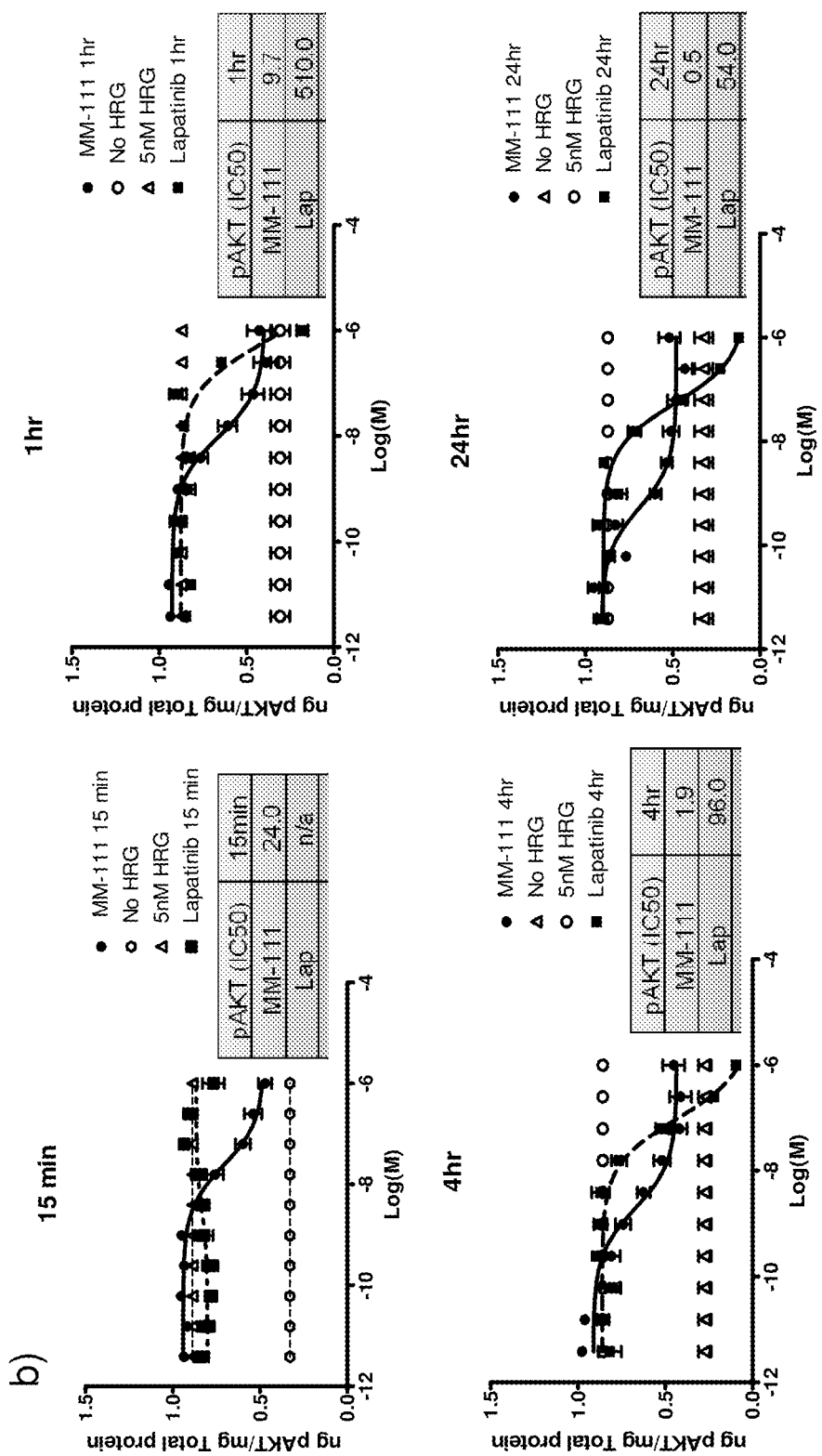
Figure 8C:
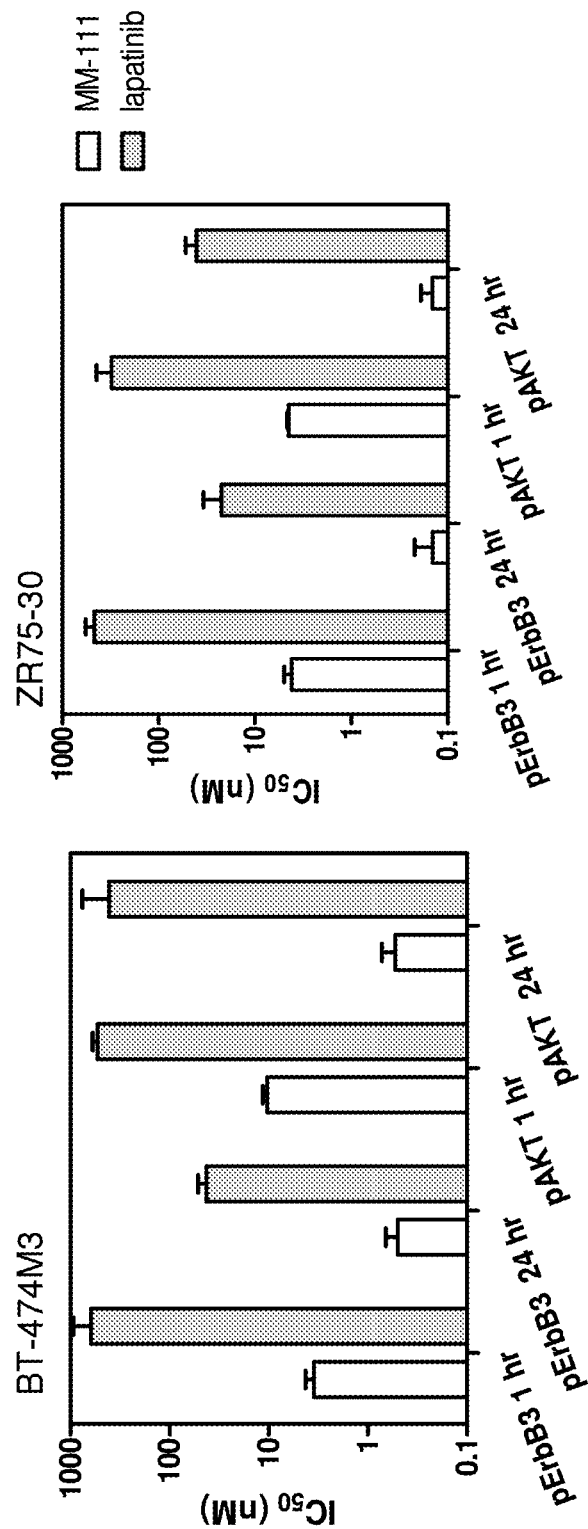

MM-111 is a More Potent Inhibitor of HRG-Driven ErbB3 and AKT Phosphorylation than Lapatinib In order to compare the ability of MM-111 and lapatinib to inhibit heregulin-induced ErbB3 activation, BT474-M3, or an additional ErbB2 overexpressing breast tumor cell line, ZR75-30 (ATCC® #CRL-1504™), cells were incubated with serial dilutions of either inhibitor for 15 minutes, 1 hour, 4 hours, and 24 hours followed by stimulation with 5 nM heregulin for 10 min. Amounts of pAKT and pErbB3 were measured by ELISA essentially as described. MM-111 potently reduced pErbB3 levels (inhibited ErbB3 phosphorylation) in BT474-M3 ($IC_{50}=3$ nM) cells (FIG. 8a) and ZR75-30 cells ($IC_{50=5}$ nM) (FIG. 8c). Good reduction by MM-111 of pAKT levels (inhibition of AKT phosphorylation) in BT474-M3 ($IC_{50}=10$) (FIG. 8b) and in ZR75-30 cells ($IC_{50}=4$ nM) (FIG. 8d) was also observed. The ability of MM-111 to inhibit heregulin-induced ErbB3 activation (phosphorylation) was superior to lapatinib by greater than an order of magnitude and the relative $IC_{50}$ for each inhibitor (FIG. 8c) was consistent following up to 24 hours incubation with inhibitors, indicating treatment times had little effect on the potency of the inhibitors.

Example 8

The Combination of MM-111 and Lapatinib Potently Inhibits pAKT

Figure 9:
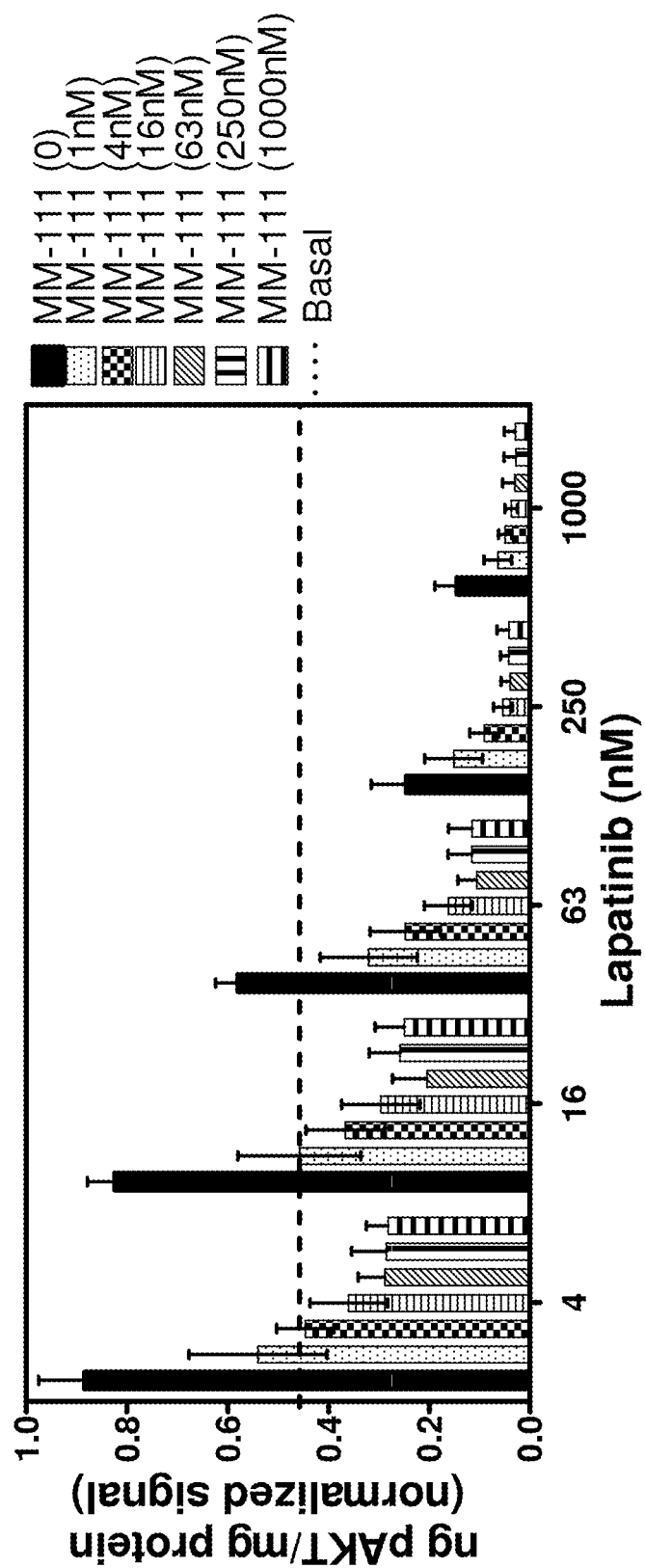
FIG. 9 is a graph showing the effect of MM-111 and lapatinib combination treatment on AKT activation in heregulin-stimulated BT474-M3 cells.

The effect of MM-111 combined with lapatinib on pAKT inhibition (reduction of pAKT levels) was assessed in heregulin-stimulated BT474-M3 cells. Cells were incubated for 2 hours with a dose range of MM-111, lapatinib or their combination and pAKT was measured by ELISA. In the presence of heregulin, the combination of MM-111 and lapatinib was extremely effective, inhibiting pAKT well below basal levels at therapeutically relevant concentrations (FIG. 9). Treatment with either MM-111 (1 μM) or lapatinib (1 μM) alone resulted in similar levels of pAKT inhibition (see FIG. 8b) while the combination resulted in about 20% more inhibition of pAKT.

Example 9

Figure 10:
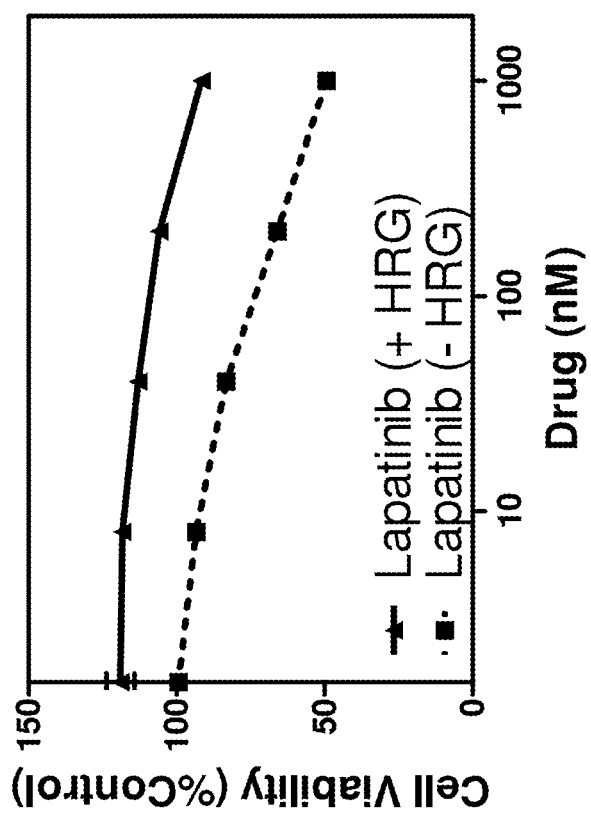
FIG. 10 is a graph showing the effect of lapatinib on cell viability as a measure of proliferation of unstimulated and heregulin-stimulated BT474-M3 cells.

The Ability of Lapatinib to Inhibit Cell Proliferation is Perturbed Under Heregulin-Stimulated Conditions The effect of lapatinib on cell proliferation was measured in unstimulated and heregulin-stimulated BT474-M3 cells. Cells grown in serum or in serum plus 2 nM heregulin were treated with lapatinib across a dose range for 24 hours. Lapatinib treatment resulted in about a 50% inhibition of unstimulated cells but its effect was reduced to about 23% inhibition in heregulin-stimulated BT474-M3 cells (FIG. 10).

Example 10

Figure 11:
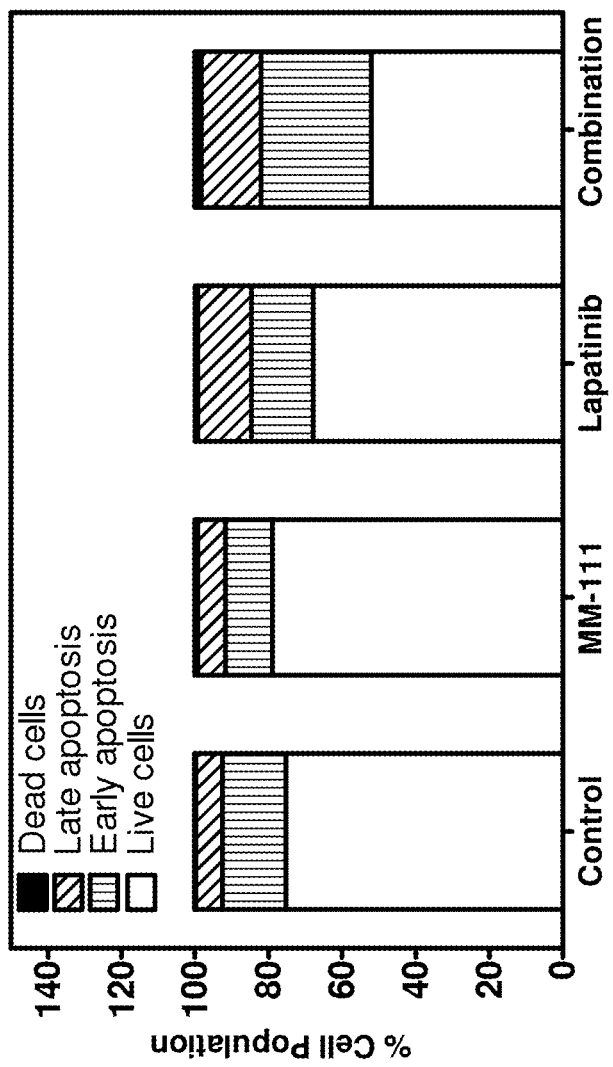
FIG. 11 is a graph showing the effect of MM-111, lapatinib, or the combination on BT474-M3 cell apoptosis. The number of dead cells, cells in late apoptosis, early apoptosis, and live cells was quantitated.

Treatment with the Combination of MM-111 and Lapatinib Results in Increased Apoptosis The effect of the MM-111 combination with lapatinib on apoptosis was assessed in a BT474-M3 spheroid model. Spheroids were prepared using the methods described above or minor variations thereof and treated with MM-111 (100 nM), lapatinib (33 nM), or a combination of 100 nM MM-111 and 33 nM lapatinib. Cells were then stained with Annexin V and propidium iodide (PI) and quantitated using FACS (FIG. 11, Table 2). Cell populations staining positive with Annexin V and PI were quantified as late apoptotic, cell populations staining positive with Annexin V but not PI were quantified as early apoptotic, cell populations staining positive for PI but not Annexin V were quantified as dead cells and populations of cells not stained with either Annexin V or PI were considered alive and not apoptotic (Table 2). Spheroids that were treated with both MM-111 and lapatinib had a higher number of total apoptotic cells (about 46%) compared to those treated with only lapatinib (about 31%) or only MM-111 (about 20%; FIG. 10).

TABLE 2

Percent cell population after treatment with MM-111, lapatinib or the combination

|  | Live cells | Early apoptosis | Late apoptosis | Dead cells |
|---|---|---|---|---|
| Control | 75.2 | 17.3 | 7.2 | 0.42 |
| MM-111 | 78.9 | 12.9 | 7.5 | 0.74 |
| Lapatinib | 67.9 | 16.8 | 14.5 | 0.73 |
| Combination | 52.1 | 30.0 | 16.2 | 1.74 |

Example 11

Figure 12A:
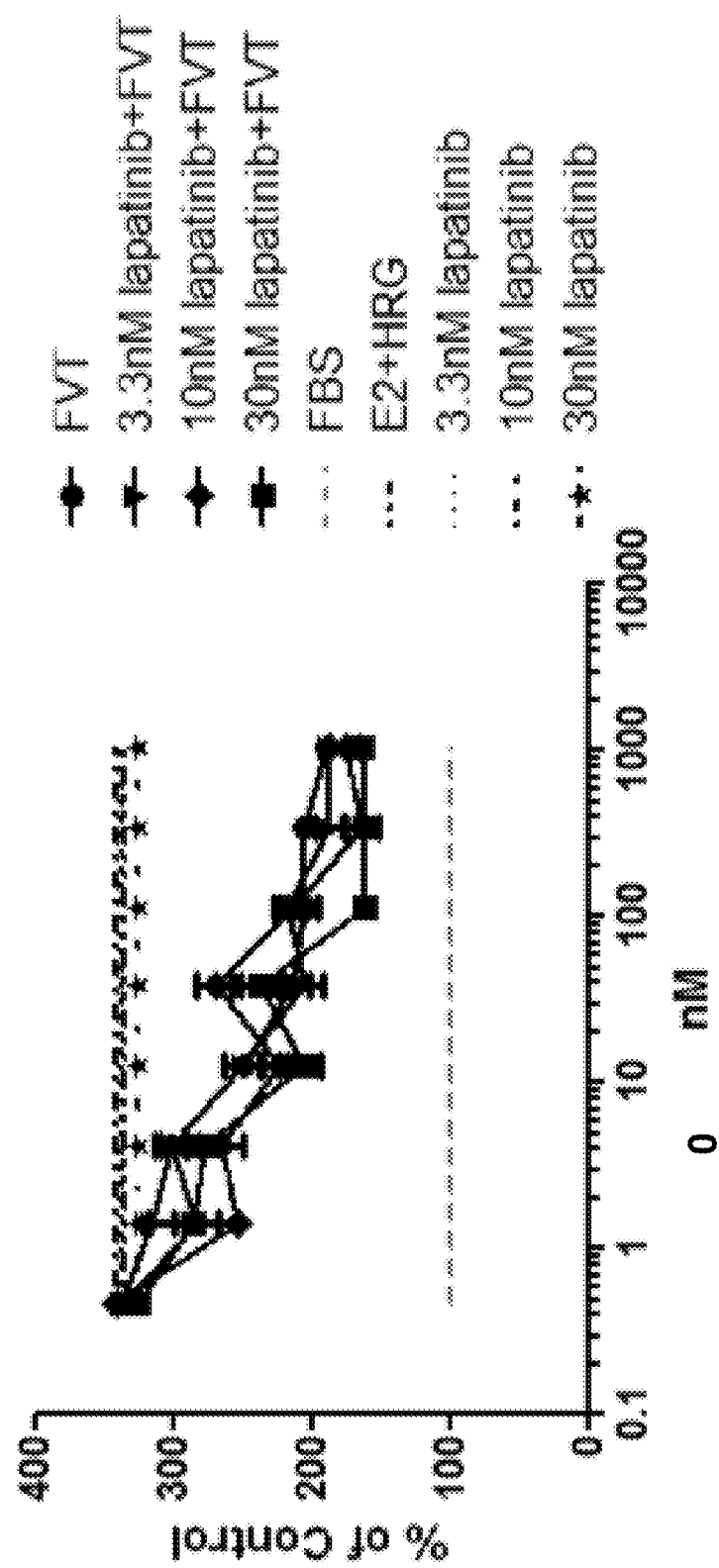
FIG. 12a shows the effect of lapatinib alone or the combination of lapatinib and fulvestrant (FVT).
Figure 12B:
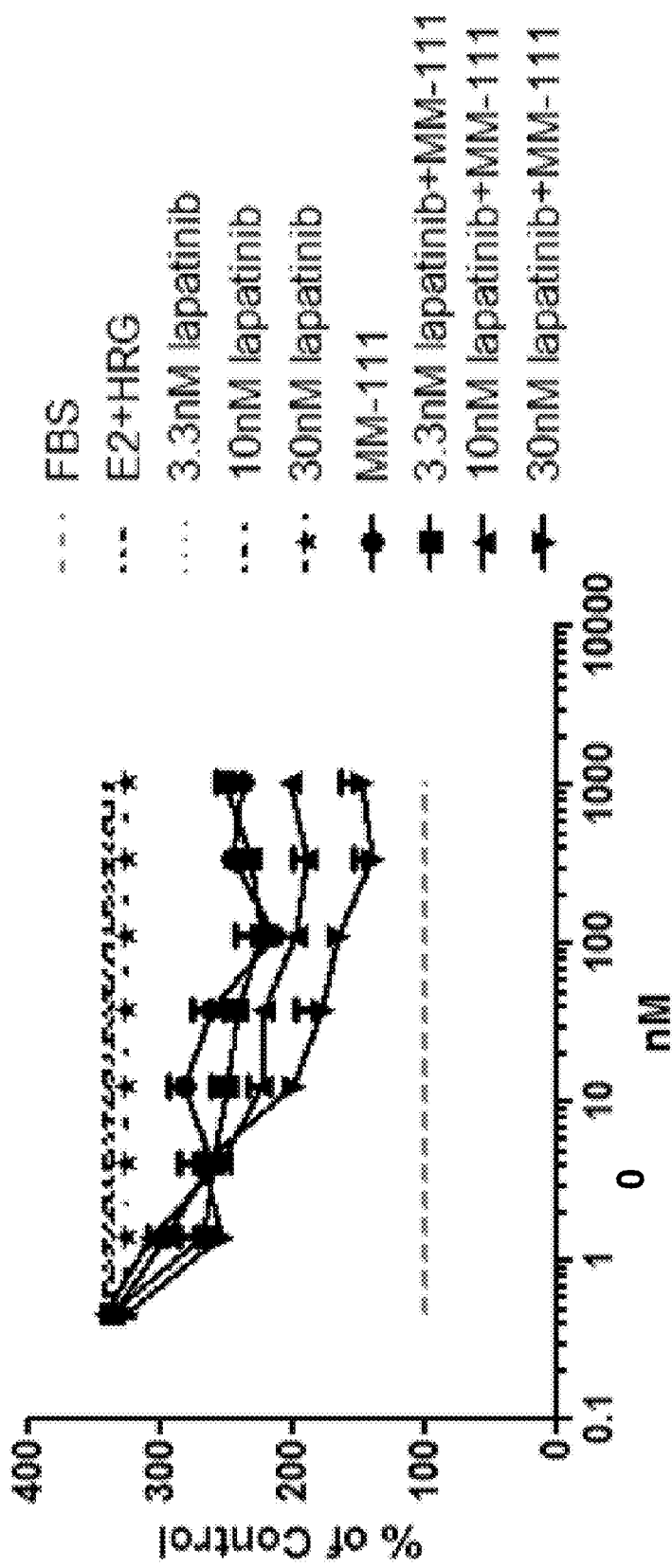
FIG. 12b shows the effect of lapatinib alone or the combination of lapatinib and MM-111.
Figure 12C:
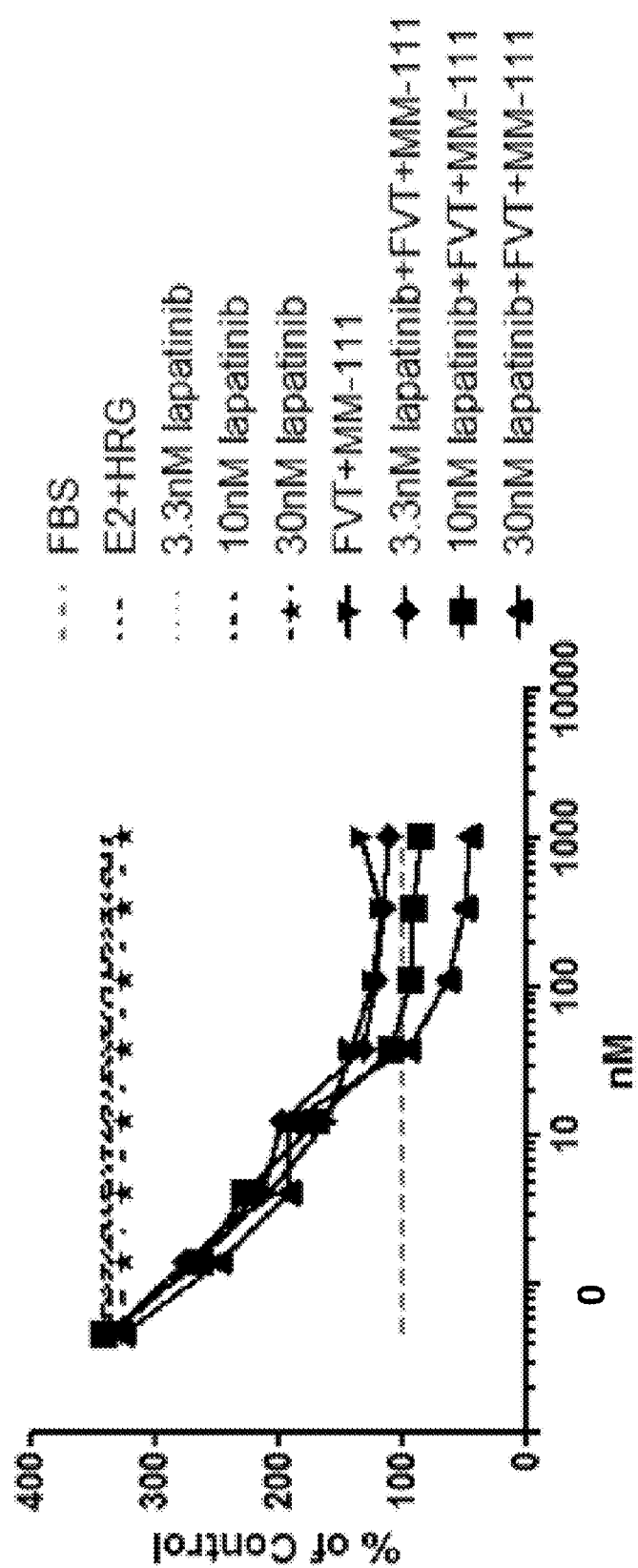
FIG. 12c shows the effect of lapatinib alone, the combination of MM-111 and fulvestrant, or the triple combination of MM-111, FVT, and lapatinib. Lapatinib is given in 3.3, 10, or 30 nM doses. The x-axes are a log scale of each of MM-111 and/or FVT concentration in nM and the y axis is spheroid size as % of control (FBS alone) spheroid size.

MM-111 Combines Positively with Anti-Estrogen Drugs and Lapatinib in Inhibiting Dual Ligand (Estrogen and Heregulin)-Stimulated Spheroid Growth To further investigate the ability of MM-111 to inhibit cell growth when in combination with both anti-estrogen drugs and tyrosine kinase inhibitors, spheroids of estrogen and heregulin-stimulated BT474-M3 cells were prepared using the methods described above or minor variations thereof and treated with 3.3 nM, 10 nM, or 30 nM lapatinib, either alone or in combination with a dose range of fulvestrant (FVT) (FIG. 12a); 3.3 nM, 10 nM, or 30 nM lapatinib, either alone or in combination with a dose range of MM-111 (FIG. 12b); or 3.3 nM, 10 nM, or 30 nM lapatinib, either alone or in combination with a dose range of both MM-111 and fulvestrant (FIG. 12c). In the presence of dual ligand stimulation the combination of lapatinib and FVT did not greatly increase inhibition of spheroid growth over lapatinib alone (FIG. 12a). In contrast, the addition of MM-111 greatly increased the sensitivity of the spheroids to lapatinib treatment (FIG. 12b), and the triple combination of lapatinib, FVT and MM-111 showed an even greater increase of spheroid growth inhibition over lapatinib alone.

Example 12

Figure 13A:
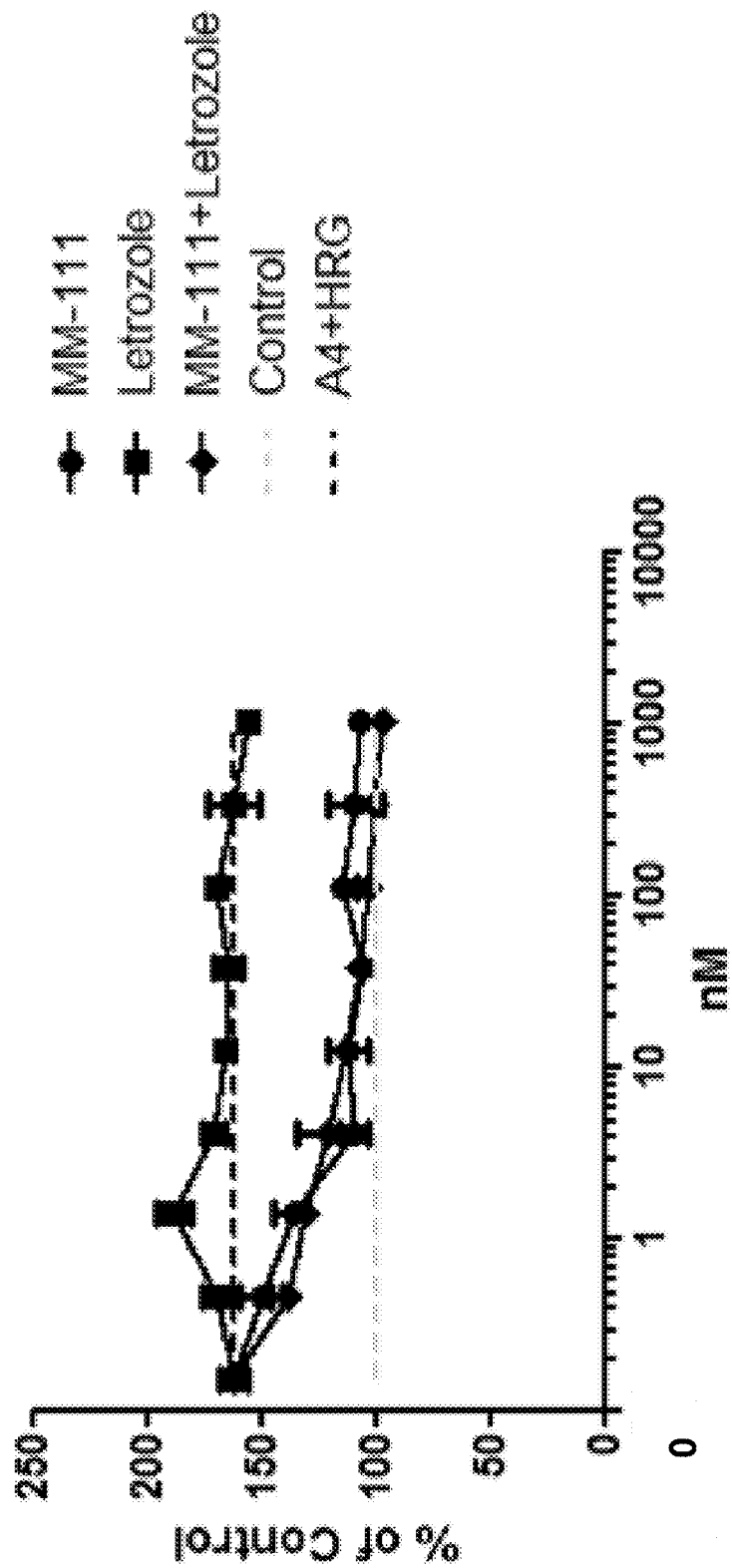
FIG. 13a shows the effect of letrozole, MM-111, or the combination of letrozole and MM-111.
Figure 13B:
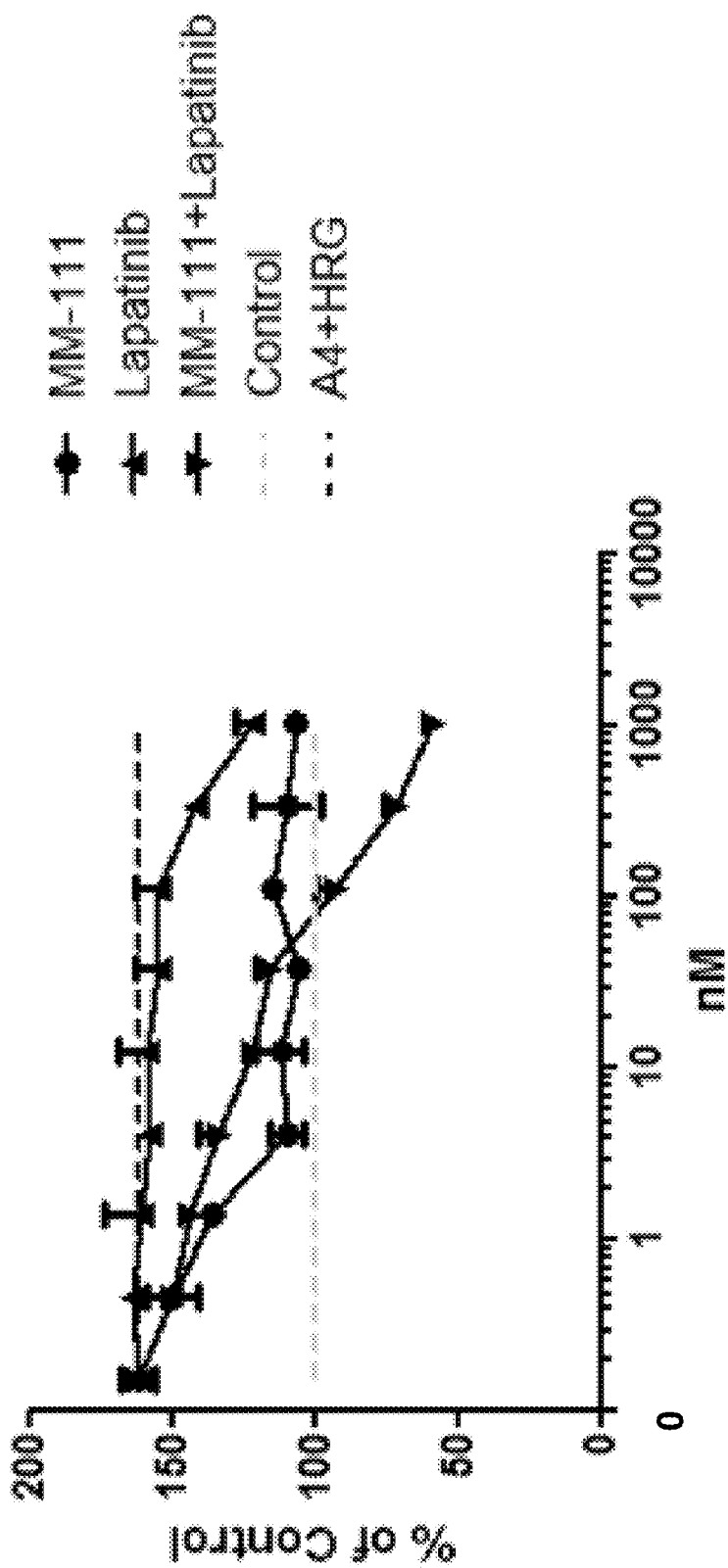
FIG. 13b shows the effect of lapatinib, MM-111 or the combination of lapatinib and MM-111.
Figure 13C:
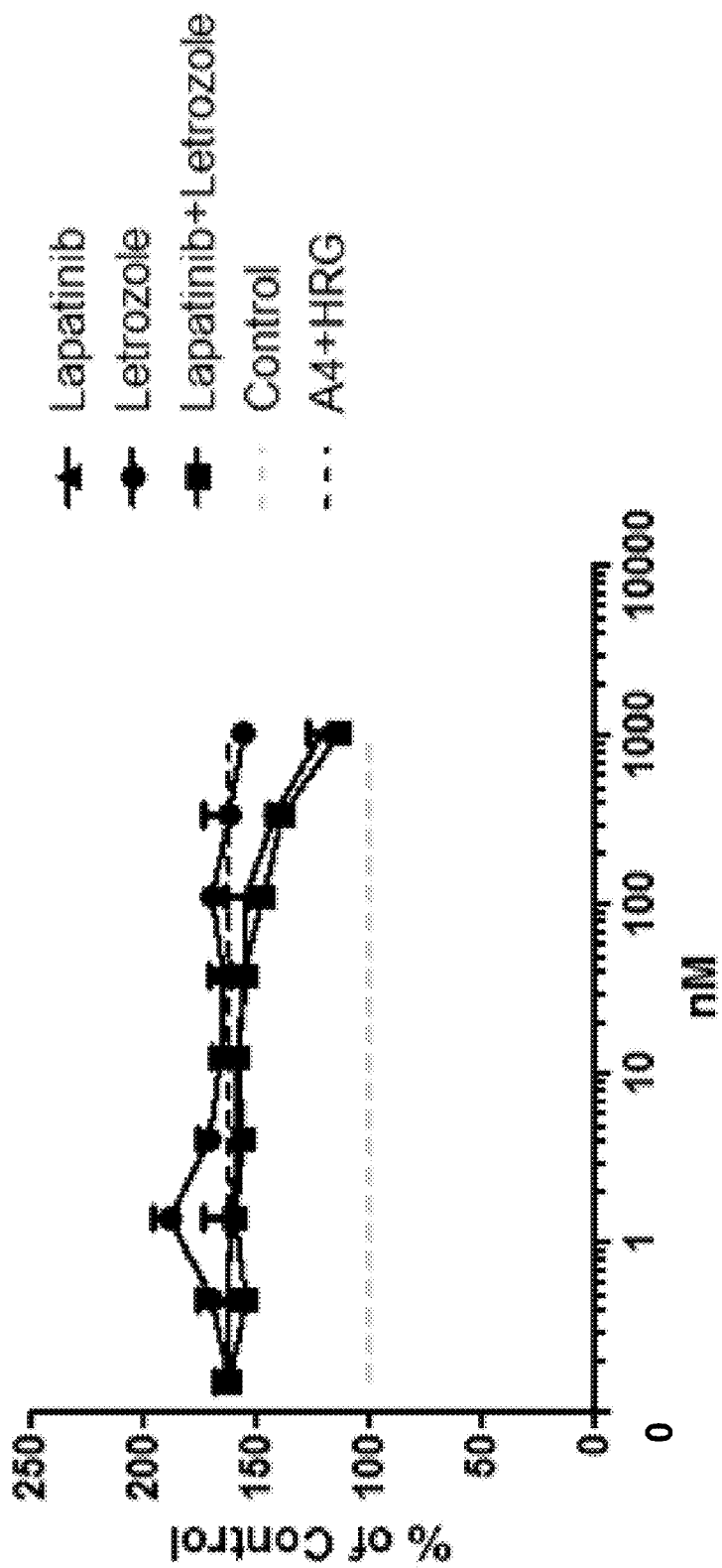
FIG. 13c shows the effect of lapatinib, letrozole, or the combination of lapatinib and letrozole.
Figure 13D:
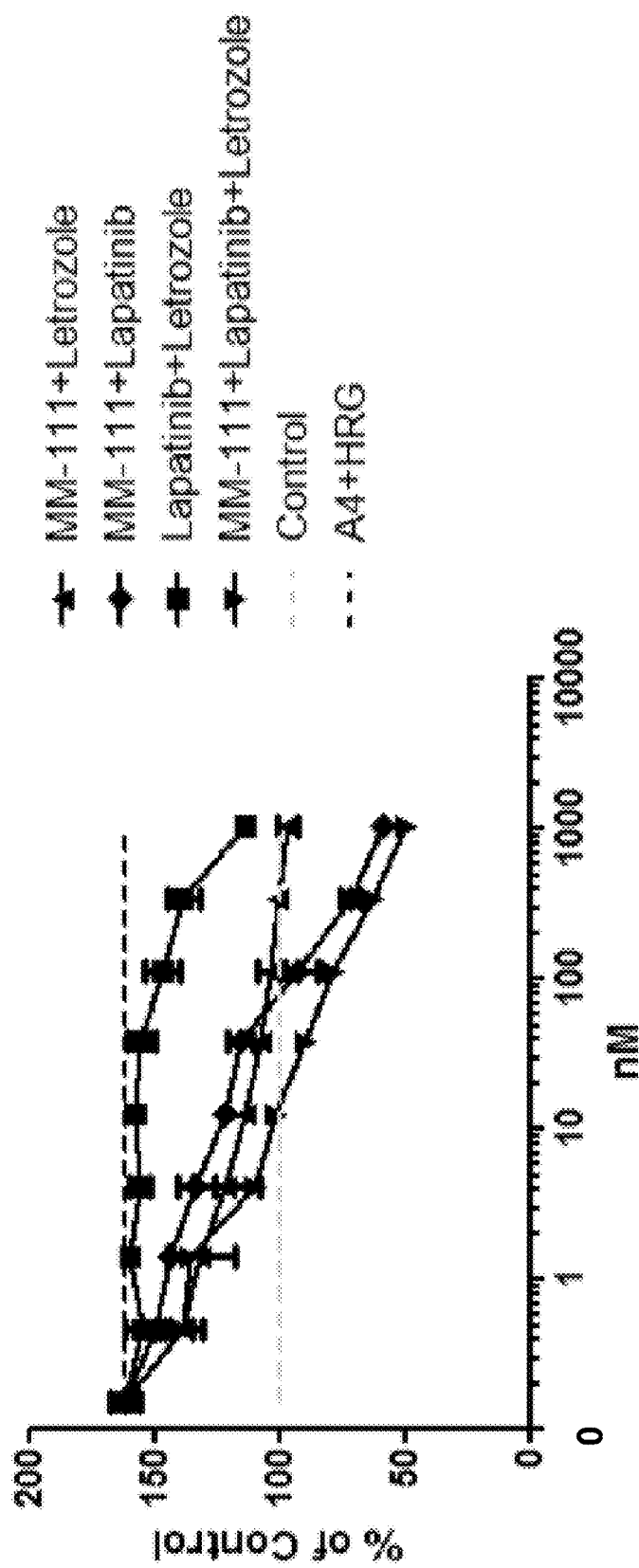
FIG. 13d shows the effect of the dual combinations of MM-111 and letrozole, MM-111 and lapatinib, lapatinib and letrozole, and the triple combination of MM-111, lapatinib and letrozole. The x-axes are a log scale of MM-111 concentration in nM. The drug concentrations are a ratio of 10:20:1 MM-111 to letrozole to lapatinib. The y axis is spheroid size as % of control spheroid size.

MM-111 Combines Positively with Anti-Estrogen Drugs in Inhibiting Spheroid Growth in BT474-M3 Cells Overexpressing Human Androstenedione Androstenedione is a steroid hormone that is converted to estrogen by aromatase. To further investigate the ability of MM-111 to inhibit spheroid growth, aromatase-expressing cells were treated in the presence of androstenedione (A4) and heregulin (HRG) with MM-111, letrozole, or the combination of MM-111 or letrozole (FIG. 13a); MM-111, lapatinib, or the combination of MM-111 and lapatinib (FIG. 13b); lapatinib, letrozole, or the combination of lapatinib and letrozole (FIG. 13c); and each of the dual combination plus the triple combination of MM-111, lapatinib, and letrozole (FIG. 13d). In cells treated with A4 and HRG, the letrozole treatment did not result in significant inhibition of spheroid cell growth as compared to control (untreated) cells, whereas cells treated with MM-111 alone or the combination of MM-111 and letrozole inhibited cell proliferation to a similar extent (FIG. 13a). Lapatinib treatment of the cells did not result in growth inhibition except at high concentrations, whereas treatment with MM-111 alone or in combination resulted in similar levels of cell growth inhibition except in higher concentrations where the combination showed increased inhibition of cell growth over either of the single treatments (FIG. 13b). Treatment with lapatinib alone, letrozole alone, or the combination of lapatinib and letrozole did not result in significant cell growth inhibition except at high concentration (FIG. 13c). Similarly, as shown in FIG. 13d, the double combination of lapatinib and letrozole resulted in cell growth inhibition only at high drug concentration. In contrast the dual combinations of MM-111 and letrozole or MM-111 and lapatinib both showed an increase in cell growth inhibition as compared to control, and the triple combination of MM-111, lapatinib, and letrozole inhibited cell growth to an even greater degree.

Example 13

Amino Acid Sequence of MM-111(SEQ ID NO:1)

QVQLQESGGGLVKPGGSLRLSCAASGFTFSSYWMSWVRQAPGKGLEWVANINRDGSASYYVD

SVKGRFTISRDDAKNSLYLQMNSLRAEDTAVYYCARDRGVGYFDLWGRGTLVTVSSASTGGGG

SGGGGSGGGGSQSALTQPASVSGSPGQSITISCTGTSSDVGGYNFVSWYQQHPGKAPKLMIYDVS

DRPSGVSDRFSGSKSGNTASLIISGLQADDEADYYCSSYGSSSTHVIFGGGTKVTVLGAASDAHK

SEVAHRFKDLGEENFKALVLIAFAQYLQQSPFEDHVKLVNEVTEFAKTCVADESAENCDKSLHT

LFGDKLCTVATLRETYGEMADCCAKQEPERNECFLQHKDDNPNLPRLVRPEVDVMCTAFHDNE

ETFLKKYLYEIARRHPYFYAPELLFFAKRYKAAFTECCQAADKAACLLPKLDELRDEGKASSAK

QRLKCASLQKFGERAFKAWAVARLSQRFPKAEFAEVSKLVTDLTKVHTECCHGDLLECADDRA

DLAKYICENQDSISSKLKECCEKPLLEKSHCIAEVENDEMPADLPSLAADFVESKDVCKNYAEAK

DVFLGMFLYEYARRHPDYSVVLLLRLAKTYETTLEKCCAAADPHECYAKVFDEFKPLVEEPQNL

IKQNCELFEQLGEYKFQNALLVRYTKKVPQVSTPTLVEVSRNLGKVGSKCCKHPEAKRMPCAED

YLSVVLNQLCVLHEKTPVSDRVTKCCTESLVNRRPCFSALEVDETYVPKEFQAETFTFHADICTL

```
SEKERQIKKQTALVELVKHKPKATKEQLKAVMDDFAAFVEKCCKADDKETCFAEEGKKLVAAS

QAALGLAAALQVQLVQSGAEVKKPGESLKISCKGSGYSFTSYWIAWVRQMPGKGLEYMGLIYP

GDSDTKYSPSFQGQVTISVDKSVSTAYLQWSSLKPSDSAVYFCARHDVGYCTDRTCAKWPEWL

GVWGQGTLVTVSSGGGGSSGGGSGGGGSQSVLTQPPSVSAAPGQKVTISCSGSSSNIGNNYVSW

YQQLPGTAPKLLIYDHTNRPAGVPDRFSGSKSGTSASLAISGFRSEDEADYYCASWDYTLSGWV

FGGGTKLTVLG
```

Dosing and Administration of MM-111 in Combination One or More Additional Therapeutics

Example 14

Mode of Administration of MM-111

MM-111 is prepared as a formulation containing 25 mg/ml MM-111 in a sterile aqueous solution comprising 20 mM L-histidine hydrochloride, 150 mM sodium chloride, pH 6.5, which is stored at 2-8° C.

MM-111 must be brought to room temperature prior to administration. Containers (e.g., vials) of MM-111 must not be shaken. The appropriate quantity of MM-111 is removed from the container, diluted in 250 mL of 0.9% normal saline and administered as an infusion using a low protein binding in-line filter (e.g., a 0.22 micrometer filter).

MM-111 is initially administered over about 90 minutes (first administration). In the absence of an infusion reaction, subsequent doses are administered over about 60 minutes.

A patient's body weight at the start of a dosing cycle is used to calculate the dose used throughout the cycle. Should a patient's body weight change by more than 10%, a new total dose is calculated to reflect this change.

Example 15

Dosage and Administration of MM-111

Preferred plasma concentrations of MM-111 achieved during treatment are at least 106 mg/L. It has now been discovered that certain combinations of dose frequency and dosage will achieve and maintain this plasma concentration during the course of treatment in at least half, and preferably in more than 60%, 70% or 80% of treated patients.

In certain embodiments a higher initial dose (loading dose—LD) is given, followed as defined intervals by at least one maintenance dose (MD). Intervals of dosing in days are typically indicated as QxD, wherein x represents an integer, so that a QxD of 7 indicates dosing every 7 days. Table 3A, Table 3B, and Table 3C below show doses and dosing intervals of the invention. In Table 3A, Table 3B, and Table 3C the indicated loading doses are optional—initial doses are preferably made at the indicated loading dose (LD), but may (e.g., as directed or at the physician's discretion) be made at the maintenance dose (MD). Table 3A provides a set of exemplary dosing intervals, loading doses and maintenance doses. Table 3B provides a variation of Table 3A allowing for dosage variability (indicated as "about") of up to +/−3 mg/mL. Table 3C appears below and provides a more extensive set of exemplary dosing intervals, loading doses and maintenance doses. In each cell of Table 3A, Table 3B, and Table 3C, the top figure is the integer x in the interval QxD (e.g., 18 as the top figure in a cell indicates a dosing interval of Q18D or every 18 days), the middle figure represents the (optional) loading dose (LD) in mg/kg, nd the bottom figure represents the maintenance dose (MD) in mg/kg. Thus the top cell in Table 3A indicates a dosing interval (QxD) of once every seven days, a loading dose (optional) of 25 mg per kg of patient body weight, and a maintenance dose of 20 mg per kg of patient body weight; while the cell furthest to the right on the top row of Table 3C indicates a dosing interval (QxD) of once every seven days, a loading dose (optional) of 30 mg per kg of patient body weight, and a maintenance dose of 15 mg per kg of patient body weight.

TABLE 3A

| |
|---|
| 7 |
| 25 |
| 20 |
| 7 |
| 40 |
| 30 |
| 14 |
| 60 |
| 45 |
| 14 |
| 90 |
| 75 |
| 21 |
| 120 |
| 105 |

TABLE 3B

| |
|---|
| 7 |
| about 25 |
| about 20 |
| 7 |
| about 40 |
| about 30 |
| 14 |
| about 60 |
| about 44 |
| 14 |
| about 90 |
| about 75 |
| 21 |
| about 120 |
| about 105 |

TABLE 3C

| 7 | 7 | 7 | 7 | 7 | 7 | 7 | 7 | 7 | 7 | 7 | 7 | 7 |
|---|---|---|---|---|---|---|---|---|---|---|---|---|
| 10 | 15 | 20 | 25 | 30 | 15 | 20 | 25 | 30 | 35 | 20 | 25 | 30 |
| 5 | 5 | 5 | 5 | 5 | 10 | 10 | 10 | 10 | 10 | 15 | 15 | 15 |
| 7 | 7 | 7 | 7 | 7 | 7 | 7 | 7 | 7 | 7 | 7 | 7 | 7 |
| 35 | 40 | 25 | 30 | 35 | 40 | 45 | 30 | 35 | 40 | 45 | 50 | 55 |
| 15 | 15 | 20 | 20 | 20 | 20 | 20 | 25 | 25 | 25 | 25 | 25 | 25 |
| 7 | 7 | 14 | 14 | 14 | 14 | 14 | 14 | 14 | 14 | 14 | 14 | 14 |
| 60 | 65 | 35 | 40 | 45 | 50 | 55 | 60 | 65 | 70 | 75 | 40 | 45 |
| 25 | 25 | 30 | 30 | 30 | 30 | 30 | 30 | 30 | 30 | 30 | 35 | 35 |
| 14 | 14 | 14 | 14 | 14 | 14 | 14 | 14 | 14 | 14 | 14 | 14 | 14 |
| 50 | 55 | 60 | 65 | 70 | 75 | 45 | 50 | 55 | 60 | 65 | 70 | 75 |

TABLE 3C-continued

| | | | | | | | | | | | | |
|---|---|---|---|---|---|---|---|---|---|---|---|---|
| 35 | 35 | 35 | 35 | 35 | 35 | 40 | 40 | 40 | 40 | 40 | 40 | 40 |
| 14 | 14 | 14 | 14 | 14 | 14 | 14 | 14 | 14 | 14 | 14 | 14 | 14 |
| 50 | 55 | 60 | 65 | 70 | 75 | 55 | 60 | 65 | 70 | 75 | 60 | 65 |
| 45 | 45 | 45 | 45 | 45 | 45 | 50 | 50 | 50 | 50 | 50 | 55 | 55 |
| 14 | 14 | 14 | 14 | 14 | 14 | 14 | 14 | 21 | 21 | 21 | 21 | 21 |
| 70 | 75 | 65 | 70 | 75 | 70 | 75 | 75 | 60 | 65 | 70 | 65 | 70 |
| 55 | 55 | 60 | 60 | 60 | 65 | 65 | 70 | 55 | 55 | 55 | 60 | 60 |
| 21 | 21 | 21 | 21 | 21 | | | | | | | | |
| 75 | 70 | 75 | 80 | 85 | 90 | | | | | | | |
| 60 | 65 | 70 | 75 | 80 | 85 | | | | | | | |

Example 16

Dosage and Administration of MM-111 with Lapatinib and Trastuzumab

Treatment for patients with trastuzumab-refractory HER2-overexpressing breast cancer is a critical unmet need in the field of breast oncology, and novel approaches to address this need are required. Although selective tyrosine kinase inhibitors (TKIs) have been highly effective for the treatment of certain tyrosine kinase oncogene-driven cancers, their clinical anti-tumor efficacy in the treatment of HER2-driven breast cancer has been disappointing despite adequate biodistribution and apparent target inhibition. Two completed phase II trials using the most potent HER2 TKI, lapatinib, have reported response rates of only 4%-8% in patients with trastuzumab-refractory HER2-overexpressing breast cancer. It is now known that the effective treatment of HER2+ breast cancer is more complex and resilient than previously thought. Recent evidence has highlighted the role of HER3 and a robust signal buffering capacity inherent in the HER2-HER3 tumor driver that protects it against a two log inhibition of HER2 catalytic activity, placing it beyond the therapeutic index of even the most potent tyrosine kinase inhibitors (TKIs).

Typically, lapatinib is administered at a dosage of 1000 to 1500 mg in 250 mg tablets taken once daily. Lapatinib is often used in combination with another cancer medication, capecitabine, which is taken for 14 day periods with one week in between.

In order to test whether the full inactivation of the HER2-HER3 driver can be achieved with much higher TKI dosing at an intermittent dosing schedule is more efficacious than continuous dosing, a modified dosing schedule is used wherein an increased dose of lapatinib is administered on days 1-5 of a 14 day cycle, said increased dose being a higher dose than the standard dose of 1000 to 1500 mg/day. In some embodiments, the higher lapatinib dose is between 2000 and 9000 mg/d. For example, higher lapatinib dose might be 2000, 2250, 3375, 3000, 3250, 3500, 3750, 4000, 4250, 4500, 4750, 5000, 5250, 5500, 5750, 6000, 6250, 6500, 6750, 7000, 7250, 7500, 7750, 8000, 8250, 8500, 8750, or 9000 mg/day, and so on.

In certain embodiments a loading dose is given on day 1 of the 14-day cycle that is a higher dose than that given on subsequent days, the maintenance dose. For example, a loading dose given on day 1 of the 14 day cycle might be 7000 mg/day, followed by a maintenance dose of 3000 mg/day. Non-limiting examples of loading dose and maintenance dose combinations are listed in Table 4 below.

MM-111 is administered as described in Example 15. In some embodiments the treatment further comprises trastuzumab. Trastuzumab is typically given with an initial loading dose followed by a maintenance dose. For example, trastuzumab may be dosed at a loading dose of 8 mg/kg followed by a maintenance dose of 6 mg/kg every three weeks.

TABLE 4

Exemplary lapatinib dosing schedule: loading dose (top number) and maintenance dose (bottom number) in mg/d

| | | | | | | | | | | | | |
|---|---|---|---|---|---|---|---|---|---|---|---|---|
| 2000 | 2000 | 2000 | 2500 | 2500 | 2500 | 3000 | 3000 | 3000 | 3000 | 3000 | 3500 | 3500 |
| 1000 | 1500 | 2000 | 1000 | 1500 | 2000 | 1000 | 1500 | 2000 | 2500 | 3000 | 1000 | 1500 |
| 3500 | 3500 | 3500 | 4000 | 4000 | 4000 | 4000 | 4000 | 4000 | 4500 | 4500 | 4500 | 4500 |
| 2000 | 2500 | 3000 | 1000 | 1500 | 2000 | 2500 | 3000 | 3500 | 1000 | 1500 | 2000 | 2500 |
| 4500 | 4500 | 4500 | 5000 | 5000 | 5000 | 5000 | 5000 | 5000 | 5000 | 5000 | 5500 | 5500 |
| 3000 | 3500 | 4000 | 1000 | 1500 | 2000 | 2500 | 3000 | 3500 | 4000 | 4500 | 1000 | 1500 |
| 5500 | 5500 | 5500 | 5500 | 5500 | 5500 | 5500 | 6000 | 6000 | 6000 | 6000 | 6000 | 6000 |
| 2000 | 2500 | 3000 | 3500 | 4000 | 4500 | 5000 | 1000 | 1500 | 2000 | 2500 | 3000 | 3500 |
| 6000 | 6000 | 6000 | 6000 | 7500 | 7500 | 7500 | 7500 | 7500 | 7500 | 7500 | 7500 | 7500 |
| 4000 | 4500 | 5000 | 5500 | 1000 | 1500 | 2000 | 2500 | 3000 | 3500 | 4000 | 4500 | 5000 |
| 7500 | 7500 | 7500 | 7500 | 8000 | 8000 | 8000 | 8000 | 8000 | 8000 | 8000 | 8000 | 8000 |
| 5500 | 6000 | 6500 | 7000 | 1000 | 1500 | 2000 | 2500 | 3000 | 3500 | 4000 | 4500 | 5000 |
| 8000 | 8000 | 8000 | 8000 | 8000 | 9000 | 9000 | 9000 | 9000 | 9000 | 9000 | 9000 | 9000 |
| 5500 | 6000 | 6500 | 7000 | 7500 | 1000 | 1500 | 2000 | 2500 | 3000 | 3500 | 4000 | 4500 |
| 9000 | 9000 | 9000 | 9000 | 9000 | 9000 | 9000 | 9000 | | | | | |
| 5000 | 5500 | 6000 | 6500 | 7000 | 7500 | 8000 | 8500 | | | | | |

Example 17

Dosage and Administration of MM-111 with Cisplatin, Capecitabine, and Trastuzumab Administration of MM-111 with cisplatin, capecitabine, and trastuzumab is done, for example, by the following method or minor variations thereof.

Patients are administered therapy on a 21-day treatment cycle. Cisplatin is administered on day 1 of each 21-day cycle by intravenous (i.v.) infusion over two hours, at a dose of 80 mg/m$^2$. Capecitabine is administered orally, twice daily, at a dose of 1000 mg/m$^2$. Up to 21-day cycles of cisplatin and capecitabine are administered. Trastuzumab is administered i.v. at week 1 at an 8 mg/kg loading dose over 90 minutes, followed by a maintenance dose of 6 mg/kg every 21 days over 30-90 minutes. MM-111 is administered as described in the above Examples. For example, MM-111 is administered i.v. over 90 minutes for the first dose and then weekly over 60 minutes thereafter.

Example 18

Dosage and Administration of MM-111 with Lapatinib and Trastuzumb

Administration of MM-111 with lapatinib and trastuzumab is done, for example, by the following method or minor variations thereof. Trastuzumab is administered i.v. at a 4 mg/kg loading dose on week 1 over 90 minutes, followed by a 2 mg/kg weekly maintenance dose thereafter. Lapatinib is given by mouth either at 1000 mg daily doses or at the one of the dose regimens described in Example 13. MM-111 is administered as described in the above Examples. For example, MM-111 is administered i.v. over 90 minutes for the first dose and then weekly over 60 minutes thereafter.

Example 19

Dosage and Administration of MM-111 with Paclitaxel and Trastuzumab

Administration of MM-111 with paclitaxel and trastuzumab is done, for example, by the following method or minor variations thereof. Patients are administered therapy on a 28-day treatment cycle. Paclitaxel dosing begins on day 1 of cycle 1. Paclitaxel is administered at 80 mg/m$^2$ weekly, as an i.v. infusion over 60 minutes. Trastuzumab is administered at a 4 mg/kg loading dose on week 1, i.v. over 90 minutes, followed by a 2 mg/kg weekly maintenance dose thereafter. MM-111 is administered as described in the above Examples. For example, MM-111 is administered i.v. over 90 minutes for the first dose and then weekly over 60 minutes thereafter.

Example 20

Co-Administration of MM-111 and a MEK/PI3k/AKT Inhibitor

MM-111, at dosages described herein (see, e.g., Example 15), can be administered in combination with one or more MAP/ERK kinase (MEK)/phosphatidylinositol 3-kinase (PI3k)/AKT inhibitors to a patient in need thereof for the treatment of a cancer. MM-111 can be administered in the same dosage form as the MEK/PI3AKT inhibitor(s) or these agents can be administered in separate dosage forms.

In preferred embodiments, the MEK/PI3k/AKT inhibitor(s) is selected from AZD6244, BKM-120, GDC-0941, GSK1120212, MK-2206, PD0325901, and Triciribine, and combinations thereof.

In another embodiment, MM-111 and a MEK/PI3k/AKT inhibitor is administered to a patient for the treatment of a malignant tumor, e.g., an ErbB2-expressing or ErbB2 over-expressing tumor (e.g., HER$^{++}$ or HER$^{+++}$ tumors). The tumor may be a melanoma, clear cell sarcoma, head and neck, endometrial, prostate, breast, ovarian, gastric, colon, colorectal, lung, bladder, pancreatic, salivary gland, liver, skin, brain or renal tumor.

Example 21

Coadministration of MM-111 and Other Therapeutic Agents

MM-111 (at dosages described herein; see, e.g., Example 15) can be administered in combination with one or more additional agents to a patient in need thereof for the treatment of a cancer. In particular, MM-111 can be administered in combination with MM-151 (oligoclonal anti-EGFR mixture), TDM-1 (Trastuzumab emtansine; an antibody-drug conjugate of the antibody trastuzumab linked to maytansine derivative (DM1)), and an mTOR inhibitor (e.g., one or more of the mTOR inhibitors listed in the attached appendix), and combinations thereof.

MM-151 is an oligoclonal therapeutic that is a mixture of three fully human monoclonal antibodies designed to bind to non-overlapping epitopes of the epidermal growth factor receptor, or EGFR (also known as ErbB1). An oligoclonal therapeutic is a mixture of two or more distinct monoclonal antibodies. MM-151 is disclosed, e.g., in copending PCT Application No. PCT/US12/45235, incorporated herein by reference.

MM-111 can be administered in the same dosage form as MM-151, TDM-1, and/or the mTOR inhibitor(s), or the agents can be administered in separate dosage forms.

In an embodiment, MM-111 and one or more of MM-151, TDM-1, and/or the mTOR inhibitor(s) is administered to a patient for the treatment of a malignant tumor, e.g., an ErbB2-expressing or ErbB2 over-expressing tumor (e.g., HER$^{++}$ or HER$^{+++}$ tumors). The tumor may be a melanoma, clear cell sarcoma, head and neck, endometrial, prostate, breast, ovarian, gastric, colon, colorectal, lung, bladder, pancreatic, salivary gland, liver, skin, brain or renal tumor.

In another embodiment, MM-111 and MM-151 are co-administered to treat a solid tumor (e.g., an advanced refractory solid tumor) in a patient in need thereof.

Endnotes

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All patents patent applications and publications mentioned herein are incorporated by reference to the same extent as if each independent patent or patent application was specifically and individually indicated to be incorporated by reference in its entirety. In particular, WO 2012/116317 is incorporated herein by reference in its entirety.

APPENDIX

Anticancer Agents

The Table and Appendix below describe effective an anti-estrogen agents, receptor tyrosine kinase inhibitors; MEK/PI3 kinase/AKT inhibitors, and mTOR inhibitors that can be used in the methods and compositions of the invention.

The bispecific anti-ErbB2/anti-ErbB3 antibody co-administered in combination with an agent selected from i) an effective amount of an anti-estrogen agent; ii) an effective amount of a receptor tyrosine kinase inhibitor; iii) a MEK/PI3 kinase/AKT inhibitor; iv) MM-151; v) an mTOR inhibitor; and/or vi) trastuzumab or TMD1, and combinations thereof, can be further co-administered with at least a third antineoplastic agent selected from any of those disclosed in the Table and Appendix below.

TABLE 5

Exemplary antineoplastic agents for treatment of breast cancer in combination with a bispecific anti-ErbB2/anti-ErbB3 antibody.

| Therapeutic Class | Exemplary Agent (Generic/Tradename) | Exemplary Dose |
|---|---|---|
| Mitotic Inhibitors | paclitaxel (TAXOL ®; ABRAXANE ®) | 175 mg/m$^2$ |
|  | docetaxel (TAXOTERE ®) | 60-100 mg/m$^2$ |
| Topoisomerase Inhibitors | camptothecin |  |
|  | topotecan hydrochloride (HYCAMTIN ®) |  |
|  | etoposide (EPOSIN ®) |  |
| Alkylating Agents | cyclophosphamide (CYTOXAN ®) | 600 mg/m$^2$ |
| Platinum-Based Agents | Cisplatin | 20-100 mg/m$^2$ |
|  | carboplatin (PARAPLATIN ®) | 300 mg/m$^2$ |
|  | nedaplatin (AQUPLA ®) |  |
|  | oxaliplatin (ELOXATIN ®) | 65-85 mg/m$^2$ |
|  | satraplatin (SPERA ®)) |  |
|  | triplatin tetranitrate |  |
| Selective Estrogen Modulators (SERM) | tamoxifen (NOLVADEX ®) | 20-40 mg/day |
|  | raloxifene (EVISTA ®) | 60 mg/day |
|  | toremifene (FARESTON ®) |  |
| Antimetabolites | methotrexate | 40 mg/m$^2$ |
|  | Fluorouracil (5-FU) | 500 mg/m$^2$ |
|  | Raltitrexed |  |
| Antitumor Antibiotics | Doxorubicin (ADRIAMYCIN ®) | 40-75 mg/m$^2$ |
|  | epirubicin (ELLENCE ®) | 60-120 mg/m$^2$ |
| Aromatase Inhibitors | aminoglutethimide (CYTADREN ®) | 250-2000 mg/day |
|  | anastrozole (ARIMIDEX ®) | 1 mg/day |
|  | letrozole (FEMARA ®) | 2.5 mg/day |
|  | Vorozole |  |
|  | exemestane (AROMASIN ®) | 25-50 mg/day |
|  | Testolactone |  |
|  | fadrozole (AFEMA ®) |  |
| Anti-VEGF Agents | bevacizumab (AVASTIN ®) | 10 mg/kg |
| Anti-ErbB2 (HER2/neu) Agents | trastuzumab (HERCEPTIN ®) | 2-8 mg/kg |
|  | Pertuzumab (OMNITARG ®) |  |
| Anti-ErbB3 (HER3) Agents | U3-1287 (AMG 888) |  |

APPENDIX

Anticancer Agents

| Other anticancer agents for combination with a bispecific anti-ErbB2/anti-ErbB3 antibody | Brand Name(s) | Manufacturer/Proprietor |
|---|---|---|
| Anti-IGF1R Antibodies | | |
| AMG 479 (fully humanized mAb) |  | Amgen |
| IMCA12 (fully humanized mAb) |  | ImClone |
| NSC-742460 |  | Dyax |
| 19D12 (fully humanized mAb) |  |  |
| CP751-871 (fully humanized mAb) |  | Pfizer |
| H7C10 (humanized mAb) |  |  |
| alphaIR3 (mouse) |  |  |
| scFV/FC (mouse/human chimera) |  |  |
| EM/164 (mouse) |  |  |
| MK-0646, F50035 |  | Pierre Fabre Medicament, Merck |
| Small Molecules Targeting IGF1R | | |
| NVP-AEW541 |  | Novartis |
| BMS-536,924 (1H-benzoimidazol-2-yl)-1H-pyridin-2-one) |  | Bristol-Myers Squibb |
| BMS-554,417 |  | Bristol-Myers Squibb |
| Cycloligan |  |  |
| TAE226 |  |  |
| PQ401 |  |  |
| Anti-EGFR Antibodies | | |
| INCB7839 |  | Incyte |
| Bevacizumab | Avastin ® | Genentech |
| Cetuximab | Erbitux ® | IMCLONE |
| mAb 806 |  |  |
| Matuzumab (EMD72000) |  |  |
| Nimotuzumab (TheraCIM) |  |  |

| Other anticancer agents for combination with a bispecific anti-ErbB2/anti-ErbB3 antibody | Brand Name(s) | Manufacturer/Proprietor |
|---|---|---|
| Panitumumab | Vectibix ® | Amgen |
| MM-151 | | Merrimack |
| Sym004 | | Symphogen |
| Zalutumumab | | Humax |
| Anti-ErbB3 Therapeutics | — | — |
| U3-1287/AMG888 | | U3 Pharma/Amgen |
| MM-121 | | Merrimack Pharmaceuticals |
| Anti-ErbB2 Therapeutics | — | — |
| trastuzumab | Herceptin ® | Genentech |
| HKI-272 - neratinib | | Wyeth |
| KOS-953 - tanespimycin | | Kosan Biosciences |
| Her/ErbB Dimerization Inhibitors | | |
| 2C4, R1273 - Pertuzumab | , Omnitarg ® | Genentech, Roche |
| Small Molecules Targeting EGFR | | |
| CI-1033 (PD 183805) | | Pfizer, Inc. |
| EKB-569 | | |
| Gefitinib | IRESSA ™ | AstraZeneca |
| Lapatinib (GW572016) | | GlaxoSmithKline |
| Lapatinib Ditosylate | Tykerb ® | SmithKline Beecham |
| Erlotinib HCl (OSI-774) | Tarceva ® | OSI Pharms |
| PD158780 | | |
| PKI-166 | | Novartis |
| Tyrphostin AG 1478 (4-(3-Chloroanillino)-6,7-dimethoxyquinazoline) | | |
| Afatinib (BIBW 2992) | | Boehringer Ingelheim |
| Small Molecules Targeting MEK | | |
| CI-1040 (PD184352) | | |
| AZD6244 (Selumetinib) | | |
| RDEA119 (BAY 869766) | | |
| GSK1120212 | | Glaxo Smith Kline |
| PD-0325901 | | |
| GDC-0973 | | Genentech |
| Anti-cMet Antibody Therapies | | |
| AVEO (AV299) | | AVEO |
| AMG102 | | Amgen |
| 5D5 (OA-5D5) | | Genentech |
| Small Molecules Targeting cMet | | |
| PHA665752 | | |
| ARQ-650RP | | ArQule |
| ARQ 197 | | ArQule |
| Alkylating Agents | | |
| BCNU→ 1,3-bis t2-chloroethyl)-nitrosourea | | |
| Bendamustine | | |
| Busulfan | Myleran | GlaxoSmithKline |
| Carboplatin | Paraplatin | Bristol-Myers Squibb |
| Carboquone | | |
| Carmustine | | |
| CCNU→ 1,-(2-chloroethyl)-3-cyclohexyl-1-nitrosourea (methyl CCNU) | | |
| Chlorambucil | Leukeran ® | Smithkline Beecham |
| Chlormethine | | |
| Cisplatin (Cisplatinum, CDDP) | Platinol | Bristol-Myers |
| Cyclophosphamide | Cytoxan | Bristol-Myers Squibb |
| Dacarbazine (DTIC) | Neosar | Teva Parenteral |
| Fotemustine | | |
| Hexamethylmelamine (Altretamine, HMM) | Hexalen ® | MGI Pharma, Inc. |
| Ifosfamide | Mitoxana ® | ASTA Medica |
| Lomustine | | |
| Mannosulfan | | |
| Melphalan | Alkeran ® | GlaxoSmithKline |
| Nedaplatin | | |
| Nimustine | | |
| Oxaliplatin | Eloxatin ® | Sanofi-Aventis US |
| Prednimustine, | Matulane | Sigma-Tau Pharmaceuticals, Inc. |
| Procarbazine HCL | | |
| Ribonucleotide Reductase Inhibitor (RNR) | | |
| Ranimustine | | |
| Satraplatin | | |

| Other anticancer agents for combination with a bispecific anti-ErbB2/anti-ErbB3 antibody | Brand Name(s) | Manufacturer/Proprietor |
|---|---|---|
| Semustine | | |
| Streptozocin | | |
| Temozolomide | | |
| Treosulfan | | |
| Triaziquone | | |
| Triethylene Melamine | | |
| ThioTEPA | | Bedford, Abraxis, Teva |
| Triplatin tetranitrate | | |
| Trofosfamide | | |
| Uramustine | | |
| Antimetabolites | | |
| 5-azacytidine | | |
| Flourouracil (5-FU)/Capecitabine | | |
| 6-mercaptopurine (Mercaptopurine, 6-MP) | | |
| 6-Thioguanine (6-TG) | Purinethol ® | Teva |
| Cytosine Arabinoside (Cytarabine, Ara-C) | Thioguanine ® | GlaxoSmithKline |
| Azathioprine | Azasan ® | AAIPHARMA LLC |
| Capecitabine | XELODA ® | HLR (Roche) |
| Cladribine (2-CdA, 2-chlorodeoxyadenosine) | Leustatin ® | Ortho Biotech |
| 5-Trifluoromethyl-2'-deoxyuridine | | |
| Fludarabine phosphate | Fludara ® | Bayer Health Care |
| Floxuridine (5-fluoro-2) | FUDR ® | Hospira, Inc. |
| Methotrexate sodium | Trexall | Barr |
| Pemetrexed | Alimta ® | Lilly |
| Pentostatin | Nipent ® | Hospira, Inc. |
| Raltitrexed | Tomudex ® | AstraZeneca |
| Tegafur | | |
| Aromatose Inhibitor | | |
| Ketoconazole | | |
| Glucocorticoids | | |
| Dexamethasone | Decadron ® Dexasone, Diodex, Hexadrol, Maxidex | Wyeth, Inc. |
| Prednisolone | | |
| Prednisone | Deltasone, Orasone, Liquid Pred, Sterapred ® | |
| Immunotherapeutics | | |
| Alpha interferon | | |
| Angiogenesis Inhibitor | Avastin ® | Genentech |
| IL-12→ Interleukin 12 | | |
| IL-2→ Interleukin 2 (Aldesleukin) | Proleukin ® | Chiron |
| Receptor Tyrosine Kinase Inhibitors | | |
| AMG 386 | | Amgen |
| Axitinib ((AG-013736) | | Pfizer, Inc |
| Bosutinib (SKI-606) | | Wyeth |
| Brivanib alalinate (BMS-582664) | | BMS |
| Cediranib (AZD2171) | Recentin | AstraVeneca |
| Dasatinib (BMS-354825) | Sprycel ® | Bristol-Myers Squibb |
| Imatinib mesylate | Gleevec | Novartis |
| Lestaurtinib (CEP-701) | | Cephalon |
| Motesanib diphosphate (AMG-706) | | Amgen/Takeda |
| Nilotinib hydrochloride monohydrate | Tasigna ® | Novartis |
| Pazopanib HCL (GW786034) | Armala | GSK |
| Semaxanib (SU5416) | | Pharmacia, |
| Sorafenib tosylate | Nexavar ® | Bayer |
| Sunitinib malate | Sutent ® | Pfizer, Inc. |
| Vandetanib (AZD647) | Zactima | AstraZeneca |
| Vatalanib; PTK-787 | | Novartis; Bayer Schering Pharma |
| XL184, NSC718781 | | Exelixis, GSK |
| Microtubule-Targeting Agents | | |
| Colchicine | | |
| Docetaxel | Taxotere ® | Sanofi-Aventis US |
| Ixabepilone | IXEMPRA ™ | Bristol-Myers Squibb |
| Larotaxel | | Sanofi-aventis |
| Ortataxel | | Spectrum Pharmaceuticals |
| Nanoparticle paclitaxel (ABI-007) | Abraxane ® | Abraxis BioScience, Inc. |
| Paclitaxel | Taxol ® | Bristol-Myers Squibb |

| Other anticancer agents for combination with a bispecific anti-ErbB2/anti-ErbB3 antibody | Brand Name(s) | Manufacturer/Proprietor |
|---|---|---|
| Tesetaxel | | Genta |
| Vinblastine sulfate | Velban ® | Lilly |
| Vincristine | Oncovin ® | Lilly |
| Vindesine sulphate | Eldisine ® | Lilly |
| Vinflunine | | Pierre Fabre |
| Vinorelbine tartrate | Navelbine ® | Pierre Fabre |
| mTOR Inhibitors | | |
| Deforolimus (AP23573, MK 8669) | | ARIAD Pharmaceuticals, Inc |
| Everolimus (RAD001, RAD001C) | Certican ®, Afinitor | Novartis |
| Sirolimus (Rapamycin) | Rapamune ® | Wyeth Pharama |
| Temsirolimus (CCI-779) | Torisel ® | Wyeth Pharama |
| Protein Synthesis Inhibitor | | |
| L-asparaginase | Elspar ® | Merck & Co. |
| Somatostatin Analogue | | |
| Octreotide acetate | Sandostatin ® | Novartis |
| Topoisomerase Inhibitors | | |
| Actinomycin D | | |
| Camptothecin (CPT) | | |
| Belotecan | | |
| Daunorubicin citrate | Daunoxome ® | Gilead |
| Doxorubicin hydrochloride | Doxil ® | Alza |
| | Vepesid ® | Bristol-Myers Squibb |
| Etoposide | Etopophos | Hospira, Bedford, Teva Parenteral, Etc. |
| Irinotecan HCL (CPT-11) | Camptosar ® | Pharmacia & Upjohn |
| Mitoxantrone HCL | Novantrone | EMD Serono |
| Rubitecan | | |
| Teniposide (VM-26) | Vumon ® | Bristol-Myers Squibb |
| Topotecan HCL | Hycamtin ® | GlaxoSmithKline |
| Chemotherapeutic Agents | | |
| Adriamycin, 5-Fluorouracil, Cytoxin, Bleomycin, Mitomycin C, Daunomycin, Carminomycin, Aminopterin, Dactinomycin, Mitomycins, Esperamicins Clofarabine, Mercaptopurine, Pentostatin, Thioguanine, Cytarabine, Decitabine, Floxuridine, Gemcitabine (Gemzar), Enocitabine, Sapacitabine | | |
| Hormonal Therapies | | |
| Abarelix | Plenaxis ™ | Amgen |
| Abiraterone acetate | CB7630 | BTG plc |
| Afimoxifene | TamoGel | Ascend Therapeutics, Inc. |
| Anastrazole | Arimidex ® | AstraZeneca |
| Aromatase inhibitor | Atamestane plus toremifene | Intarcia Therapeutics, Inc. |
| | Arzoxifene | Eli Lilly & Co. |
| Asentar; DN-101 | | Novartis; Oregon Health & Science Univ. |
| Bicalutamide | Casodex ® | AstraZeneca |
| Buserelin | Suprefact ® | Sanofi Aventis |
| Cetrorelix | Cetrotide ® | EMD Serono |
| Exemestane | Aromasin ® | Pfizer |
| Exemestane | Xtane | Natco Pharma, Ltd. |
| Fadrozole (CGS 16949A) | | |
| Flutamide | Eulexin ® | Schering |
| Flutamide | Prostacur | Laboratorios Almirall, S.A. |
| Fulvestrant | Faslodex ® | AstraZeneca |
| Goserelin acetate | Zoladex ® | AstraZeneca |
| Letrozole | Femara ® | Novartis |
| Letrozole (CGS20267) | Femara | Chugai Pharmaceutical Co., Ltd. |
| Letrozole | Estrochek | Jagsonpal Pharmaceuticals, Ltd. |
| Letrozole | Letrozole | Indchemie Health Specialities |
| Leuprolide acetate | Eligard ® | Sanofi Aventis |
| Leuprolide acetate | Leopril | VHB Life Sciences, Inc. |
| Leuprolide acetate | Lupron ®/Lupron Depot | TAP Pharma |
| Leuprolide acetate | Viador | Bayer AG |
| Megestrol acetate | Megace ® | Bristol-Myers Squibb |
| Magestrol acetate | Estradiol Valerate (Delestrogen) | Jagsonpal Pharmaceuticals, Ltd. |

| Other anticancer agents for combination with a bispecific anti-ErbB2/anti-ErbB3 antibody | Brand Name(s) | Manufacturer/Proprietor |
|---|---|---|
| Medroxyprogesterone acetate | Veraplex | Combiphar |
| MT206 | | Medisyn Technologies, Inc. |
| Nafarelin | | |
| Nandrolone decanoate | Zestabolin | Mankind Pharma, Ltd. |
| Nilutamide | Nilandron ® | Aventis Pharmaceuticals |
| Raloxifene HCL | Evista ® | Lilly |
| Tamoxifen | Taxifen | Yung Shin Pharmaceutical |
| Tamoxifen | Tomifen | Alkem Laboratories, Ltd. |
| Tamoxifen citrate | Nolvadex | AstraZeneca |
| Tamoxifen citrate | Soltamox | EUSA Pharma, Inc. |
| Tamoxifen citrate | Tamoxifen citrate SOPHARMA | Sopharma JSCo. |
| Toremifene citrate | Fareston ® | GTX, Inc. |
| Triptorelin pamoate | Trelstar ® | Watson Labs |
| Triptorelin pamoate | Trelstar Depot | Paladin Labs, Inc. |
| Protein Kinase B (PKB) Inhibitors | | |
| Akt Inhibitor ASTEX | | Astex Therapeutics |
| Akt Inhibitors NERVIANO | | Nerviano Medical Sciences |
| AKT Kinase Inhibitor TELIK | | Telik, Inc. |
| AKT Inhibitor Triciribine | | |
| AKT DECIPHERA | | Decipher Pharmaceuticals, LLC |
| Perifosine (KRX0401, D-21266) | | Keryx Biopharmaceuticals, Inc., AEterna Zentaris, Inc. |
| Perifosine with Docetaxel | | Keryx Biopharmaceuticals, Inc., AEterna Zentaris, Inc. |
| Perifosine with Gemcitabine | | AEterna Zentaris, Inc. |
| Perifosine with Paclitaxel | | Keryx Biopharmaceuticals, Inc, AEterna Zentaris, Inc. |
| Protein Kinase-B inhibitor DEVELOGEN | | DeveloGen AG |
| PX316 | | Oncothyreon, Inc. |
| RX0183 | | Rexahn Pharmaceuticals, Inc. |
| RX0201 | | Rexahn Pharmaceuticals, Inc. |
| VQD002 | | VioQuest Pharmaceuticals, Inc. |
| XL418 | | Exelixis, Inc. |
| ZEN027 | | AEterna Zentaris, Inc. |
| Phosphatidylinositol 3-Kinase (PI3K) Inhibitors | | |
| BEZ235 | | Novartis AG |
| BGT226 | | Novartis AG |
| CAL101 | | Calistoga Pharmaceuticals, Inc. |
| CHR4432 | | Chroma Therapeutics, Ltd. |
| Erk/PI3K Inhibitors ETERNA | | AEterna Zentaris, Inc. |
| GDC0941 | | Genentech Inc./Piramed Limited/Roche Holdings, Ltd. |
| Enzastaurin HCL (LY317615) | Enzastaurin | Eli Lilly |
| LY294002/Wortmannin | | Eli Lilly |
| PI3K Inhibitors SEMAFORE | | Semafore Pharmaceuticals |
| PX866 | | Oncothyreon, Inc. |
| SF1126 | | Semafore Pharmaceuticals |
| VMD-8000 | | VM Discovery, Inc. |
| XL147 | | Exelixis, Inc. |
| XL147 with XL647 | | Exelixis, Inc. |
| XL765 | | Exelixis, Inc. |
| PI-103 | | Roche/Piramed |
| BKM120 | | |
| Cyclin-dependent kinase inhibitors | | |
| CYC200, r-roscovitine | Seliciclib | Cyclacel Pharma |
| NSC-649890, L86-8275, HMR-1275 | Alvocidib | NCI |
| TLr9, CD289 | | |
| IMOxine | | Merck KGaA |
| HYB2055 | | Idera |
| IMO-2055 | | Isis Pharma |
| 1018 ISS | | Dynavax Technologies/UCSF |
| PF-3512676 | | Pfizer |
| Enzyme Inhibitor | | |
| Lonafarnib (SCH66336) | Sarasar | SuperGen, U Arizona |

| Other anticancer agents for combination with a bispecific anti-ErbB2/anti-ErbB3 antibody | Brand Name(s) | Manufacturer/Proprietor |
|---|---|---|
| Anti-TRAIL | | |
| AMG-655 | | Aeterna Zentaris, Keryx Biopharma |
| Apo2L/TRAIL, AMG951 | | Genentech, Amgen |
| Apomab (fully humanized mAb | | Genentech |
| Other | | |
| Imprime PGG | | Biothera |
| CHR-2797 | AminopeptidaseM1 | Chroma Therapeutics |
| E7820, NSC 719239 | Integrin-alpha2 | Eisai |
| INCB007839 | ADAM 17, TACE | Incyte |
| CNF2024, BIIB021 | Hsp90 | Biogen Idec |
| MP470, HPK-56 | Kit/Met/Ret | Shering-Plough |
| SNDX-275/MS-275 | HDAC | Syndax |
| Zarnestra, Tipifarnib, R115777 | Ras | Janssen Pharma |
| Volociximab; Eos 200-4, M200 | alpha5β1 integrin | Biogen Idec; Eli Lilly/UCSF/PDL BioPharma |
| Apricoxib (TP2001) | COX-2 Inhibitor | Daiichi Sankyo; Tragara Pharma |

What is claimed is:

1. A method of treating a subject with a malignant tumor, the method comprising co-administering to the subject an effective amount of trametinib and a bispecific anti-ErbB2/anti-ErbB3 antibody that inhibits heregulin activation of ErbB2 and ErbB3 and, optionally, an effective amount of trastuzumab or ado-trastuzumab emtansine, wherein the co-administration to the subject creates a substantially superadditive effect.

2. The method of claim 1, wherein the co-administration to the subject does not create a drug-drug interaction-mediated toxicity in the subject.

3. The method of claim 1 wherein the bispecific anti-ErbB2/anti-ErbB3 antibody comprises the amino acid sequence set forth in SEQ ID NO:1.

4. The method of claim 1 further comprising administering an effective amount of capecitabine and/or cisplatin.

5. The method of claim 1, wherein the subject is a human.

* * * * *

SEQUENCE LISTING

<160> NUMBER OF SEQ ID NOS: 1

<210> SEQ ID NO 1
<211> LENGTH: 1095
<212> TYPE: PRT
<213> ORGANISM: Artificial Sequence
<220> FEATURE:
<223> OTHER INFORMATION: Synthetic Construct

<400> SEQUENCE: 1

```
Gln Val Gln Leu Gln Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
             20                  25                  30

Trp Met Ser Trp Val Arg Gln Ala Pro Gly Lys Gly Leu Glu Trp Val
         35                  40                  45

Ala Asn Ile Asn Arg Asp Gly Ser Ala Ser Tyr Tyr Val Asp Ser Val
     50                  55                  60

Lys Gly Arg Phe Thr Ile Ser Arg Asp Asp Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Asp Arg Gly Val Gly Tyr Phe Asp Leu Trp Gly Arg Gly Thr
        100                 105                 110

Leu Val Thr Val Ser Ser Ala Ser Thr Gly Gly Gly Ser Gly Gly
        115                 120                 125

Gly Gly Ser Gly Gly Gly Ser Gln Ser Ala Leu Thr Gln Pro Ala
        130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Phe Val Ser Trp Tyr Gln Gln
                165                 170                 175

His Pro Gly Lys Ala Pro Lys Leu Met Ile Tyr Asp Val Ser Asp Arg
            180                 185                 190

Pro Ser Gly Val Ser Asp Arg Phe Ser Gly Ser Lys Ser Gly Asn Thr
        195                 200                 205
```

-continued

```
Ala Ser Leu Ile Ile Ser Gly Leu Gln Ala Asp Glu Ala Asp Tyr
    210                 215                 220
Tyr Cys Ser Ser Tyr Gly Ser Ser Thr His Val Ile Phe Gly Gly
225                 230                 235                 240
Gly Thr Lys Val Thr Val Leu Gly Ala Ala Ser Asp Ala His Lys Ser
                245                 250                 255
Glu Val Ala His Arg Phe Lys Asp Leu Gly Glu Asn Phe Lys Ala
                260                 265                 270
Leu Val Leu Ile Ala Phe Ala Gln Tyr Leu Gln Gln Ser Pro Phe Glu
            275                 280                 285
Asp His Val Lys Leu Val Asn Glu Val Thr Glu Phe Ala Lys Thr Cys
    290                 295                 300
Val Ala Asp Glu Ser Ala Glu Asn Cys Asp Lys Ser Leu His Thr Leu
305                 310                 315                 320
Phe Gly Asp Lys Leu Cys Thr Val Ala Thr Leu Arg Glu Thr Tyr Gly
                325                 330                 335
Glu Met Ala Asp Cys Cys Ala Lys Gln Glu Pro Glu Arg Asn Glu Cys
            340                 345                 350
Phe Leu Gln His Lys Asp Asp Asn Pro Asn Leu Pro Arg Leu Val Arg
        355                 360                 365
Pro Glu Val Asp Val Met Cys Thr Ala Phe His Asp Asn Glu Glu Thr
    370                 375                 380
Phe Leu Lys Lys Tyr Leu Tyr Glu Ile Ala Arg Arg His Pro Tyr Phe
385                 390                 395                 400
Tyr Ala Pro Glu Leu Leu Phe Phe Ala Lys Arg Tyr Lys Ala Ala Phe
                405                 410                 415
Thr Glu Cys Cys Gln Ala Ala Asp Lys Ala Ala Cys Leu Leu Pro Lys
            420                 425                 430
Leu Asp Glu Leu Arg Asp Glu Gly Lys Ala Ser Ser Ala Lys Gln Arg
        435                 440                 445
Leu Lys Cys Ala Ser Leu Gln Lys Phe Gly Glu Arg Ala Phe Lys Ala
    450                 455                 460
Trp Ala Val Ala Arg Leu Ser Gln Arg Phe Pro Lys Ala Glu Phe Ala
465                 470                 475                 480
Glu Val Ser Lys Leu Val Thr Asp Leu Thr Lys Val His Thr Glu Cys
                485                 490                 495
Cys His Gly Asp Leu Leu Glu Cys Ala Asp Asp Arg Ala Asp Leu Ala
            500                 505                 510
Lys Tyr Ile Cys Glu Asn Gln Asp Ser Ile Ser Ser Lys Leu Lys Glu
        515                 520                 525
Cys Cys Glu Lys Pro Leu Leu Glu Lys Ser His Cys Ile Ala Glu Val
    530                 535                 540
Glu Asn Asp Glu Met Pro Ala Asp Leu Pro Ser Leu Ala Ala Asp Phe
545                 550                 555                 560
Val Glu Ser Lys Asp Val Cys Lys Asn Tyr Ala Glu Ala Lys Asp Val
                565                 570                 575
Phe Leu Gly Met Phe Leu Tyr Glu Tyr Ala Arg Arg His Pro Asp Tyr
            580                 585                 590
Ser Val Val Leu Leu Leu Arg Leu Ala Lys Thr Tyr Glu Thr Thr Leu
        595                 600                 605
Glu Lys Cys Cys Ala Ala Ala Asp Pro His Glu Cys Tyr Ala Lys Val
    610                 615                 620
Phe Asp Glu Phe Lys Pro Leu Val Glu Glu Pro Gln Asn Leu Ile Lys
```

```
                625                 630                 635                 640
        Gln Asn Cys Glu Leu Phe Glu Gln Leu Gly Glu Tyr Lys Phe Gln Asn
                        645                 650                 655
        Ala Leu Leu Val Arg Tyr Thr Lys Lys Val Pro Gln Val Ser Thr Pro
                        660                 665                 670
        Thr Leu Val Glu Val Ser Arg Asn Leu Gly Lys Val Gly Ser Lys Cys
                        675                 680                 685
        Cys Lys His Pro Glu Ala Lys Arg Met Pro Cys Ala Glu Asp Tyr Leu
                        690                 695                 700
        Ser Val Val Leu Asn Gln Leu Cys Val Leu His Glu Lys Thr Pro Val
        705                 710                 715                 720
        Ser Asp Arg Val Thr Lys Cys Cys Thr Glu Ser Leu Val Asn Arg Arg
                        725                 730                 735
        Pro Cys Phe Ser Ala Leu Glu Val Asp Glu Thr Tyr Val Pro Lys Glu
                        740                 745                 750
        Phe Gln Ala Glu Thr Phe Thr Phe His Ala Asp Ile Cys Thr Leu Ser
                        755                 760                 765
        Glu Lys Glu Arg Gln Ile Lys Lys Gln Thr Ala Leu Val Glu Leu Val
        770                 775                 780
        Lys His Lys Pro Lys Ala Thr Lys Glu Gln Leu Lys Ala Val Met Asp
        785                 790                 795                 800
        Asp Phe Ala Ala Phe Val Glu Lys Cys Cys Lys Ala Asp Asp Lys Glu
                        805                 810                 815
        Thr Cys Phe Ala Glu Glu Gly Lys Lys Leu Val Ala Ala Ser Gln Ala
                        820                 825                 830
        Ala Leu Gly Leu Ala Ala Ala Leu Gln Val Gln Leu Val Gln Ser Gly
                        835                 840                 845
        Ala Glu Val Lys Lys Pro Gly Glu Ser Leu Lys Ile Ser Cys Lys Gly
                        850                 855                 860
        Ser Gly Tyr Ser Phe Thr Ser Tyr Trp Ile Ala Trp Val Arg Gln Met
        865                 870                 875                 880
        Pro Gly Lys Gly Leu Glu Tyr Met Gly Leu Ile Tyr Pro Gly Asp Ser
                        885                 890                 895
        Asp Thr Lys Tyr Ser Pro Ser Phe Gln Gly Gln Val Thr Ile Ser Val
                        900                 905                 910
        Asp Lys Ser Val Ser Thr Ala Tyr Leu Gln Trp Ser Ser Leu Lys Pro
                        915                 920                 925
        Ser Asp Ser Ala Val Tyr Phe Cys Ala Arg His Asp Val Gly Tyr Cys
        930                 935                 940
        Thr Asp Arg Thr Cys Ala Lys Trp Pro Glu Trp Leu Gly Val Trp Gly
        945                 950                 955                 960
        Gln Gly Thr Leu Val Thr Val Ser Gly Gly Gly Ser Ser Gly
                        965                 970                 975
        Gly Gly Ser Gly Gly Gly Ser Gln Ser Val Leu Thr Gln Pro Pro
                        980                 985                 990
        Ser Val Ser Ala Ala Pro Gly Gln Lys Val Thr Ile Ser Cys Ser Gly
                        995                 1000                1005
        Ser Ser Ser Asn Ile Gly Asn Asn Tyr Val Ser Trp Tyr Gln Gln
            1010                1015                1020
        Leu Pro Gly Thr Ala Pro Lys Leu Leu Ile Tyr Asp His Thr Asn
            1025                1030                1035
        Arg Pro Ala Gly Val Pro Asp Arg Phe Ser Gly Ser Lys Ser Gly
            1040                1045                1050
```

```
Thr Ser Ala Ser Leu Ala Ile Ser Gly Phe Arg Ser Glu Asp Glu
    1055            1060            1065

Ala Asp Tyr Tyr Cys Ala Ser Trp Asp Tyr Thr Leu Ser Gly Trp
    1070            1075            1080

Val Phe Gly Gly Gly Thr Lys Leu Thr Val Leu Gly
    1085            1090            1095
```